United States Patent
Stein et al.

(10) Patent No.: US 9,345,449 B2
(45) Date of Patent: *May 24, 2016

(54) PROSTHETIC COMPONENT FOR MONITORING JOINT HEALTH

(71) Applicant: Orthosensor Inc., Dania Beach, FL (US)

(72) Inventors: Marc Stein, Chandler, AZ (US);
Andrew Chase, Chandler, AZ (US);
John Keggi, San Francisco, CA (US);
Noah Bonnheim, Dallas, TX (US);
Natalie Burkhard, Laguna Hills, CA (US); Philip Henson, Somerset, NJ (US)

(73) Assignee: ORTHOSENSOR INC, Dania Beach, FL (US)

( * ) Notice: Subject to any disclaimer, the term of this patent is extended or adjusted under 35 U.S.C. 154(b) by 143 days.

This patent is subject to a terminal disclaimer.

(21) Appl. No.: 14/205,255

(22) Filed: Mar. 11, 2014

(65) Prior Publication Data

US 2014/0206952 A1 Jul. 24, 2014

Related U.S. Application Data

(63) Continuation of application No. 13/406,519, filed on Feb. 27, 2012, now Pat. No. 8,720,270, which is a continuation-in-part of application No. 12/825,852, filed on Jun. 29, 2010, now Pat. No. 8,146,422, and a (Continued)

(51) Int. Cl.
*A61B 5/00* (2006.01)
*A61B 8/08* (2006.01)
(Continued)

(52) U.S. Cl.
CPC ............. *A61B 8/0875* (2013.01); *A61B 5/0082* (2013.01); *A61B 5/01* (2013.01);
(Continued)

(58) Field of Classification Search
CPC .................................... A61B 5/22; A61B 5/00

USPC ........................................ 73/379.01; 600/301
See application file for complete search history.

(56) References Cited

U.S. PATENT DOCUMENTS 3,573,782 A 4/1971 Williams
3,727,616 A 4/1973 Lenzkes
(Continued)

FOREIGN PATENT DOCUMENTS

CN 1509156 6/2004
CN 1960680 5/2007
(Continued)

OTHER PUBLICATIONS

International Search Report for PCT/US2012/056689 dated Feb. 25, 2013, 4 pages.
(Continued)

*Primary Examiner* — Jewel V Thompson

(57) ABSTRACT

A prosthetic component suitable for long-term implantation is provided. The prosthetic component includes electronic circuitry and sensors to measure a parameter of the muscular-skeletal system. The prosthetic component comprises a first structure having at least one support surface, a second structure having at least one feature configured to couple to bone, and at least one sensor. The electronic circuitry and sensors are hermetically sealed within the prosthetic component. The prosthetic component includes at least on transmissive region. The transmissive region can be located in a region that has exposure to a region outside the joint. The transmissive region can comprise glass. One or more sensors can be used to monitor synovial fluid in proximity to the joint to determine joint health. The transmissive region can be used to support communication between the electronic circuitry and remote system.

20 Claims, 26 Drawing Sheets

Related U.S. Application Data continuation-in-part of application No. 12/826,349, filed on Jun. 29, 2010, now Pat. No. 8,245,583, and a continuation-in-part of application No. 13/242,277, filed on Sep. 23, 2011, and a continuation-in-part of application No. 13/242,662, filed on Sep. 23, 2011.

(60) Provisional application No. 61/221,767, filed on Jun. 30, 2009, provisional application No. 61/221,779, filed on Jun. 30, 2009, provisional application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,867, filed on Jun. 30, 2009, provisional application No. 61/221,874, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/221,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009, provisional application No. 61/221,761, filed on Jun. 30, 2009.

(51) Int. Cl.
  *A61B 5/01* (2006.01)
  *A61B 5/103* (2006.01)
  *A61B 5/145* (2006.01)
  *A61B 8/00* (2006.01)

(52) U.S. Cl.
  CPC .......... *A61B 5/1032* (2013.01); *A61B 5/14539* (2013.01); *A61B 5/4528* (2013.01); *A61B 5/4851* (2013.01); *A61B 5/6846* (2013.01); *A61B 5/4509* (2013.01); *A61B 8/58* (2013.01)

(56) References Cited

U.S. PATENT DOCUMENTS

| | | | |
|---|---|---|---|
| 4,066,082 A | 1/1978 | Arcan et al. | |
| 4,092,597 A | 5/1978 | Place | |
| 4,127,110 A | 11/1978 | Bullara | |
| 4,277,758 A | 7/1981 | Mishiro | |
| 4,480,485 A | 11/1984 | Bradshaw et al. | |
| 4,524,766 A | 6/1985 | Petersen | |
| 4,731,762 A | 3/1988 | Hanks | |
| 4,764,804 A | 8/1988 | Sahara et al. | |
| 4,848,164 A | 7/1989 | Quarve et al. | |
| 4,857,893 A | 8/1989 | Carrol | |
| 4,864,463 A | 9/1989 | Shkedi et al. | |
| 4,899,761 A | 2/1990 | Brown et al. | |
| 4,902,958 A | 2/1990 | Cook, II | |
| 4,920,279 A | 4/1990 | Charlet et al. | |
| 4,986,281 A | 1/1991 | Preves et al. | |
| 5,042,489 A | 8/1991 | Weiner et al. | |
| 5,119,676 A | 6/1992 | Bower et al. | |
| 5,456,724 A | 10/1995 | Yen et al. | |
| 5,470,354 A | 11/1995 | Hershberger et al. | |
| 5,650,571 A | 7/1997 | Freud et al. | |
| 5,683,396 A | 11/1997 | Tokish et al. | |
| 5,688,279 A | 11/1997 | McNulty et al. | |
| 5,733,292 A | 3/1998 | Gustilo et al. | |
| 5,871,018 A | 2/1999 | Delp et al. | |
| 5,900,592 A | 5/1999 | Sohns et al. | |
| 6,033,370 A | 3/2000 | Reinbold et al. | |
| 6,070,469 A | 6/2000 | Taniguchi et al. | |
| 6,072,784 A | 6/2000 | Agrawal et al. | |
| 6,159,611 A | 12/2000 | Lee et al. | |
| 6,165,142 A | 12/2000 | Bar | |
| 6,245,109 B1 | 6/2001 | Mendes et al. | |
| 6,425,920 B1 | 7/2002 | Hamada | |
| 6,429,585 B1 | 8/2002 | Kitazume et al. | |
| 6,443,891 B1 | 9/2002 | Grevious | |
| 6,447,448 B1 | 9/2002 | Ishikawa et al. | |
| 6,583,630 B2 | 6/2003 | Mendes et al. | |
| 6,621,278 B2 | 9/2003 | Ariav | |
| 6,689,999 B2 * | 2/2004 | Haines ............... | G01J 1/32 250/205 |
| 6,739,068 B1 | 5/2004 | Rinner | |
| 6,796,988 B2 | 9/2004 | Melkent et al. | |
| 6,856,141 B2 | 2/2005 | Ariav | |
| 6,993,393 B2 | 1/2006 | Von Arx et al. | |
| 7,035,077 B2 | 4/2006 | Brendel | |
| 7,080,554 B2 | 7/2006 | Ariav et al. | |
| 7,097,662 B2 | 8/2006 | Evans, III et al. | |
| 7,153,281 B2 | 12/2006 | Holmes | |
| 7,173,749 B2 | 2/2007 | Maleki et al. | |
| 7,195,645 B2 | 3/2007 | Disilvestro et al. | |
| 7,195,654 B2 | 3/2007 | Jackson et al. | |
| 7,215,599 B2 | 5/2007 | Nishimori et al. | |
| 7,283,867 B2 | 10/2007 | Strother et al. | |
| 7,347,817 B2 | 3/2008 | Glukhovsky et al. | |
| 7,378,916 B2 | 5/2008 | Oita et al. | |
| 7,384,403 B2 | 6/2008 | Sherman | |
| 7,396,336 B2 | 7/2008 | Orszulak et al. | |
| 7,412,897 B2 | 8/2008 | Crottet et al. | |
| 7,442,196 B2 | 10/2008 | Fisher et al. | |
| 7,454,972 B2 | 11/2008 | Heyman et al. | |
| 7,477,926 B2 | 1/2009 | McCombs | |
| 7,519,422 B2 | 4/2009 | Lippert et al. | |
| 7,559,951 B2 | 7/2009 | DiSilvestro et al. | |
| 7,575,602 B2 | 8/2009 | Amirouche et al. | |
| 7,578,821 B2 | 8/2009 | Fisher et al. | |
| 7,615,055 B2 | 11/2009 | DiSilvestro | |
| 7,630,774 B2 | 12/2009 | Karni et al. | |
| 7,632,283 B2 | 12/2009 | Heldreth | |
| 7,668,201 B2 | 2/2010 | Sharony et al. | |
| 7,725,288 B2 | 5/2010 | Boillot | |
| 7,769,947 B2 | 8/2010 | Ranganathan et al. | |
| 7,819,826 B2 | 10/2010 | Diederich et al. | |
| 7,918,887 B2 | 4/2011 | Roche | |
| 8,000,926 B2 | 8/2011 | Roche | |
| 8,098,544 B2 | 1/2012 | Roche | |
| 8,099,168 B2 | 1/2012 | Roche | |
| 8,141,437 B2 | 3/2012 | Amirouche et al. | |
| 8,167,823 B2 | 5/2012 | Nycz | |
| 8,169,185 B2 | 5/2012 | Partovi et al. | |
| 8,197,549 B2 | 6/2012 | Amirouche et al. | |
| 8,211,041 B2 | 7/2012 | Fisher et al. | |
| 8,270,253 B1 | 9/2012 | Roche | |
| 8,295,920 B2 | 10/2012 | Bouton et al. | |
| 8,372,147 B2 | 2/2013 | Roche | |
| 8,372,153 B2 | 2/2013 | Roche | |
| 8,421,642 B1 | 4/2013 | McIntosh et al. | |
| 8,444,654 B2 | 5/2013 | Roche | |
| 8,449,556 B2 | 5/2013 | Roche | |
| 8,494,805 B2 | 7/2013 | Roche | |
| 8,498,711 B2 | 7/2013 | Roche | |
| 8,720,270 B2 * | 5/2014 | Stein ................... | A61B 5/4528 73/379.01 |
| 2002/0029784 A1 | 3/2002 | Stark | |
| 2002/0049394 A1 | 4/2002 | Roy et al. | |
| 2003/0004518 A1 | 1/2003 | Perren et al. | |
| 2003/0036713 A1 | 2/2003 | Bouton et al. | |
| 2003/0036764 A1 | 2/2003 | Hamada | |
| 2003/0069644 A1 | 4/2003 | Kovacevic et al. | |
| 2003/0114898 A1 | 6/2003 | Von Arx et al. | |
| 2003/0187351 A1 | 10/2003 | Franck et al. | |
| 2004/0011365 A1 | 1/2004 | Govari et al. | |
| 2004/0064073 A1 | 4/2004 | Heldreth | |

(56) References Cited

U.S. PATENT DOCUMENTS

| | | |
|---|---|---|
| 2004/0131013 A1 | 7/2004 | Ise et al. |
| 2004/0152970 A1 | 8/2004 | Hunter et al. |
| 2004/0184351 A1 | 9/2004 | Nishimori et al. |
| 2004/0199168 A1 | 10/2004 | Bertagnoli et al. |
| 2004/0215079 A1 | 10/2004 | Omura et al. |
| 2005/0010299 A1 | 1/2005 | Disilvestro |
| 2005/0010302 A1 | 1/2005 | Dietz et al. |
| 2005/0020941 A1 | 1/2005 | Tarabichi |
| 2005/0119709 A1 | 6/2005 | Gauglitz et al. |
| 2005/0234555 A1 | 10/2005 | Sutton |
| 2005/0252294 A1 | 11/2005 | Ariav |
| 2005/0267485 A1 | 12/2005 | Cordes et al. |
| 2005/0273170 A1 | 12/2005 | Navarro et al. |
| 2006/0058798 A1 | 3/2006 | Roman et al. |
| 2006/0069436 A1 | 3/2006 | Sutton et al. |
| 2006/0132120 A1 | 6/2006 | Luber et al. |
| 2006/0161051 A1 | 7/2006 | Terrill-Grisoni et al. |
| 2006/0195109 A1 | 8/2006 | McGahan et al. |
| 2006/0206014 A1 | 9/2006 | Ariav |
| 2006/0232408 A1 | 10/2006 | Nycz |
| 2006/0241569 A1 | 10/2006 | DiSilvestro |
| 2006/0271112 A1 | 11/2006 | Martinson et al. |
| 2007/0129776 A1 | 6/2007 | Robins et al. |
| 2007/0219561 A1 | 9/2007 | Lavallee et al. |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0242652 A1 | 10/2007 | Dahlman et al. |
| 2007/0258674 A1 | 11/2007 | Wang |
| 2007/0272747 A1 | 11/2007 | Woods et al. |
| 2008/0082118 A1 | 4/2008 | Edidin et al. |
| 2008/0129486 A1 | 6/2008 | Jeckelmann et al. |
| 2008/0133016 A1 | 6/2008 | Heinz |
| 2008/0191584 A1 | 8/2008 | Malkin |
| 2008/0228195 A1 | 9/2008 | Von Jako et al. |
| 2008/0228231 A1 | 9/2008 | Raphael et al. |
| 2009/0005708 A1 | 1/2009 | Johanson |
| 2009/0015270 A1 | 1/2009 | Hayakawa et al. |
| 2009/0112207 A1 | 4/2009 | Walker et al. |
| 2009/0167719 A1 | 7/2009 | Woolley |
| 2010/0010494 A1 | 1/2010 | Quirno |
| 2010/0022874 A1 | 1/2010 | Wang et al. |
| 2010/0076505 A1 | 3/2010 | Borja |
| 2010/0100130 A1 | 4/2010 | Carl et al. |
| 2010/0151946 A1 | 6/2010 | Wilson et al. |
| 2010/0198067 A1 | 8/2010 | Mahfouz et al. |
| 2010/0198275 A1 | 8/2010 | Chana et al. |
| 2010/0204575 A1 | 8/2010 | Roche |
| 2010/0204955 A1 | 8/2010 | Roche |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0320973 A1 | 12/2010 | Nishida |
| 2010/0331633 A1 | 12/2010 | Stein |
| 2010/0331683 A1 | 12/2010 | Stein et al. |
| 2010/0331737 A1 | 12/2010 | Stein et al. |
| 2010/0331738 A1 | 12/2010 | Stein et al. |
| 2011/0029913 A1 | 2/2011 | Boillot |
| 2011/0032184 A1 | 2/2011 | Roche |
| 2011/0060220 A1 | 3/2011 | Roche |
| 2011/0092972 A1 | 4/2011 | Allen |
| 2011/0102455 A1 | 5/2011 | Temple |
| 2011/0160572 A1 | 6/2011 | McIntosh et al. |
| 2011/0160616 A1 | 6/2011 | Stein et al. |
| 2011/0160738 A1 | 6/2011 | McIntosh et al. |
| 2011/0257491 A1 | 10/2011 | Robertson et al. |
| 2012/0016362 A1 | 1/2012 | Heinrich et al. |
| 2012/0035868 A1 | 2/2012 | Roche |
| 2012/0152017 A1 | 6/2012 | Stein et al. |
| 2012/0209117 A1 | 8/2012 | Mozes |
| 2012/0277752 A1 | 11/2012 | Wasielewski |
| 2013/0225982 A1 | 8/2013 | McIntosh |

FOREIGN PATENT DOCUMENTS

| | | |
|---|---|---|
| CN | 101106958 | 1/2008 |
| CN | 101254103 | 9/2008 |
| CN | 101426453 | 5/2009 |
| CN | 101528122 | 9/2009 |
| CN | 101869504 | 10/2010 |
| CN | 101917918 | 12/2010 |
| EP | 1800097 B1 | 6/2007 |
| EP | 1800097 | 5/2008 |
| JP | 3267825 | 3/2002 |
| JP | 2007037361 | 2/2007 |
| WO | 03005877 | 1/2003 |
| WO | 2006098759 | 9/2006 |
| WO | 2006098759 A1 | 9/2006 |
| WO | 2008120215 | 10/2008 |
| WO | 2008120215 A2 | 10/2008 |

OTHER PUBLICATIONS

International Search Report for PCT/US2012/056743 dated Mar. 27, 2013, 4 pages.
International Search Report for PCT/US2012/056702 dated Feb. 27, 2013, 7 pages.
International Search Report for PCT/US2012/056758 dated Mar. 28, 2013, 5 pages.
International Search Report for PCT/US2012/056748 dated Mar. 27, 2013, 4 pages.
International Search Report for PCT/US2012/056740 dated Feb. 26, 2013, 4 pages.
International Search Report and Written Opinion for PCT/US2014/055521 dated Dec. 19, 2014.
International Search Report for PCT/US2012/056689 dated Feb. 25, 2013.
International Search Report for PCT/US2012/056743 dated Mar. 27, 2013.
International Search Report for PCT/US2012/056702 dated Feb. 27, 2013.
International Search Report for PCT/US2012/056758 dated Mar. 28, 2013.
International Search Report for PCT/US2012/056748 dated Mar. 27, 2013.
International Search Report for PCT/US2012/056740 dated Feb. 26, 2013.
E. Lou et al., Wireless Surgical Tools for Mechanical Measurements during Scoliosis Surgery; Proceedings of the 2005 IEEE, Engineering in Medicine and Biology 27th Annual Conference, Shanghai, China Sep. 1-4, 2005, pp. 7131-7134 (Sep. 2005). Sep. 1, 2005.
Miyazaki S et al: "Capacitive transducer for continuous measurement of vertical foot force", Medical and Biological Engineering and Computing, Springer, Heildelberg, DE, vol. 22, No. 4, Jul. 1, 1994, pp. 309-216, XP002133117 Jul. 1, 1984.

* cited by examiner

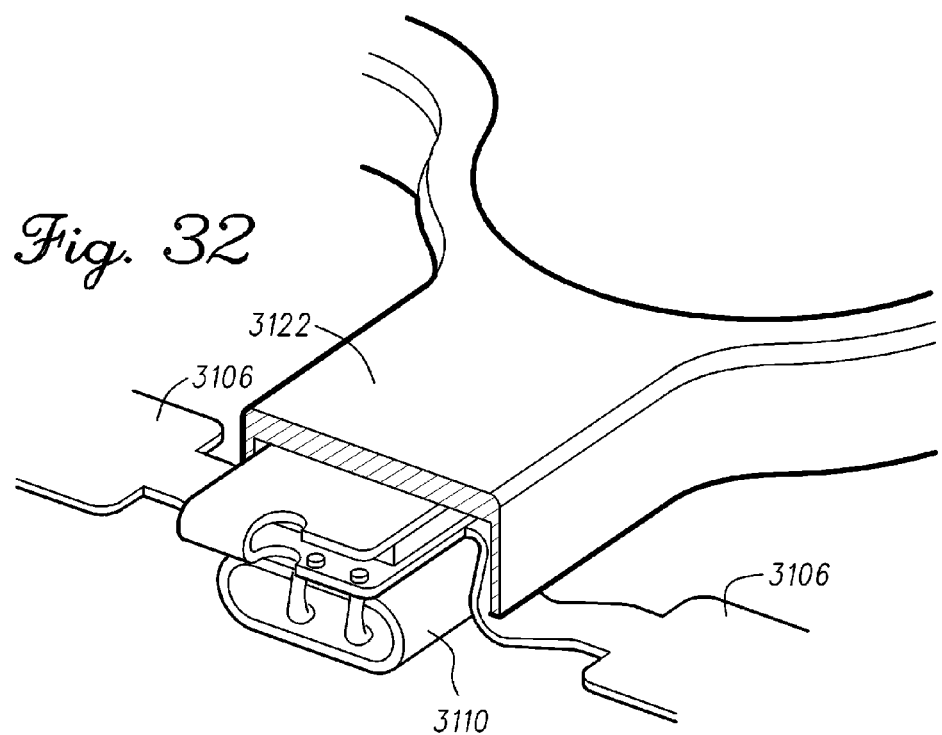
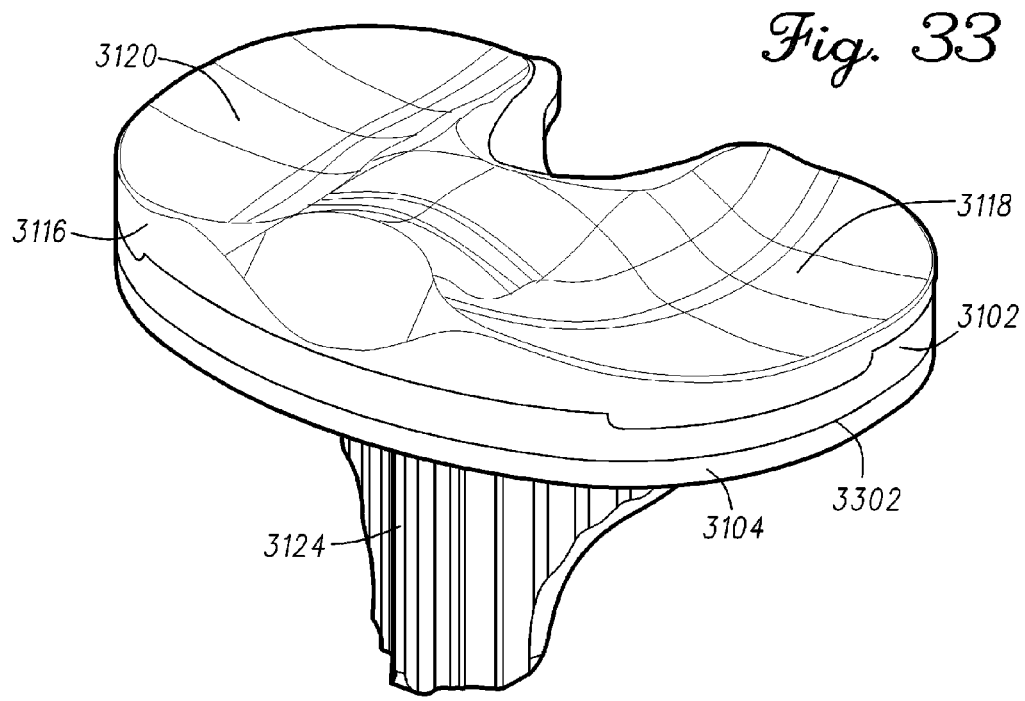

PROSTHETIC COMPONENT FOR MONITORING JOINT HEALTH

CROSS-REFERENCE TO RELATED APPLICATIONS

This application is a Continuation of application Ser. No. 13/406,519 filed on Feb. 27, 2012 that is a Continuation-In-Part and claims priority benefit of U.S. application Ser. No. 12/825,852 filed on Jun. 29, 2010 and further claims priority benefit of U.S. Provisional Patent Application No. 61/221,881 filed on Jun. 30, 2009, the entire contents of each application are hereby incorporated by reference. This application further claims the priority benefit of non-provisional application Ser. No. 12/826,349 filed on Jun. 29, 2010 and non-provisional application Ser. Nos. 13/242,277, and 13/242,662 filed on Sep. 23, 2011, the entire contents of each application are hereby incorporated by reference. This application further claims the priority benefit of U.S. provisional patent application Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009 which are hereby incorporated by reference.

FIELD

The present invention pertains generally to measurement of physical parameters, and particularly to, but not exclusively, medical electronic devices for high precision sensing.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 32 illustrates a cross-sectional view of a structure of the prosthetic component in accordance with an example embodiment;

FIG. 33 illustrates the prosthetic component and an insert in accordance with an example embodiment;

DETAILED DESCRIPTION

Figure 1:
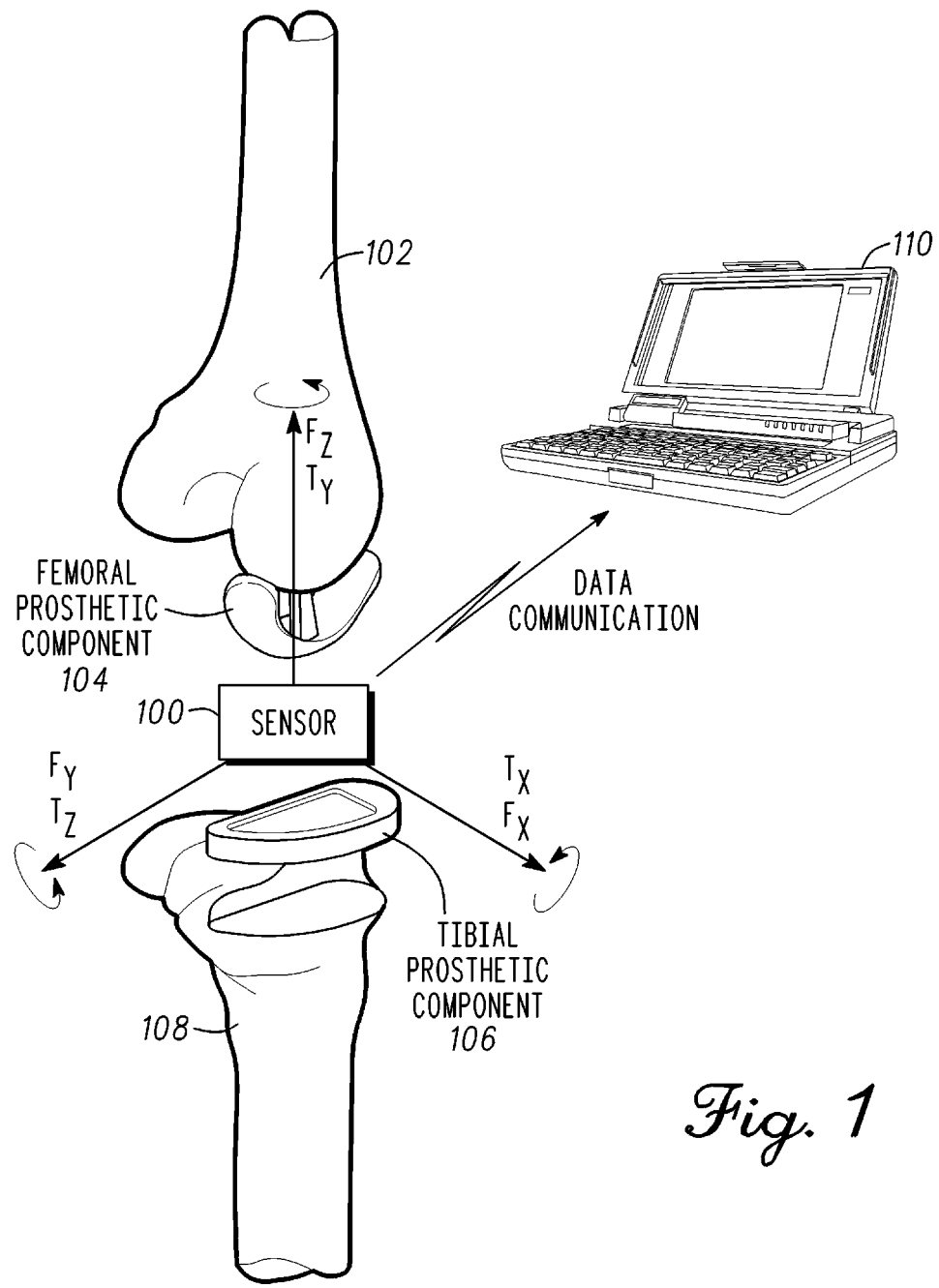
FIG. 1 illustrates a sensor placed in contact between a femur and a tibia for measuring a parameter in accordance with an example embodiment.

Embodiments of the invention are broadly directed to measurement of physical parameters, and more particularly, to fast-response circuitry that supports accurate measurement of small sensor changes.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

In all of the examples illustrated and discussed herein, any specific materials, such as temperatures, times, energies, and material properties for process steps or specific structure implementations should be interpreted to be illustrative only and non-limiting. Processes, techniques, apparatus, and materials as known by one of ordinary skill in the art may not be discussed in detail but are intended to be part of an enabling description where appropriate. It should also be noted that the word "coupled" used herein implies that elements may be directly coupled together or may be coupled through one or more intervening elements.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

In a first embodiment, an ultrasonic measurement system comprises one or more ultrasonic transducers, an ultrasonic waveguide, and a propagation tuned oscillator (PTO) or Phase Locked Loop (PLL). The ultrasonic measurement system in this embodiment employs a continuous mode (CM) of operation to evaluate propagation characteristics of continuous ultrasonic waves in the waveguide by way of closed-loop feedback to determine levels of applied forces on the waveguide.

In a second embodiment, an ultrasonic measurement system comprises one or more ultrasonic transducers, an ultrasonic waveguide, and a propagation tuned oscillator (PTO) or Phase Locked Loop (PLL). The ultrasonic measurement system in this embodiment employs a pulse mode (PM) of operation to evaluate propagation characteristics of pulsed ultrasonic waves in the waveguide by way of closed-loop feedback to determine levels of applied forces on the waveguide.

In a third embodiment, an ultrasonic measurement system comprises one or more ultrasonic transducers, an ultrasonic waveguide, and a propagation tuned oscillator (PTO) or Phase Locked Loop (PLL). The ultrasonic measurement system in this embodiment employs a pulse echo mode (PE) of operation to evaluate propagation characteristics of ultrasonic echo reflections in the waveguide by way of closed-loop feedback to determine levels of applied forces on the waveguide.

FIG. 1 is an illustration of a sensor 100 placed in contact between a femur 102 and a tibia 108 for measuring a parameter in accordance with an exemplary embodiment. In general, a sensor 100 is placed in contact with or in proximity to the muscular-skeletal system to measure a parameter. In a non-limiting example, sensor 100 is used to measure a parameter of a muscular-skeletal system during a procedure such as an installation of an artificial joint. Embodiments of sensor 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Sensor 100 can provide implant status data to the orthopedic manufacturers and surgeons. Moreover, data generated by direct measurement of the implanted joint itself would greatly improve the knowledge of implanted joint operation and joint wear thereby leading to improved design and materials.

In at least one exemplary embodiment, an energy pulse is directed within one or more waveguides in sensor 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

Sensor 100 can be size constrained by form factor requirements of fitting within a region the muscular-skeletal system or a component such as a tool, equipment, or artificial joint. In a non-limiting example, sensor 100 is used to measure load and balance of an installed artificial knee joint. A knee prosthesis comprises a femoral prosthetic component 104, an insert, and a tibial prosthetic component 106. A distal end of femur 102 is prepared and receives femoral prosthetic component 104. Femoral prosthetic component 104 typically has two condyle surfaces that mimic a natural femur. As shown, femoral prosthetic component 104 has single condyle surface being coupled to femur 102. Femoral prosthetic component 104 is typically made of a metal or metal alloy.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. The insert is fitted between femoral prosthetic component 104 and tibial prosthetic component 106. The insert has at least one bearing surface that is in contact with at least condyle surface of femoral prosthetic component 104. The condyle surface can move in relation to the bearing surface of the insert such that the lower leg can rotate under load. The insert is typically made of a high wear plastic material that minimizes friction.

In a knee joint replacement process, the surgeon affixes femoral prosthetic component 104 to the femur 102 and tibial prosthetic component 106 to tibia 108. The tibial prosthetic component 106 can include a tray or plate affixed to the planarized proximal end of the tibia 108. Sensor 100 is placed between a condyle surface of femoral prosthetic component 104 and a major surface of tibial prosthetic component 106. The condyle surface contacts a major surface of sensor 100. The major surface of sensor 100 approximates a surface of the insert. Tibial prosthetic component 106 can include a cavity or tray on the major surface that receives and retains sensor 100 during a measurement process. Tibial prosthetic component 106 and sensor 100 has a combined thickness that represents a combined thickness of tibial prosthetic component 106 and a final (or chronic) insert of the knee joint.

In one embodiment, two sensors 100 are fitted into two separate cavities, the cavities are within a trial insert (that may also be referred to as the tibial insert, rather than the tibial component itself) that is held in position by tibial component 106. One or two sensors 100 may be inserted between femoral prosthetic component 104 and tibial prosthetic component 106. Each sensor is independent and each measures a respective condyle of femur 102. Separate sensors also accommodate a situation where a single condyle is repaired and only a single sensor is used. Alternatively, the electronics can be shared between two sensors to lower cost and complexity of the system. The shared electronics can multiplex between each sensor module to take measurements when appropriate. Measurements taken by sensor 100 aid the surgeon in modifying the absolute loading on each condyle and the balance between condyles. Although shown for a knee implant, sensor 100 can be used to measure other orthopedic joints such as the spine, hip, shoulder, elbow, ankle, wrist, interphalangeal joint, metatarsophalangeal joint, metacarpophalangeal joints, and others. Alternatively, sensor 100 can also be adapted to orthopedic tools to provide measurements.

The prosthesis incorporating sensor 100 emulates the function of a natural knee joint. Sensor 100 can measure loads or other parameters at various points throughout the range of motion. Data from sensor 100 is transmitted to a receiving station 110 via wired or wireless communications. In a first embodiment, sensor 100 is a disposable system. Sensor 100 can be disposed of after using sensor 100 to optimally fit the joint implant. Sensor 100 is a low cost disposable system that reduces capital costs, operating costs, facilitates rapid adoption of quantitative measurement, and initiates evidentiary based orthopedic medicine. In a second embodiment, a methodology can be put in place to clean and sterilize sensor 100 for reuse. In a third embodiment, sensor 100 can be incorporated in a tool instead of being a component of the replacement joint. The tool can be disposable or be cleaned and sterilized for reuse. In a fourth embodiment, sensor 100 can be a permanent component of the replacement joint. Sensor 100 can be used to provide both short term and long term post-operative data on the implanted joint. In a fifth embodiment, sensor 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of sensor 100 to an appropriate authority.

In an intra-operative example, sensor 100 can measure forces (Fx, Fy, Fz) with corresponding locations and torques (e.g. Tx, Ty, and Tz) on the femoral prosthetic component 104 and the tibial prosthetic component 106. The measured force and torque data is transmitted to receiving station 110 to provide real-time visualization for assisting the surgeon in identifying any adjustments needed to achieve optimal joint pressure and balancing. The data has substantial value in determining ranges of load and alignment tolerances required to minimize rework and maximize patient function and longevity of the joint.

As mentioned previously, sensor 100 can be used for other joint surgeries; it is not limited to knee replacement implant or implants. Moreover, sensor 100 is not limited to trial measurements. Sensor 100 can be incorporated into the final joint system to provide data post-operatively to determine if the implanted joint is functioning correctly. Early determination of a problem using sensor 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, sensor 100 can be shaped such that it can be placed or engaged or affixed to or within load bearing surfaces used in many orthopedic applications (or used in any orthopedic application) related to the musculoskeletal system, joints, and tools associated therewith. Sensor 100 can provide information on a combination of one or more performance parameters of interest such as wear, stress, kinematics, kinetics, fixation strength, ligament balance, anatomical fit and balance.

Figure 2:
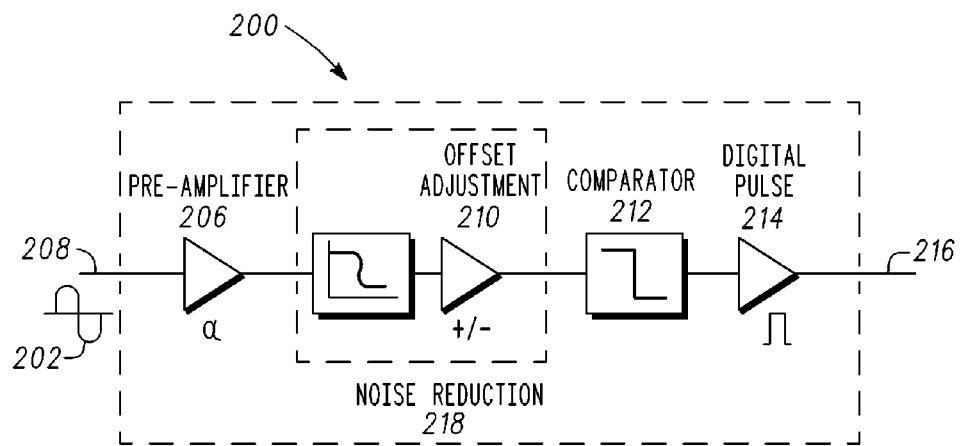
FIG. 2 illustrates a block diagram of an zero-crossing receiver in accordance with an example embodiment.

FIG. 2 is a block diagram of a zero-crossing receiver 200 in accordance with one embodiment. In a first embodiment, the zero-crossing receiver 200 is provided to detect transition states of energy waves, such as the transition of each energy wave through a mid-point of a symmetrical or cyclical waveform. This enables capturing of parameters including, but not limited to, transit time, phase, or frequency of the energy waves. The receiver rapidly responds to a signal transition and outputs a digital pulse that is consistent with the energy wave transition characteristics and with minimal delay. The zero-crossing receiver 200 further discriminates between noise and the energy waves of interest, including very low level waves by way of adjustable levels of noise reduction. A noise reduction section 218 comprises a filtering stage and an offset adjustment stage to perform noise suppression accurately over a wide range of amplitudes including low level waves.

In a second embodiment, a zero-crossing receiver is provided to convert an incoming symmetrical, cyclical, or sine wave to a square or rectangular digital pulse sequence with superior performance for very low level input signals. The digital pulse sequence represents pulse timing intervals that are consistent with the energy wave transition times. The zero-crossing receiver is coupled with a sensing assembly to generate the digital pulse sequence responsive to evaluating transitions of the incoming sine wave. This digital pulse sequence conveys timing information related to parameters of interest, such as applied forces, associated with the physical changes in the sensing assembly.

In a third embodiment, the integrated zero-crossing receiver is incorporated within a propagation tuned oscillator (PTO) to maintain positive closed-loop feedback when operating in a continuous wave mode or pulse-loop mode. The integrated edge zero-crossing receiver is electrically integrated with the PTO by multiplexing input and output circuitry to achieve ultra low-power and small compact size. Electrical components of the PTO are integrated with components of the zero-crossing receiver to assure adequate sensitivity to low-level signals.

In one embodiment, low power zero-crossing receiver 200 can be integrated with other circuitry of the propagation tuned oscillator to further improve performance at low signal levels. The zero-crossing receiver 200 comprises a preamplifier 206, a filter 208, an offset adjustment circuitry 210, a comparator 212, and a digital pulse circuit 214. The filter 208 and offset adjustment circuitry 210 constitute a noise reduction section 218 as will be explained ahead. The zero-crossing receiver 200 can be implemented in discrete analog components, digital components or combination thereof. The integrated zero-crossing receiver 200 practices measurement methods that detect the midpoint of energy waves at specified locations, and under specified conditions, to enable capturing parameters including, but not limited to, transit time, phase, or frequency of energy waves. A brief description of the method of operation is as follows.

An incoming energy wave 202 is coupled from an electrical connection, antenna, or transducer to an input 204 of zero-crossing receiver 200. Input 204 of zero-crossing receiver 200 is coupled to pre-amplifier 206 to amplify the incoming energy wave 202. The amplified signal is filtered by filter 208. Filter 208 is coupled to an output of pre-amplifier 206 and an input of offset adjustment circuitry 210. In one configuration, filter 208 is a low-pass filter to remove high frequency components above the incoming energy wave 202 bandwidth. In another arrangement, the filter is a band-pass filter with a pass-band corresponding to the bandwidth of the incoming energy wave 202. It is not however limited to either arrangement. The offset of the filtered amplified wave is adjusted by offset adjustment circuitry 210. An input of comparator 212 is coupled to an output of offset adjustment circuitry 210. Comparator 212 monitors the amplified waveforms and triggers digital pulse circuitry 214 whenever the preset trigger level is detected. Digital pulse circuit 214 has an input coupled to the output of comparator 212 and an output for providing digital pulse 216. The digital pulse 216 can be further coupled to signal processing circuitry, as will be explained ahead.

In a preferred embodiment, the electronic components are operatively coupled together as blocks of integrated circuits. As will be shown ahead, this integrated arrangement performs its specific functions efficiently with a minimum number of components. This is because the circuit components are partitioned between structures within an integrated circuit and discrete components, as well as innovative partitioning of analog and digital functions, to achieve the required performance with a minimum number of components and minimum power consumption.

Figure 3:
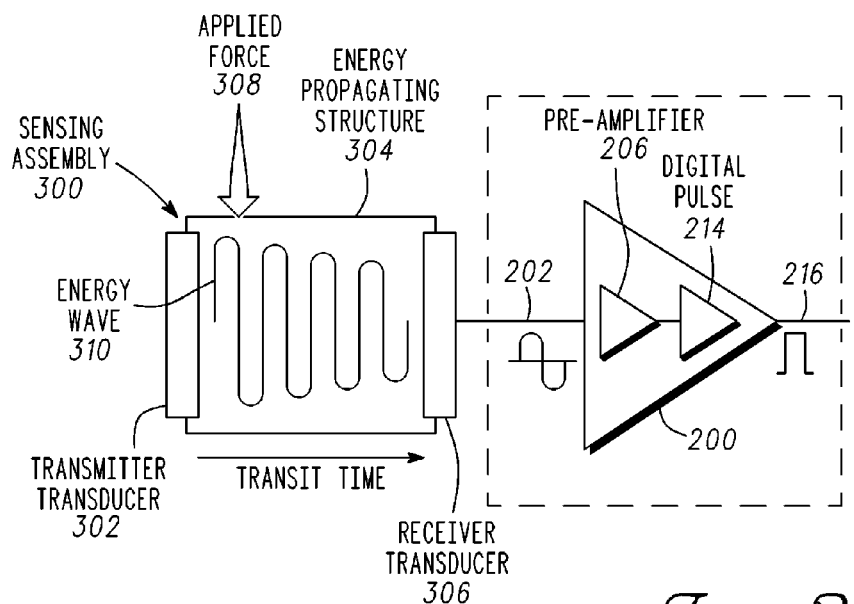
FIG. 3 illustrates a block diagram of the integrated zero-crossing receiver coupled to a sensing assembly in accordance with an example embodiment.

FIG. 3 illustrates a block diagram of the integrated zero-crossing receiver 200 coupled to a sensing assembly 300 in accordance with an exemplary embodiment. The pre-amplifier 206 and the digital pulse circuit 214 are shown for reference and discussion. In one embodiment, sensing assembly 300 comprises a transmitter transducer 302, an energy propagating structure (or medium) 304, and a receiver transducer 306. As will be explained further hereinbelow, the sensing assembly 300 in one embodiment is part of a sensory device that measures a parameter such as force, pressure, or load. In a non-limiting example, an external parameter such as an applied force 308 affects the sensing assembly 200. As shown, applied force 308 modifies propagating structure 304 dimensionally. In general, the sensing assembly 300 conveys one or more parameters of interest such as distance, force, weight, strain, pressure, wear, vibration, viscosity, density, direction, and displacement related to a change in energy propagating structure 304. An example is measuring loading applied by a joint of the muscular-skeletal system as disclosed above using sensing assembly 300 between the bones of the joint.

A transducer driver circuit (not shown) drives the transmitter transducer 302 of the sensing assembly 300 to produce energy waves 310 that are directed into the energy propagating structure 304. Changes in the energy propagating medium 304 due to an applied parameter such as applied forces 308 change the frequency, phase, and transit time of energy waves 310 (or pulses). In one embodiment, applied forces 308 affect the length of propagating structure 304 in a direction of a path of propagation of energy waves 310. The zero-crossing receiver 200 is coupled to the receiver transducer 306 to detect zero-crossings of the reproduced energy wave 202.

Upon detecting a zero-crossing digital pulse circuit 214 is triggered to output a pulse 216. The timing of the digital pulse 216 conveys the parameters of interest (e.g., distance, force weight, strain, pressure, wear, vibration, viscosity, density, direction, displacement, etc.).

Measurement methods that rely on such propagation of energy waves 310 or pulses of energy waves are required to achieve highly accurate and controlled detection of energy waves or pulses. Moreover, pulses of energy waves may contain multiple energy waves with complex waveforms therein leading to potential ambiguity of detection. In particular, directing energy waves 310 into the energy propagating structure 304 can generate interference patterns caused by nulls and resonances of the waveguide, as well as characteristics of the generated energy waves 310. These interference patterns can multiply excited waveforms that result in distortion of the edges of the original energy wave.

Briefly referring back to FIG. 2, to reliably detect the arrival of a pulse of energy waves, the zero-crossing receiver 200 leverages noise reduction section 218 that incorporates two forms of noise reduction. Frequencies above the operating frequencies for physical measurements of the parameters of interest are attenuated with the filter 208. In addition, the offset level of the incoming waveform is adjusted by the offset adjustment 210 to optimize the voltage level at which the comparator 212 triggers an output pulse. This is more reliable than amplifying the incoming waveform because it does not add additional amplification of noise present on the input. The combination of rapid response to the arrival of incoming symmetrical, cyclical, or sine waves with adjustable levels of noise reduction achieves reliable zero-crossing detection by way of the ultra low power zero-crossing receiver 200 with superior performance for very low level signals.

There are a wide range of applications for compact measurement modules or devices having ultra low power circuitry that enables the design and construction of highly performing measurement modules or devices that can be tailored to fit a wide range of nonmedical and medical applications. Applications for highly compact measurement modules or devices may include, but are not limited to, disposable modules or devices as well as reusable modules or devices and modules or devices for long term use. In addition to nonmedical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 4:
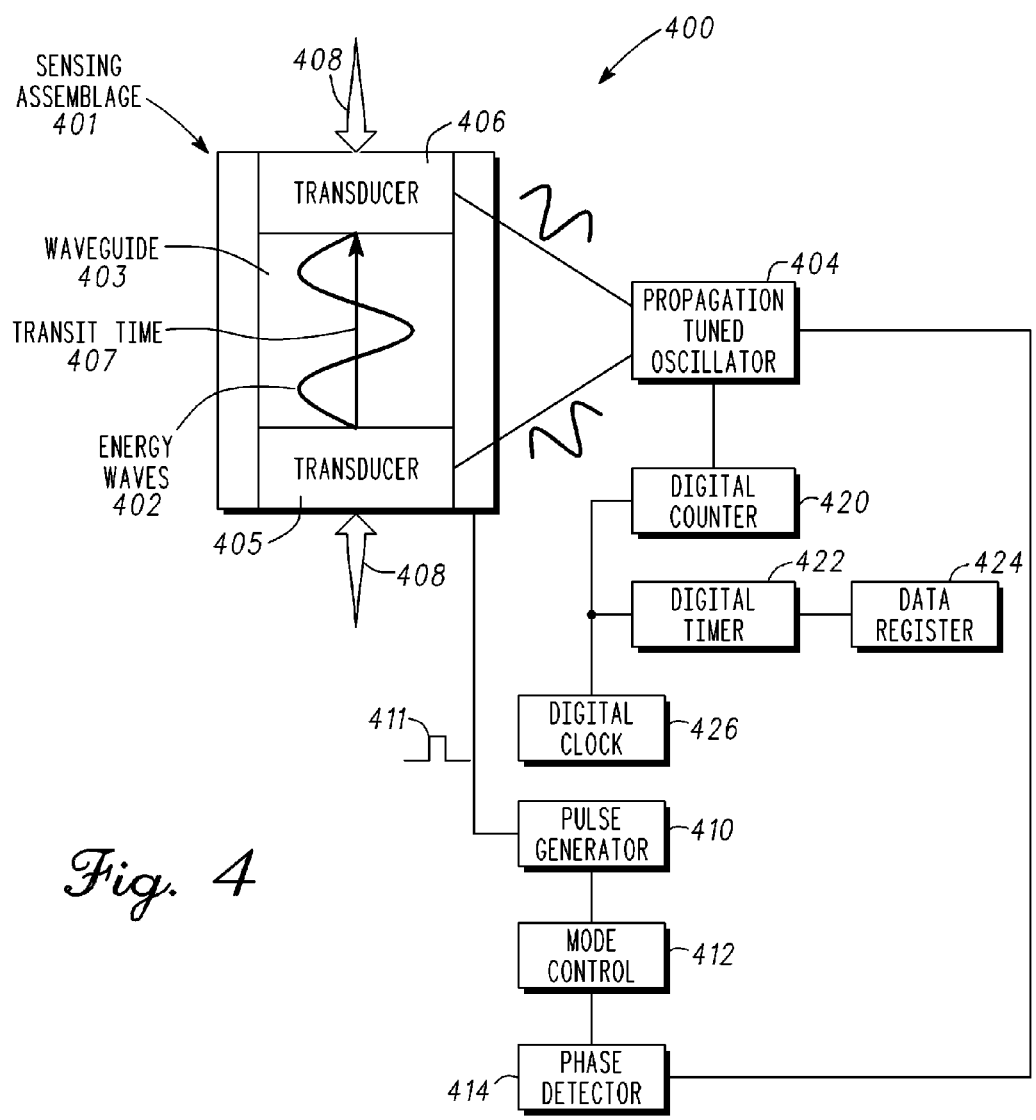
FIG. 4 illustrates a propagation tuned oscillator (PTO) incorporating a zero-crossing receiver or an edge detect receiver to maintain positive closed-loop feedback in accordance with an example embodiment.

FIG. 4 is an exemplary block diagram 400 of a propagation tuned oscillator (PTO) 404 to maintain positive closed-loop feedback in accordance with an exemplary embodiment. The measurement system includes a sensing assemblage 401 and propagation tuned oscillator (PTO) 404 that detects energy waves 402 in one or more waveguides 403 of the sensing assemblage 401. In one embodiment, energy waves 402 are ultrasound waves. A pulse 411 is generated in response to the detection of energy waves 402 to initiate a propagation of a new energy wave in waveguide 403. It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

The sensing assemblage 401 comprises transducer 405, transducer 406, and a waveguide 403 (or energy propagating structure). In a non-limiting example, sensing assemblage 401 is affixed to load bearing or contacting surfaces 408. External forces applied to the contacting surfaces 408 compress the waveguide 403 and change the length of the waveguide 403. Under compression, transducers 405 and 406 will also be move closer together. The change in distance affects the transit time 407 of energy waves 402 transmitted and received between transducers 405 and 406. The propagation tuned oscillator 404 in response to these physical changes will detect each energy wave sooner (e.g. shorter transit time) and initiate the propagation of new energy waves associated with the shorter transit time. As will be explained below, this is accomplished by way of PTO 404 in conjunction with the pulse generator 410, the mode control 412, and the phase detector 414.

Notably, changes in the waveguide 403 (energy propagating structure or structures) alter the propagation properties of the medium of propagation (e.g. transit time 407). The energy wave can be a continuous wave or a pulsed energy wave. A pulsed energy wave approach reduces power dissipation allowing for a temporary power source such as a battery or capacitor to power the system during the course of operation. In at least one exemplary embodiment, a continuous wave energy wave or a pulsed energy wave is provided by transducer 405 to a first surface of waveguide 403. Transducer 405 generates energy waves 402 that are coupled into waveguide 403. In a non-limiting example, transducer 405 is a piezo-electric device capable of transmitting and receiving acoustic signals in the ultrasonic frequency range.

Transducer 406 is coupled to a second surface of waveguide 403 to receive the propagated pulsed signal and generates a corresponding electrical signal. The electrical signal output by transducer 406 is coupled to phase detector 414. In general, phase detector 414 is a detection circuit that compares the timing of a selected point on the waveform of the detected energy wave with respect to the timing of the same point on the waveform of other propagated energy waves. In a first embodiment, phase detector 414 can be a zero-crossing receiver. In a second embodiment, phase detector 414 can be an edge-detect receiver. In a third embodiment, phase detector 414 can be a phase locked loop. In the example where sensing assemblage 401 is compressed, the detection of the propagated energy waves 402 occurs earlier (due to the length/distance reduction of waveguide 403) than a signal prior to external forces being applied to contacting surfaces. Pulse generator 410 generates a new pulse in response to detection of the propagated energy waves 402 by phase detector 414. The new pulse is provided to transducer 405 to initiate a new energy wave sequence. Thus, each energy wave sequence is an individual event of energy wave propagation, energy wave detection, and energy wave emission that maintains energy waves 402 propagating in waveguide 403.

The transit time 407 of a propagated energy wave is the time it takes an energy wave to propagate from the first surface of waveguide 403 to the second surface. There is delay associated with each circuit described above. Typically, the total delay of the circuitry is significantly less than the propagation time of an energy wave through waveguide 403. In addition, under equilibrium conditions variations in circuit delay are minimal. Multiple pulse to pulse timings can be used to generate an average time period when change in external forces occur relatively slowly in relation to the pulsed signal propagation time such as in a physiologic or mechanical system. The digital counter 420 in conjunction with electronic components counts the number of propagated energy waves to determine a corresponding change in the length of the waveguide 403. These changes in length change in direct proportion to the external force thus enabling the conversion of changes in parameter or parameters of interest into electrical signals.

The block diagram 400 further includes counting and timing circuitry. More specifically, the timing, counting, and clock circuitry comprises a digital timer 420, a digital timer 422, a digital clock 426, and a data register 424. The digital clock 426 provides a clock signal to digital counter 420 and digital timer 422 during a measurement sequence. The digital counter 420 is coupled to the propagation tuned oscillator 404. Digital timer 422 is coupled to data register 424. Digital timer 420, digital timer, 422, digital clock 426 and data register 424 capture transit time 407 of energy waves 402 emitted by ultrasound resonator or transducer 405, propagated through waveguide 403, and detected by or ultrasound resonator or transducer 405 or 406 depending on the mode of the measurement of the physical parameters of interest applied to surfaces 408. The operation of the timing and counting circuitry is disclosed in more detail hereinbelow.

The measurement data can be analyzed to achieve accurate, repeatable, high precision and high resolution measurements. This method enables the setting of the level of precision or resolution of captured data to optimize trade-offs between measurement resolution versus frequency, including the bandwidth of the sensing and data processing operations, thus enabling a sensing module or device to operate at its optimal operating point without compromising resolution of the measurements. This is achieved by the accumulation of multiple cycles of excitation and transit time instead of averaging transit time of multiple individual excitation and transit cycles. The result is accurate, repeatable, high precision and high resolution measurements of parameters of interest in physical systems.

In at least one exemplary embodiment, propagation tuned oscillator 404 in conjunction with one or more sensing assemblages 401 are used to take measurements on a muscular-skeletal system. In a non-limiting example, sensing assemblage 401 is placed between a femoral prosthetic component and tibial prosthetic component to provide measured load information that aids in the installation of an artificial knee joint. Sensing assemblage 401 can also be a permanent component or a muscular-skeletal joint or artificial muscular-skeletal joint to monitor joint function. The measurements can be made in extension and in flexion. In the example, assemblage 401 is used to measure the condyle loading to determine if it falls within a predetermined range and location. Based on the measurement, the surgeon can select the thickness of the insert such that the measured loading and incidence with the final insert in place will fall within the predetermined range. Soft tissue tensioning can be used by a surgeon to further optimize the force or pressure. Similarly, two assemblages 401 can be used to measure both condyles simultaneously or multiplexed. The difference in loading (e.g. balance) between condyles can be measured. Soft tissue tensioning can be used to reduce the force on the condyle having the higher measured loading to reduce the measured pressure difference between condyles.

One method of operation holds the number of energy waves propagating through waveguide 403 as a constant integer number. A time period of an energy wave corresponds to energy wave periodicity. A stable time period is one in which the time period changes very little over a number of energy waves. This occurs when conditions that affect sensing assemblage 401 stay consistent or constant. Holding the number of energy waves propagating through waveguide 403 to an integer number is a constraint that forces a change in the time between pulses when the length of waveguide 403 changes. The resulting change in time period of each energy wave corresponds to a change in aggregate energy wave time period that is captured using digital counter 420 as a measurement of changes in external forces or conditions applied to contacting surfaces 408.

A further method of operation according to one embodiment is described hereinbelow for energy waves 402 propagating from transducer 405 and received by transducer 406. In at least one exemplary embodiment, energy waves 402 are an ultrasonic energy wave. Transducers 405 and 406 are piezoelectric resonator transducers. Although not described, wave propagation can occur in the opposite direction being initiated by transducer 406 and received by transducer 405. Furthermore, detecting ultrasound resonator transducer 406 can be a separate ultrasound resonator as shown or transducer 405 can be used solely depending on the selected mode of propagation (e.g. reflective sensing). Changes in external forces or conditions applied to contacting surfaces 408 affect the propagation characteristics of waveguide 403 and alter transit time 407. As mentioned previously, propagation tuned oscillator 404 holds constant an integer number of energy waves 402 propagating through waveguide 403 (e.g. an integer number of pulsed energy wave time periods) thereby controlling the repetition rate. As noted above, once PTO 404 stabilizes, the digital counter 420 digitizes the repetition rate of pulsed energy waves, for example, by way of edge-detection, as will be explained hereinbelow in more detail.

In an alternate embodiment, the repetition rate of pulsed energy waves 402 emitted by transducer 405 can be controlled by pulse generator 410. The operation remains similar where the parameter to be measured corresponds to the measurement of the transit time 407 of pulsed energy waves 402 within waveguide 403. It should be noted that an individual ultrasonic pulse can comprise one or more energy waves with a damping wave shape. The energy wave shape is determined by the electrical and mechanical parameters of pulse generator 410, interface material or materials, where required, and ultrasound resonator or transducer 405. The frequency of the energy waves within individual pulses is determined by the response of the emitting ultrasound resonator 404 to excitation by an electrical pulse 411. The mode of the propagation of the pulsed energy waves 402 through waveguide 403 is controlled by mode control circuitry 412 (e.g., reflectance or uni-directional). The detecting ultrasound resonator or transducer may either be a separate ultrasound resonator or transducer 406 or the emitting resonator or transducer 405 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound energy waves within a waveguide of known length can be achieved by modulating the repetition rate of the ultrasound energy waves as a function of changes in distance or velocity through the medium of propagation, or a combination of changes in distance and velocity, caused by changes in the parameter or parameters of interest.

Measurement methods that rely on the propagation of energy waves, or energy waves within energy pulses, may require the detection of a specific point of energy waves at specified locations, or under specified conditions, to enable capturing parameters including, but not limited to, transit time, phase, or frequency of the energy waves. Measurement of the changes in the physical length of individual ultrasound waveguides may be made in several modes. Each assemblage of one or two ultrasound resonators or transducers combined with an ultrasound waveguide may be controlled to operate in six different modes. This includes two wave shape modes: continuous wave or pulsed waves, and three propagation modes: reflectance, unidirectional, and bi-directional propagation of the ultrasound wave. The resolution of these measurements can be further enhanced by advanced processing of the measurement data to enable optimization of the trade-offs between measurement resolution versus length of the waveguide, frequency of the ultrasound waves, and the bandwidth of the sensing and data capture operations, thus achieving an optimal operating point for a sensing module or device.

Measurement by propagation tuned oscillator 404 and sensing assemblage 401 enables high sensitivity and high signal-to-noise ratio. The time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Figure 17:
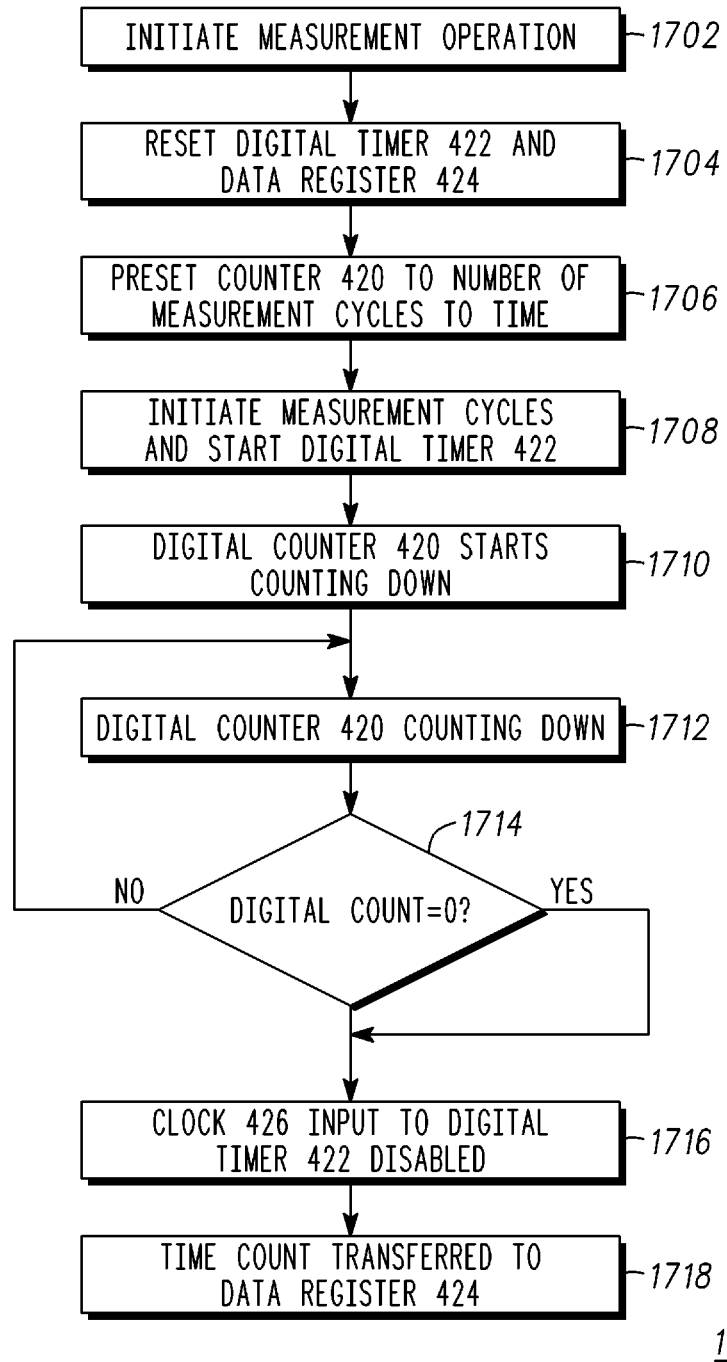
FIG. 17 illustrates a simplified flow chart of method steps for high precision processing and measurement data in accordance with an example embodiment.

Referring to FIG. 17, a simplified flow chart 1700 of method steps for high precision processing and measurement data is shown in accordance with an exemplary embodiment. The method 1700 can be practiced with more or less than the steps shown, and is not limited to the order of steps shown. The method steps correspond to FIG. 4 to be practiced with the aforementioned components or any other components suitable for such processing, for example, electrical circuitry to control the emission of energy pulses or waves and to capture the repetition rate of the energy pulses or frequency of the energy waves propagating through the elastic energy propagating structure or medium.

In a step 1702, the process initiates a measurement operation. In a step 1704, a known state is established by resetting digital timer 422 and data register 424. In a step 1706, digital counter 420 is preset to the number of measurement cycles over which measurements will be taken and collected. In a step 1708, the measurement cycle is initiated and a clock output of digital clock 426 is enabled. A clock signal from digital clock 426 is provided to both digital counter 420 and digital timer 422. An elapsed time is counted by digital timer 420 based on the frequency of the clock signal output by digital clock 426. In a step 1710, digital timer 422 begins tracking the elapsed time. Simultaneously, digital counter 420 starts decrementing a count after each measurement sequence. In one embodiment, digital counter 420 is decremented as each energy wave propagates through waveguide 403 and is detected by transducer 406. Digital counter 420 counts down until the preset number of measurement cycles has been completed. In a step 1712, energy wave propagation is sustained by propagation tuned oscillator 404, as digital counter 420 is decremented by the detection of a propagated energy wave. In a step 1714, energy wave detection, emission, and propagation continue while the count in digital counter 420 is greater than zero. In a step 1716, the clock input of digital timer 422 is disabled upon reaching a zero count on digital counter 420 thus preventing digital counter 420 and digital timer 422 from being clocked. In one embodiment, the preset number of measurement cycles provided to digital counter 420 is divided by the elapsed time measured by digital timer 422 to calculate a frequency of propagated energy waves. Conversely, the number can be calculated as a transit time by dividing the elapsed time from digital timer 422 by the preset number of measurement cycles. Finally, in a step 1718, the resulting value is transferred to register 424. The number in data register 424 can be wirelessly transmitted to a display and database. The data from data register 424 can be correlated to a parameter being measured. The parameter such as a force or load is applied to the propagation medium (e.g. waveguide 403) such that parameter changes also change the frequency or transit time calculation of the measurement. A relationship between the material characteristics of the propagation medium and the parameter is used with the measurement value (e.g. frequency, transit time, phase) to calculate a parameter value.

The method 1700 practiced by the example assemblage of FIG. 4, and by way of the digital counter 420, digital timer 422, digital clock 426 and associated electronic circuitry analyzes the digitized measurement data according to operating point conditions. In particular, these components accumulate multiple digitized data values to improve the level of resolution of measurement of changes in length or other aspect of an elastic energy propagating structure or medium that can alter the transit time of energy pulses or waves propagating within the elastic energy propagating structure or medium. The digitized data is summed by controlling the digital counter 420 to run through multiple measurement cycles, each cycle having excitation and transit phases such that there is not lag between successive measurement cycles, and capturing the total elapsed time. The counter is sized to count the total elapsed time of as many measurement cycles as required to achieve the required resolution without overflowing its accumulation capacity and without compromising the resolution of the least significant bit of the counter. The digitized measurement of the total elapsed transit time is subsequently divided by the number of measurement cycles to estimate the time of the individual measurement cycles and thus the transit time of individual cycles of excitation, propagation through the elastic energy propagating structure or medium, and detection of energy pulses or waves. Accurate estimates of changes in the transit time of the energy pulses or waves through the elastic energy propagating structure or medium are captured as elapsed times for excitation and detection of the energy pulses or waves are fixed.

Summing individual measurements before dividing to estimate the average measurement value data values produces superior results to averaging the same number of samples. The resolution of count data collected from a digital counter is limited by the resolution of the least-significant-bit in the counter. Capturing a series of counts and averaging them does not produce greater precision than this least-significant-bit, that is the precision of a single count. Averaging does reduce the randomness of the final estimate if there is random variation between individual measurements. Summing the counts of a large number of measurement cycles to obtain a cumulative count then calculating the average over the entire measurement period improves the precision of the measurement by interpolating the component of the measurement that is less than the least significant bit of the counter. The precision gained by this procedure is on the order of the resolution of the least-significant-bit of the counter divided by the number of measurement cycles summed.

The size of the digital counter and the number of measurement cycles accumulated may be greater than the required level of resolution. This not only assures performance that achieves the level of resolution required, but also averages random component within individual counts producing highly repeatable measurements that reliably meet the required level of resolution.

The number of measurement cycles is greater than the required level of resolution. This not only assures performance that achieves the level of resolution required, but also averages any random component within individual counts producing highly repeatable measurements that reliably meet the required level of resolution.

Figure 5:
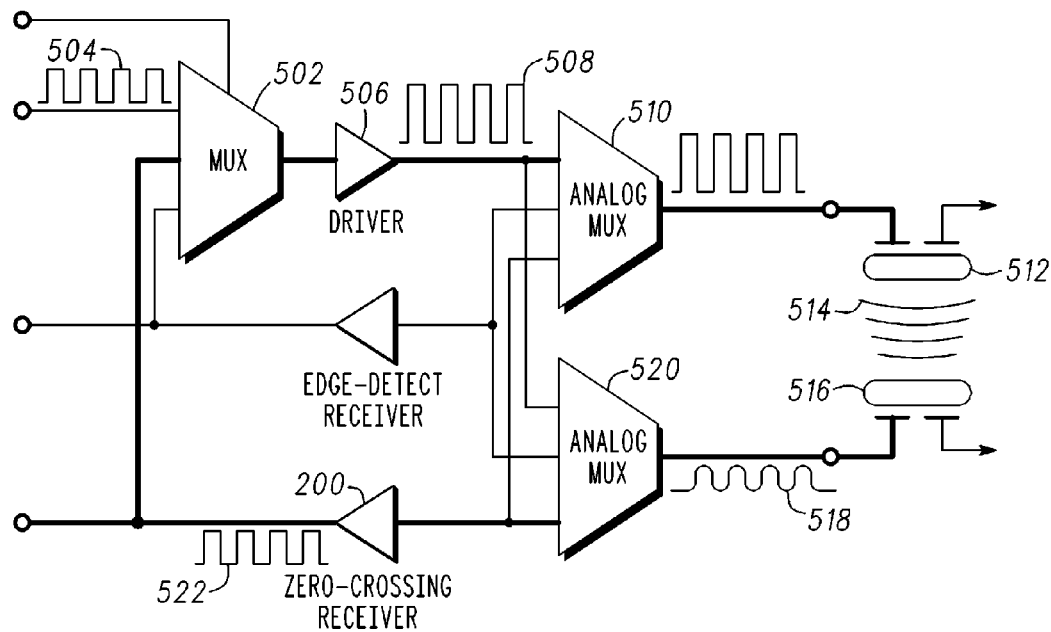
FIG. 5 illustrates a sensor interface incorporating the zero-crossing receiver in a continuous wave multiplexing arrangement for maintaining positive closed-loop feedback in accordance with an example embodiment.

FIG. 5 is a sensor interface diagram incorporating the zero-crossing receiver 200 in a continuous wave multiplexing arrangement for maintaining positive closed-loop feedback in accordance with one embodiment. The positive closed-loop feedback is illustrated by the bold line path. Initially, multiplexer (mux) 502 receives as input a clock signal 504, which is passed to the transducer driver 506 to produce the drive line signal 508. Analog multiplexer (mux) 510 receives drive line signal 508, which is passed to the transmitter transducer 512 to generate energy waves 514. Transducer 512 is located at a first location of an energy propagating medium. The emitted energy waves 514 propagate through the energy propagating medium. Receiver transducer 516 is located at a second location of the energy propagating medium. Receiver transducer 516 captures the energy waves 514, which are fed to analog mux 520 and passed to the zero-crossing receiver 200. The captured energy waves by transducer 516 are indicated by electrical waves 518 provided to mux 520. Zero-crossing receiver 200 outputs a pulse corresponding to each zero crossing detected from captured electrical waves 518. The zero crossings are counted and used to determine changes in the phase and frequency of the energy waves propagating through the energy propagating medium. In a non-limiting example, a parameter such as applied force is measured by relating the measured phase and frequency to a known relationship between the parameter (e.g. force) and the material properties of the energy propagating medium. In general, pulse sequence 522 corresponds to the detected signal frequency. The zero-crossing receiver 200 is in a feedback path of the propagation tuned oscillator. The pulse sequence 522 is coupled through mux 502 in a positive closed-loop feedback path. The pulse sequence 522 disables the clock signal 504 such that the path providing pulse sequence 522 is coupled to driver 506 to continue emission of energy waves into the energy propagating medium and the path of clock signal 504 to driver 506 is disabled.

Figure 6:
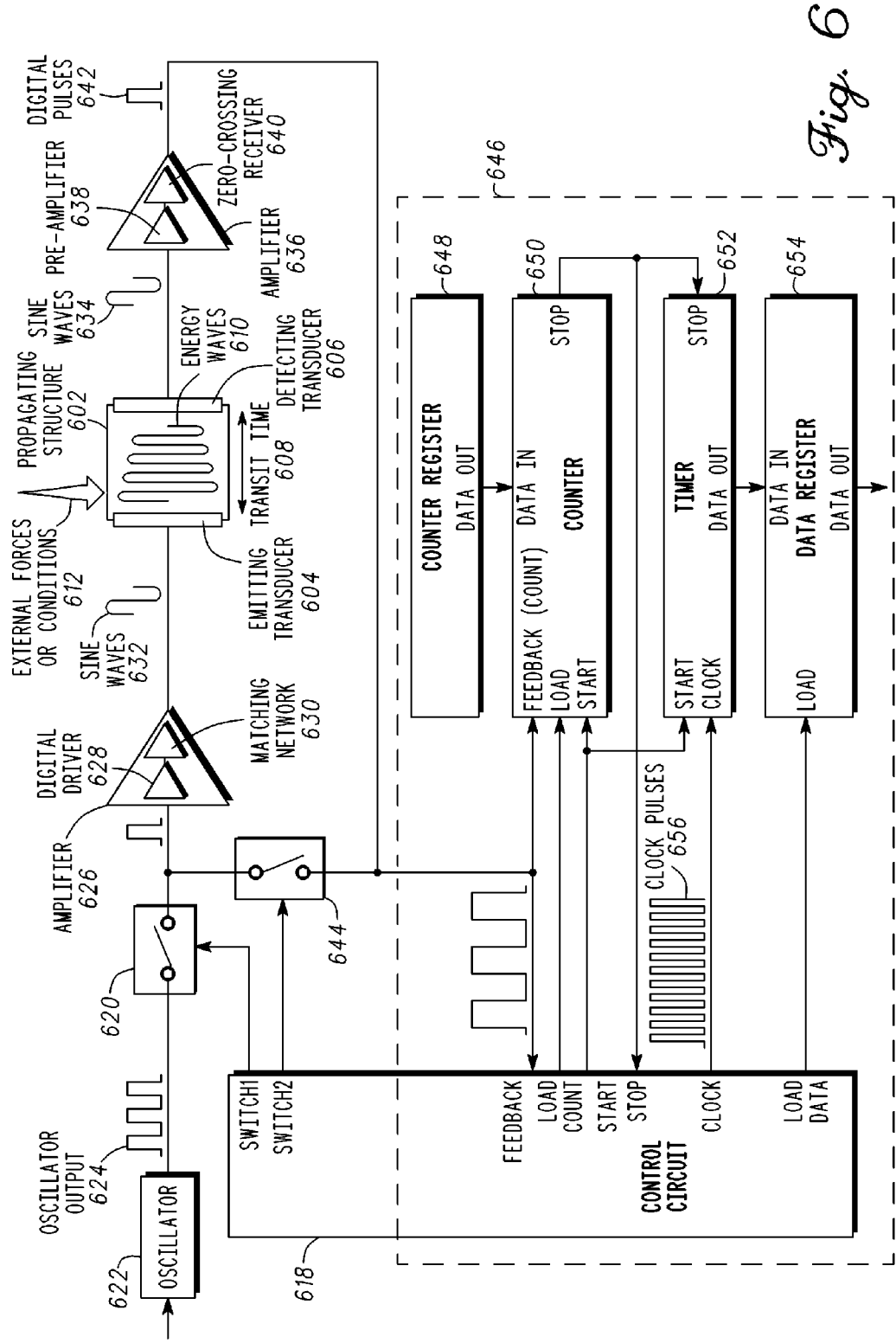
FIG. 6 illustrates a block diagram of a propagation tuned oscillator (PTO) incorporating the integrated zero-crossing receiver for operation in continuous wave mode.

FIG. 6 is an exemplary block diagram of a propagation tuned oscillator (PTO) incorporating the zero-crossing receiver 640 for operation in continuous wave mode. In particular, with respect to FIG. 4, it illustrates closed loop measurement of the transit time 412 of ultrasound waves 414 within the waveguide 408 by the operation of the propagation tuned oscillator 416. This example is for operation in continuous wave mode. The system can also be operated in pulse mode and a pulse-echo mode. Pulse mode and pulsed echo-mode use a pulsed energy wave. Pulse-echo mode uses reflection to direct an energy wave within the energy propagation medium. Briefly, the digital logic circuit 646 digitizes the frequency of operation of the propagation tuned oscillator.

In continuous wave mode of operation a sensor comprising transducer 604, propagating structure 602, and transducer 606 is used to measure the parameter. In general, the parameter to be measured affects the properties of the propagating medium. For example, an external force or condition 612 is applied to propagating structure 602 that changes the length of the waveguide in a path of a propagating energy wave. A change in length corresponds to a change in transit time 608 of the propagating wave. Similarly, the length of propagating structure 602 corresponds to the applied force 612. A length reduction corresponds to a higher force being applied to the propagating structure 602. Conversely, a length increase corresponds to a lowering of the applied force 612 to the propagating structure 602. The length of propagating structure 602 is measured and is converted to force by way of a known length to force relationship.

Transducer 604 is an emitting device in continuous wave mode. The sensor for measuring a parameter comprises transducer 604 coupled to propagating structure 602 at a first location. A transducer 606 is coupled to propagating structure 602 at a second location. Transducer 606 is a receiving transducer for capturing propagating energy waves. In one embodiment, the captured propagated energy waves are electrical sine waves 634 that are output by transducer 606.

A measurement sequence is initiated when control circuitry 618 closes switch 620 coupling oscillator output 624 of oscillator 622 to the input of amplifier 626. One or more pulses provided to amplifier 626 initiates an action to propagate energy waves 610 having simple or complex waveforms through energy propagating structure or medium 602. Amplifier 626 comprises a digital driver 628 and matching network 630. In one embodiment, amplifier 626 transforms the oscillator output of oscillator 622 into sine waves of electrical waves 632 having the same repetition rate as oscillator output 624 and sufficient amplitude to excite transducer 604.

Emitting transducer 604 converts the sine waves 632 into energy waves 610 of the same frequency and emits them at the first location into energy propagating structure or medium 602. The energy waves 610 propagate through energy propagating structure or medium 602. Upon reaching transducer 606 at the second location, energy waves 610 are captured, sensed, or detected. The captured energy waves are converted by transducer 606 into sine waves 634 that are electrical waves having the same frequency.

Amplifier 636 comprises a pre-amplifier 634 and zero-cross receiver 640. Amplifier 636 converts the sine waves 634 into digital pulses 642 of sufficient duration to sustain the behavior of the closed loop circuit. Control circuitry 618 responds to digital pulses 642 from amplifier 636 by opening switch 620 and closing switch 644. Opening switch 620 decouples oscillator output 624 from the input of amplifier 626. Closing switch 644 creates a closed loop circuit coupling the output of amplifier 636 to the input of amplifier 626 and sustaining the emission, propagation, and detection of energy waves through energy propagating structure or medium 602.

An equilibrium state is attained by maintaining unity gain around this closed loop circuit wherein sine waves 632 input into transducer 604 and sine waves 634 output by transducer 606 are in phase with a small but constant offset. Transducer 606 as disclosed above, outputs the sine waves 634 upon detecting energy waves propagating to the second location. In the equilibrium state, an integer number of energy waves 610 propagate through energy propagating structure or medium 602.

Movement or changes in the physical properties of energy propagating structure or medium 602 change a transit time 608 of energy waves 610. The transit time 608 comprises the time for an energy wave to propagate from the first location to the second location of propagating structure 602. Thus, the change in the physical property of propagating structure 602 results in a corresponding time period change of the energy waves 610 within energy propagating structure or medium 602. These changes in the time period of the energy waves 610 alter the equilibrium point of the closed loop circuit and frequency of operation of the closed loop circuit. The closed loop circuit adjusts such that sine waves 632 and 634 correspond to the new equilibrium point. The frequency of energy waves 610 and changes to the frequency correlate to changes in the physical attributes of energy propagating structure or medium 602.

The physical changes may be imposed on energy propagating structure 602 by external forces or conditions 612 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 610 during the operation of the closed loop circuit, and changes in this frequency, may be used to measure movement or changes in physical attributes of energy propagating structure or medium 602.

Prior to measurement of the frequency or operation of the propagation tuned oscillator, control logic 618 loads the loop count into digital counter 650 that is stored in count register 648. The first digital pulses 642 initiates closed loop operation within the propagation tuned oscillator and signals control circuit 618 to start measurement operations. At the start of closed loop operation, control logic 618 enables digital counter 650 and digital timer 652. In one embodiment, digital counter 650 decrements its value on the rising edge of each digital pulse output by zero-crossing receiver 640. Digital timer 652 increments its value on each rising edge of clock pulses 656. When the number of digital pulses 642 has decremented, the value within digital counter 650 to zero a stop signal is output from digital counter 650. The stop signal disables digital timer 652 and triggers control circuit 618 to output a load command to data register 654. Data register 654 loads a binary number from digital timer 652 that is equal to the period of the energy waves or pulses times the value in counter 648 divided by clock period 656. With a constant clock period 656, the value in data register 654 is directly proportional to the aggregate period of the energy waves or pulses accumulated during the measurement operation. Duration of the measurement operation and the resolution of measurements may be adjusted by increasing or decreasing the value preset in the count register 648.

Figure 7:
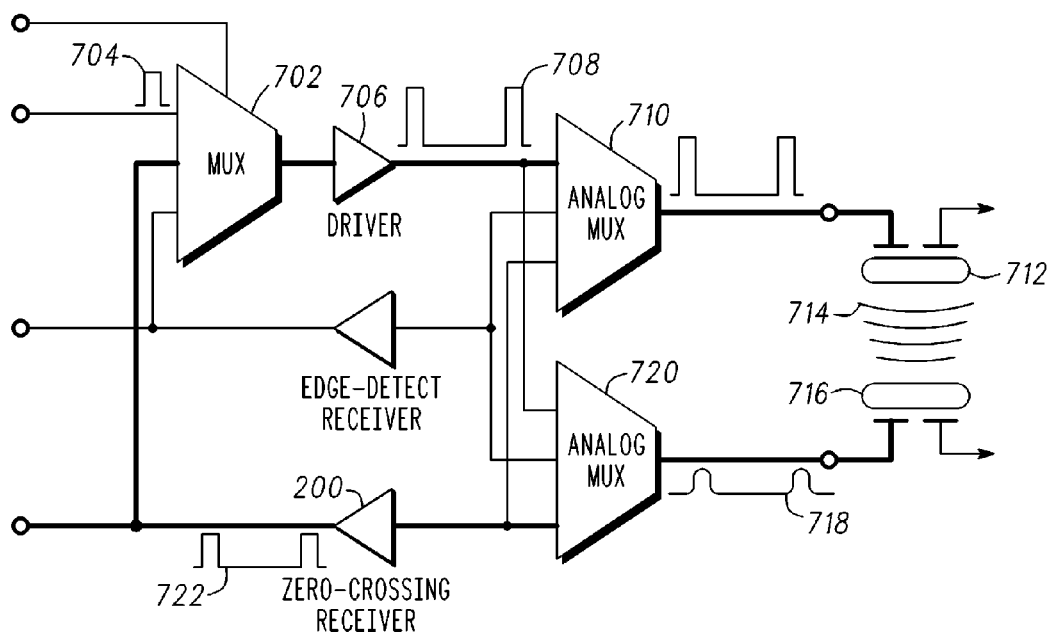
FIG. 7 illustrates a sensor interface diagram incorporating the integrated zero-crossing receiver in a pulse multiplexing arrangement for maintaining positive closed-loop feedback in accordance with an example embodiment.

FIG. 7 is a sensor interface diagram incorporating the integrated zero-crossing receiver 200 in a pulse multiplexing arrangement for maintaining positive closed-loop feedback in accordance with one embodiment. In one embodiment, the circuitry other than the sensor is integrated on an application specific integrated circuit (ASIC). The positive closed-loop feedback is illustrated by the bold line path. Initially, mux 702 is enabled to couple one or more digital pulses 704 to the transducer driver 706. Transducer driver 706 generates a pulse sequence 708 corresponding to digital pulses 704. Analog mux 710 is enabled to couple pulse sequence 708 to the transmitter transducer 712. Transducer 712 is coupled to a medium at a first location. Transducer 712 responds to pulse sequence 708 and generates corresponding energy pulses 714 that are emitted into the medium at the first location. The energy pulses 714 propagate through the medium. A receiver transducer 716 is located at a second location on the medium. Receiver transducer 716 captures the energy pulses 714 and generates a corresponding signal of electrical pulses 718. Transducer 716 is coupled to a mux 720. Mux 720 is enabled to couple to zero-cross receiver 200. Electrical pulses 718 from transducer 716 are coupled to zero-cross receiver 200. Zero-cross receiver 200 counts zero crossings of electrical pulses 718 to determine changes in phase and frequency of the energy pulses responsive to an applied force, as previously explained. Zero-cross receiver 200 outputs a pulse sequence 722 corresponding to the detected signal frequency. Pulse sequence 722 is coupled to mux 702. Mux 702 is decoupled from coupling digital pulses 704 to driver 706 upon detection of pulses 722. Conversely, mux 702 is enabled to couple pulses 722 to driver 706 upon detection of pulses 722 thereby creating a positive closed-loop feedback path. Thus, in pulse mode, zero-cross receiver 200 is part of the closed-loop feedback path that continues emission of energy pulses into the medium at the first location and detection at the second location to measure a transit time and changes in transit time of pulses through the medium.

Figure 8:
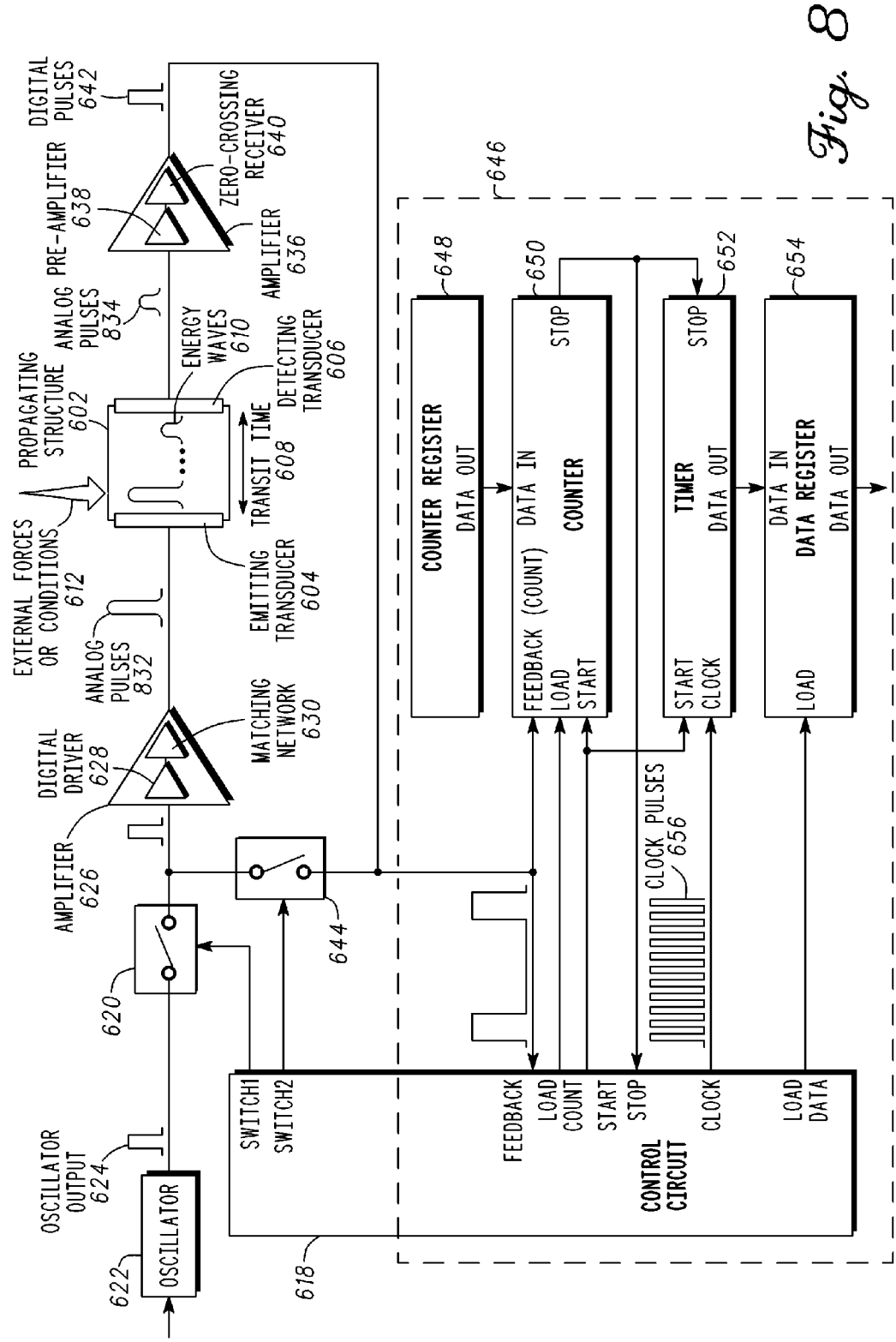
FIG. 8 illustrates a block diagram of a propagation tuned oscillator (PTO) incorporating the integrated zero-crossing receiver for operation in pulse mode in accordance with an example embodiment.

FIG. 8 is an exemplary block diagram of a propagation tuned oscillator (PTO) incorporating the zero-crossing receiver 640 for operation in pulse mode. In particular, with respect to FIG. 4, it illustrates closed loop measurement of the transit time 412 of ultrasound waves 414 within the waveguide 408 by the operation of the propagation tuned oscillator 416. This example is for operation in pulse mode. The system can also be operated in continuous wave mode and a pulse-echo mode. Continuous wave mode uses a continuous wave signal. Pulse-echo mode uses reflection to direct an energy wave within the energy propagation medium. Briefly, the digital logic circuit 646 digitizes the frequency of operation of the propagation tuned oscillator.

In pulse mode of operation, a sensor comprising transducer 604, propagating structure 602, and transducer 606 is used to measure the parameter. In general, the parameter to be measured affects the properties of the propagating medium. For example, an external force or condition 612 is applied to propagating structure 602 that changes the length of the waveguide in a path of a propagating energy wave. A change in length corresponds to a change in transit time 608 of the propagating wave. The length of propagating structure 602 is measured and is converted to force by way of a known length to force relationship. One benefit of pulse mode operation is the use of a high magnitude pulsed energy wave. In one embodiment, the magnitude of the energy wave decays as it propagates through the medium. The use of a high magnitude pulse is a power efficient method to produce a detectable signal if the energy wave has to traverse a substantial distance or is subject to a reduction in magnitude as it propagated due to the medium.

A measurement sequence is initiated when control circuitry 618 closes switch 620 coupling oscillator output 624 of oscillator 622 to the input of amplifier 626. One or more pulses provided to amplifier 626 initiates an action to propagate energy waves 610 having simple or complex waveforms through energy propagating structure or medium 602. Amplifier 626 comprises a digital driver 628 and matching network 630. In one embodiment, amplifier 626 transforms the oscillator output of oscillator 622 into analog pulses of electrical waves 832 having the same repetition rate as oscillator output 624 and sufficient amplitude to excite transducer 604.

Emitting transducer 604 converts the analog pulses 832 into energy waves 610 of the same frequency and emits them at a first location into energy propagating structure or medium 602. The energy waves 610 propagate through energy propagating structure or medium 602. Upon reaching transducer 606 at the second location, energy waves 610 are captured, sensed, or detected. The captured energy waves are converted by transducer 606 into analog pulses 834 that are electrical waves having the same frequency.

Amplifier 636 comprises a pre-amplifier 638 and zero-cross receiver 640. Amplifier 636 converts the analog pulses 834 into digital pulses 642 of sufficient duration to sustain the behavior of the closed loop circuit. Control circuitry 618 responds to digital pulses 642 from amplifier 636 by opening switch 620 and closing switch 644. Opening switch 620 decouples oscillator output 624 from the input of amplifier 626. Closing switch 644 creates a closed loop circuit coupling the output of amplifier 636 to the input of amplifier 626 and sustaining the emission, propagation, and detection of energy waves through energy propagating structure or medium 602.

An equilibrium state is attained by maintaining unity gain around this closed loop circuit wherein pulses 832 input into transducer 604 and pulses 834 output by transducer 606 are in phase with a small but constant offset. Transducer 606 as disclosed above, outputs the pulses 834 upon detecting energy waves propagating to the second location. In the equilibrium state, an integer number of energy waves 610 propagate through energy propagating structure or medium 602.

Movement or changes in the physical properties of energy propagating structure or medium 602 change a transit time 608 of energy waves 610. The transit time 608 comprises the time for an energy wave to propagate from the first location to the second location of propagating structure 602. Thus, the change in the physical property of propagating structure 602 results in a corresponding time period change of the energy waves 610 within energy propagating structure or medium 602. These changes in the time period of the energy waves 610 alter the equilibrium point of the closed loop circuit and frequency of operation of the closed loop circuit. The closed loop circuit adjusts such that pulses 832 and 834 correspond to the new equilibrium point. The frequency of energy waves 610 and changes to the frequency correlate to changes in the physical attributes of energy propagating structure or medium 602.

The physical changes may be imposed on energy propagating structure 602 by external forces or conditions 612 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest as disclosed in more detail hereinabove. Similarly, the frequency of energy waves 610 during the operation of the closed loop circuit, and changes in this frequency, may be used to measure movement or changes in physical attributes of energy propagating structure or medium 602.

Figure 9:
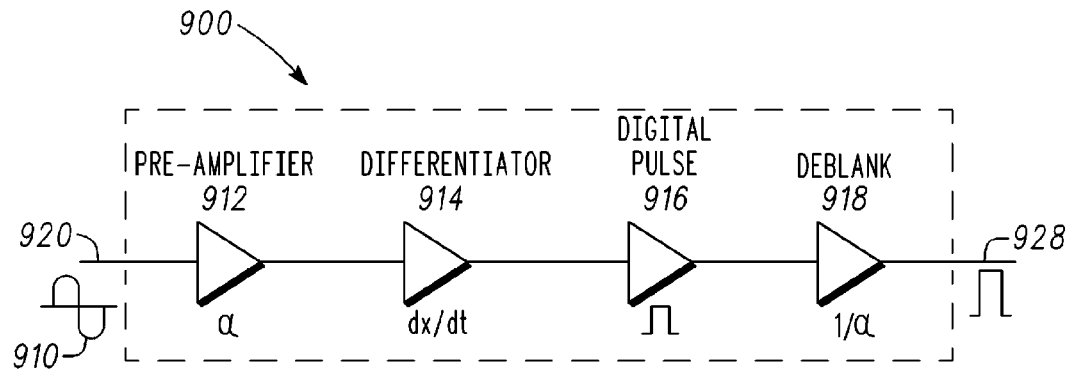
FIG. 9 illustrates a block diagram of an edge-detect receiver circuit in accordance with an example embodiment.

FIG. 9 illustrates a block diagram of an edge-detect receiver circuit 900 in accordance with an exemplary embodiment. In a first embodiment, edge-detect receiver 900 is provided to detect wave fronts of pulses of energy waves. This enables capturing of parameters including, but not limited to, transit time, phase, or frequency of the energy waves. Circuitry of the integrated edge-detect receiver 900 provides rapid on-set detection and quickly responds to the arrival of an energy pulse. It reliably triggers thereafter a digital output pulse at a same point on the initial wave front of each captured energy pulse or pulsed energy wave. The digital pulse can be optimally configured to output with minimal and constant delay. The edge-detect receiver 900 can isolate and precisely detect the specified point on the initial energy wave or the wave front in the presence of interference and distortion signals thereby overcoming problems commonly associated with detecting one of multiple generated complex signals in energy propagating mediums. The edge-detect receiver 900 performs these functions accurately over a wide range of amplitudes including very low-level energy pulses.

In a second embodiment, the edge-detect receiver 900 is incorporated within a propagation tuned oscillator (PTO) to maintain positive closed-loop feedback when operating in a pulse or pulse-echo mode. The edge-detect receiver 900 can be integrated with other circuitry of the PTO by multiplexing input and output circuitry to achieve ultra low-power and small compact size. Integration of the circuitry of the PTO with the edge-detect receiver provides the benefit of increasing sensitivity to low-level signals.

The block diagram illustrates one embodiment of a low power edge-detect receiver circuit 900 with superior performance at low signal levels. The edge-detect receiver 900 comprises a preamplifier 912, a differentiator 914, a digital pulse circuit 916 and a deblank circuit 918. The edge-detect receiver circuit 900 can be implemented in discrete analog components, digital components or combination thereof. In one embodiment, edge-detect receiver 900 is integrated into an ASIC as part of a sensor system described hereinbelow. The edge-detect receiver circuit 900 practices measurement methods that detect energy pulses or pulsed energy waves at specified locations and under specified conditions to enable capturing parameters including, but not limited to, transit time, phase, frequency, or amplitude of energy pulses. A brief description of the method of operation is as follows. In a non-limiting example, a pre-amplifier triggers a comparator circuit responsive to small changes in the slope of an input signal. The comparator and other edge-detect circuitry responds rapidly with minimum delay. Detection of small changes in the input signal assures rapid detection of the arrival of a pulse of energy waves. The minimum phase design reduces extraneous delay thereby introducing less variation into the measurement of the transit time, phase, frequency, or amplitude of the incoming energy pulses.

An input 920 of edge-detect receiver 900 is coupled to pre-amplifier 912. As an example, the incoming wave 910 to the edge-detect receiver circuit 900 can be received from an electrical connection, antenna, or transducer. The incoming wave 910 is amplified by pre-amplifier 912, which assures adequate sensitivity to small signals. Differentiator circuitry 914 monitors the output of pre-amplifier 912 and triggers digital pulse circuitry 916 whenever a signal change corresponding to a pulsed energy wave is detected. For example, a signal change that identifies the pulsed energy wave is the initial wave front or the leading edge of the pulsed energy wave. In one arrangement, differentiator 914 detects current flow, and more specifically changes in the slope of the energy wave 910 by detecting small changes in current flow instead of measuring changes in voltage level to achieve rapid detection of slope. Alternatively, differentiator 914 can be implemented to trigger on changes in voltage. Together, preamplifier 912 and differentiator 916 monitor the quiescent input currents for the arrival of wave front of energy wave(s) 910. Preamplifier 912 and differentiator 916 detect the arrival of low level pulses of energy waves as well as larger pulses of energy waves. This detection methodology achieves superior performance for very low level signals. Differentiator circuitry 912 triggers digital pulse circuitry 916 whenever current flow driven by the initial signal ramp of the incoming wave 910 is detected. The digital pulse is coupled to deblank circuit 918 that desensitizes pre-amplifier 912. For example, the desensitization of pre-amplifier 912 can comprise a reduction in gain, decoupling of input 920 from energy wave 910, or changing the frequency response. The deblank circuit 918 also disregards voltage or current levels for a specified or predetermined duration of time to effectively skip over the interference sections or distorted portions of the energy wave 910. In general, energy wave 910 can comprise more than one change in slope and is typically a damped wave form. Additional signals or waves of the pulsed energy wave on the input 920 of pre-amplifier 912 are not processed during the preset blanking period. In this example, the digital output pulse 928 can then be coupled to signal processing circuitry as explained hereinbelow. In one embodiment, the electronic components are operatively coupled as blocks within an integrated circuit. As will be shown ahead, this integration arrangement performs its specific functions efficiently with a minimum number of components. This is because the circuit components are partitioned between structures within an integrated circuit and discrete components, as well as innovative partitioning of analog and digital functions, to achieve the required performance with a minimum number of components and minimum power consumption.

Figure 10:
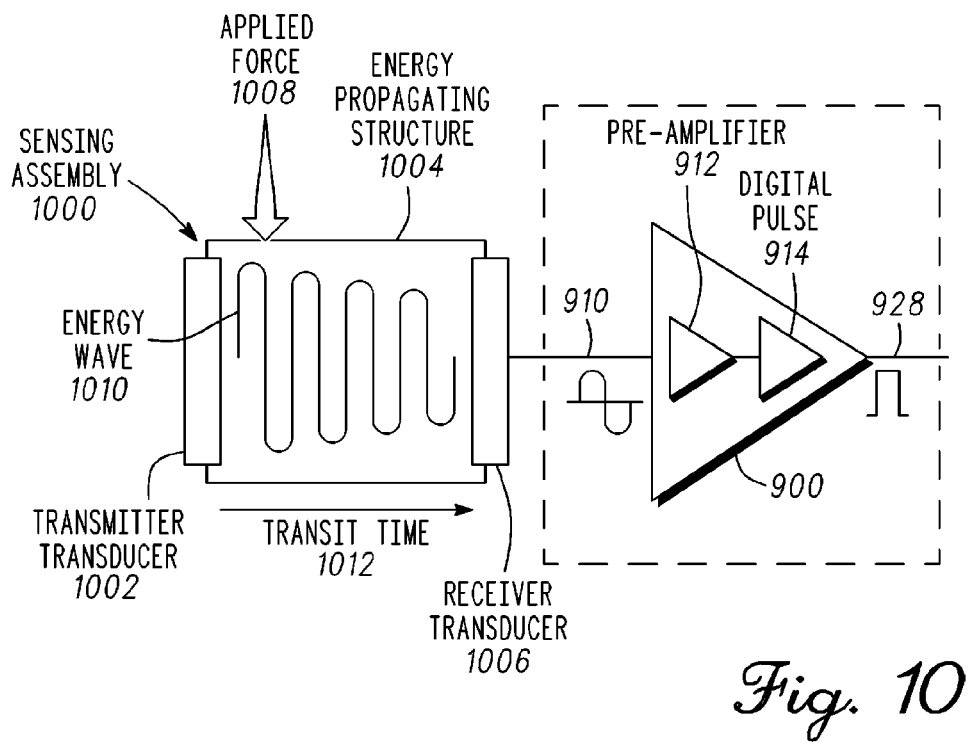
FIG. 10 illustrates a block diagram of the edge-detect receiver circuit coupled to a sensing assembly.

FIG. 10 illustrates a block diagram of the edge-detect receiver circuit 900 coupled to a sensing assembly 1000. The pre-amplifier 912 and the digital pulse circuit 916 are shown for reference and discussion. The sensing assembly 1000 comprises a transmitter transducer 1002, an energy propagating medium 1004, and a receiver transducer 1006. The transmitter transducer 1002 is coupled to propagating medium 1004 at a first location. The receiver transducer 1006 is coupled to energy propagating medium 1004 at a second location. Alternatively, a reflecting surface can replace receiver transducer 1006. The reflecting surface reflects an energy wave back towards the first location. Transducer 1006 can be enabled to be a transmitting transducer and a receiving transducer thereby saving the cost of a transducer. As will be explained ahead in further detail, the sensing assembly 1000 in one embodiment is part of a sensory device that assess loading, in particular, the externally applied forces 1008 on the sensing assembly 1000. A transducer driver circuit (not shown) drives the transmitter transducer 1002 of the sensing assembly 1000 to produce energy waves 1010 that are directed into the energy propagating medium 1004. In the non-limiting example, changes in the energy propagating medium 1004 due to the externally applied forces 1008 change the frequency, phase, and transit time 1012 of energy waves 1010 propagating from the first location to the second location of energy propagating medium 1004. The integrated edge-detect receiver circuit 900 is coupled to the receiver transducer 1006 to detect edges of the reproduced energy wave 910 and trigger the digital pulse 928. In general, the timing of the digital pulse 928 conveys the parameters of interest (e.g., distance, force weight, strain, pressure, wear, vibration, viscosity, density, direction, displacement, etc.) related to the change in energy propagating structure 1004 due to an external parameter. For example, sensing assembly 1000 placed in a knee joint as described hereinabove.

Measurement methods that rely on the propagation of energy pulses require the detection of energy pulses at specified locations or under specified conditions to enable capturing parameters including, but not limited to, transit time, phase, frequency, or amplitude of the energy pulses. Measurement methods that rely on such propagation of energy waves 1010 or pulses of energy waves are required to achieve highly accurate and controlled detection of energy waves or pulses. Moreover, pulses of energy waves may contain multiple energy waves with complex waveforms therein leading to potential ambiguity of detection. In particular, directing energy waves 1010 into the energy propagating structure 1004 can generate interference patterns caused by nulls and resonances of the waveguide, as well as characteristics of the generated energy wave 1010. These interference patterns can generate multiply excited waveforms that result in distortion of the edges of the original energy wave. To reliably detect the arrival of a pulse of energy waves, the edge-detect receiver 900 only responds to the leading edge of the first energy wave within each pulse. This is achieved in part by blanking the edge-detect circuitry 900 for the duration of each energy pulse. As an example, the deblank circuit 918 disregards voltage or current levels for a specified duration of time to effectively skip over the interference sections or distorted portions of the waveform.

Figure 11:
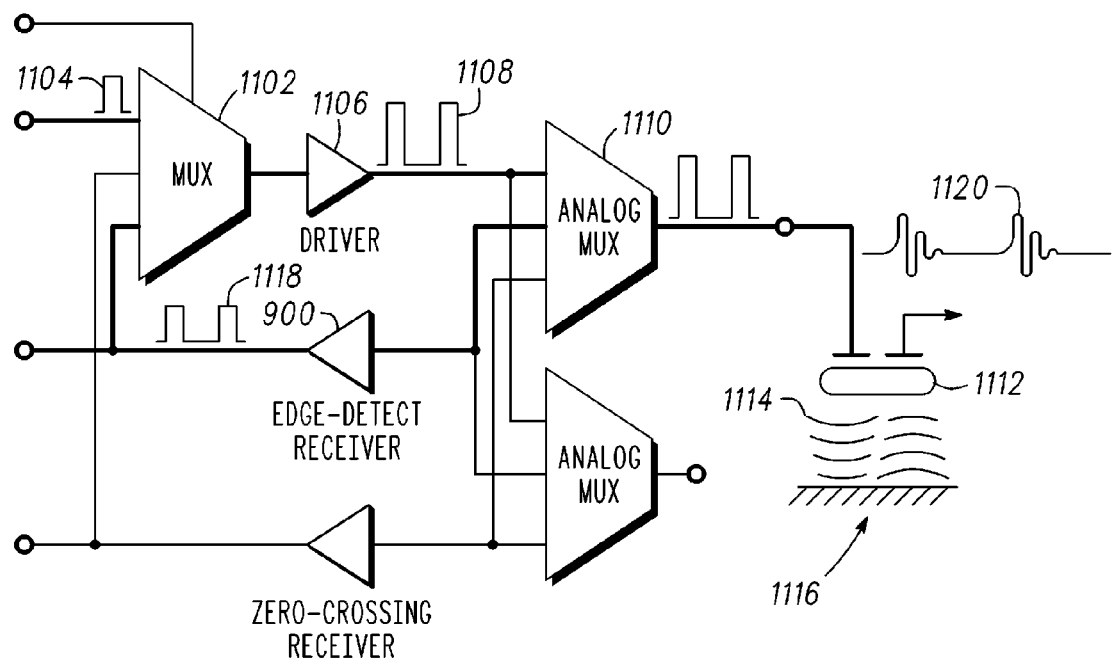
FIG. 11 illustrates a sensor interface diagram incorporating the edge-detect receiver circuit in a pulse-echo multiplexing arrangement for maintaining positive closed-loop feedback in accordance with an example embodiment.

FIG. 11 is a sensor interface diagram incorporating the edge-detect receiver circuit 900 in a pulse-echo multiplexing arrangement for maintaining positive closed-loop feedback in accordance with one embodiment. The positive closed-loop feedback is illustrated by the bold line path. Initially, multiplexer (mux) 1102 receives as input a digital pulse 1104, which is passed to the transducer driver 1106 to produce the pulse sequence 1108. Analog multiplexer (mux) 1110 receives pulse sequence 1108, which is passed to the transducer 1112 to generate energy pulses 1114. Energy pulses 1114 are emitted into a first location of a medium and propagate through the medium. In the pulse-echo example, energy pulses 1114 are reflected off a surface 1116 at a second location of the medium, for example, the end of a waveguide or reflector, and echoed back to the transducer 1112. The transducer 1112 proceeds to then capture the reflected pulse echo. In pulsed echo mode, the transducer 1112 performs as both a transmitter and a receiver. As disclosed above, transducer 1112 toggles back and forth between emitting and receiving energy waves. Transducer 1112 captures the reflected echo pulses, which are coupled to analog mux 1110 and directed to the edge-detect receiver 900. The captured reflected echo pulses is indicated by electrical waves 1120. Edge-detect receiver 900 locks on pulse edges corresponding to the wave front of a propagated energy wave to determine changes in phase and frequency of the energy pulses 1114 responsive to an applied force, as previously explained. Among other parameters, it generates a pulse sequence 1118 corresponding to the detected signal frequency. The pulse sequence 1118 is coupled to mux 1102 and directed to driver 1106 to initiate one or more energy waves being emitted into the medium by transducer 1112. Pulse 1104 is decoupled from being provided to driver 1106. Thus, a positive closed loop feedback is formed that repeatably emits energy waves into the medium until mux 1102 prevents a signal from being provided to driver 1106. The edge-detect receiver 900 is coupled to a second location of the medium and is in the feedback path. The edge-detect receiver 900 initiates a pulsed energy wave being provided at the first location of the medium upon detecting a wave front at the second location when the feedback path is closed.

Figure 12:
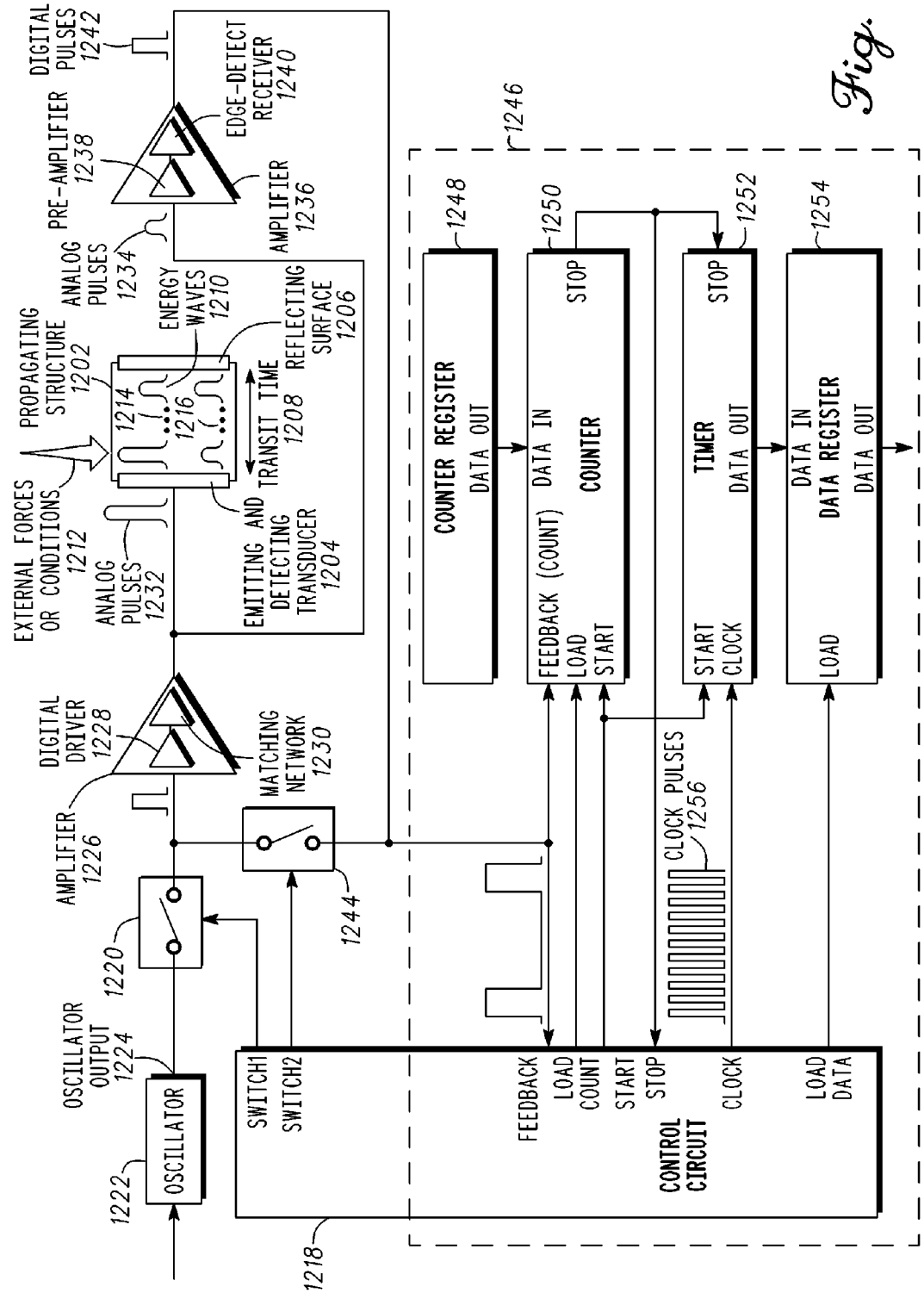
FIG. 12 illustrates a block diagram of a propagation tuned oscillator (PTO) incorporating the edge-detect receiver circuit for operation in pulse echo mode.

FIG. 12 is an exemplary block diagram of a propagation tuned oscillator (PTO) incorporating the edge-detect receiver circuit 900 for operation in pulse echo mode. In particular, with respect to FIG. 4, it illustrates closed loop measurement of the transit time 412 of ultrasound waves 414 within the waveguide 408 by the operation of the propagation tuned oscillator 416. This example is for operation in a pulse echo mode. The system can also be operated in pulse mode and a continuous wave mode. Pulse mode does not use a reflected signal. Continuous wave mode uses a continuous signal. Briefly, the digital logic circuit 1246 digitizes the frequency of operation of the propagation tuned oscillator.

In pulse-echo mode of operation a sensor comprising transducer 1204, propagating structure 1202, and reflecting surface 1206 is used to measure the parameter. In general, the parameter to be measured affects the properties of the propagating medium. For example, an external force or condition 1212 is applied to propagating structure 1202 that changes the length of the waveguide in a path of a propagating energy wave. A change in length corresponds to a change in transit time of the propagating wave. Similarly, the length of propagating structure 1202 corresponds to the applied force 1212. A length reduction corresponds to a higher force being applied to the propagating structure 1202. Conversely, a length increase corresponds to a lowering of the applied force 1212 to the propagating structure 1202. The length of propagating structure 1202 is measured and is converted to force by way of a known length to force relationship.

Transducer 1204 is both an emitting device and a receiving device in pulse-echo mode. The sensor for measuring a parameter comprises transducer 1204 coupled to propagating structure 1202 at a first location. A reflecting surface is coupled to propagating structure 1202 at a second location. Transducer 1204 has two modes of operation comprising an emitting mode and receiving mode. Transducer 1204 emits an energy wave into the propagating structure 1202 at the first location in the emitting mode. The energy wave propagates to a second location and is reflected by reflecting surface 1206. The reflected energy wave is reflected towards the first location and transducer 1204 subsequently generates a signal in the receiving mode corresponding to the reflected energy wave.

A measurement sequence in pulse echo mode is initiated when control circuitry 1218 closes switch 1220 coupling digital output 1224 of oscillator 1222 to the input of amplifier 1226. One or more pulses provided to amplifier 1226 starts a process to emit one or more energy waves 1210 having simple or complex waveforms into energy propagating structure or medium 1202. Amplifier 1226 comprises a digital driver 1228 and matching network 1230. In one embodiment, amplifier 1226 transforms the digital output of oscillator 1222 into pulses of electrical waves 1232 having the same repetition rate as digital output 1224 and sufficient amplitude to excite transducer 1204.

Transducer 1204 converts the pulses of electrical waves 1232 into pulses of energy waves 1210 of the same repetition rate and emits them into energy propagating structure or medium 1202. The pulses of energy waves 1210 propagate through energy propagating structure or medium 1202 as shown by arrow 1214 towards reflecting surface 1206. Upon reaching reflecting surface 1206, energy waves 1210 are reflected by reflecting surface 1206. Reflected energy waves propagate towards transducer 1204 as shown by arrow 1216. The reflected energy waves are detected by transducer 1204 and converted into pulses of electrical waves 1234 having the same repetition rate.

Amplifier 1236 comprises a pre-amplifier 1234 and edge-detect receiver 1240. Amplifier 1236 converts the pulses of electrical waves 1234 into digital pulses 1242 of sufficient duration to sustain the pulse behavior of the closed loop circuit. Control circuitry 1218 responds to digital output pulses 1242 from amplifier 1236 by opening switch 1220 and closing switch 1244. Opening switch 1220 decouples oscillator output 1224 from the input of amplifier 1226. Closing switch 1244 creates a closed loop circuit coupling the output of amplifier 1236 to the input of amplifier 1226 and sustaining the emission, propagation, and detection of energy pulses through energy propagating structure or medium 1202.

An equilibrium state is attained by maintaining unity gain around this closed loop circuit wherein electrical waves 1232 input into transducer 1204 and electrical waves 1234 output by transducer 1204 are in phase with a small but constant offset. Transducer 1204 as disclosed above, outputs the electrical waves 1234 upon detecting reflected energy waves reflected from reflecting surface 1206. In the equilibrium state, an integer number of pulses of energy waves 1210 propagate through energy propagating structure or medium 1202.

Movement or changes in the physical properties of energy propagating structure or medium 1202 change a transit time 1208 of energy waves 1210. The transit time 1208 comprises the time for an energy wave to propagate from the first location to the second location of propagating structure 1202 and the time for the reflected energy wave to propagate from the second location to the first location of propagating structure 1202. Thus, the change in the physical property of propagating structure 1202 results in a corresponding time period change of the energy waves 1210 within energy propagating structure or medium 1202. These changes in the time period of the repetition rate of the energy pulses 1210 alter the equilibrium point of the closed loop circuit and repetition rate of operation of the closed loop circuit. The closed loop circuit adjusts such that electrical waves 1232 and 1234 correspond to the new equilibrium point. The repetition rate of energy waves 1210 and changes to the repetition rate correlate to changes in the physical attributes of energy propagating structure or medium 1202.

The physical changes may be imposed on energy propagating structure 1202 by external forces or conditions 1212 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 1210 during the operation of the closed loop circuit, and changes in this frequency, may be used to measure movement or changes in physical attributes of energy propagating structure or medium 1202.

Prior to measurement of the frequency or operation of the propagation tuned oscillator, control logic 1218 loads the loop count into digital counter 1250 that is stored in count register 1248. The first digital pulses 1242 initiates closed loop operation within the propagation tuned oscillator and signals control circuit 1218 to start measurement operations. At the start of closed loop operation, control logic 1218 enables digital counter 1250 and digital timer 1252. In one embodiment, digital counter 1250 decrements its value on the rising edge of each digital pulse output by edge-detect receiver 1240. Digital timer 1252 increments its value on each rising edge of clock pulses 1256. When the number of digital pulses 1242 has decremented, the value within digital counter 1250 to zero a stop signal is output from digital counter 1250. The stop signal disables digital timer 1252 and triggers control circuit 1218 to output a load command to data register 1254. Data register 1254 loads a binary number from digital timer 1252 that is equal to the period of the energy waves or pulses times the value in counter 1248 divided by clock period 1256. With a constant clock period 1256, the value in data register 1254 is directly proportional to the aggregate period of the energy waves or pulses accumulated during the measurement operation. Duration of the measurement operation and the resolution of measurements may be adjusted by increasing or decreasing the value preset in the count register 1248.

Figure 13:
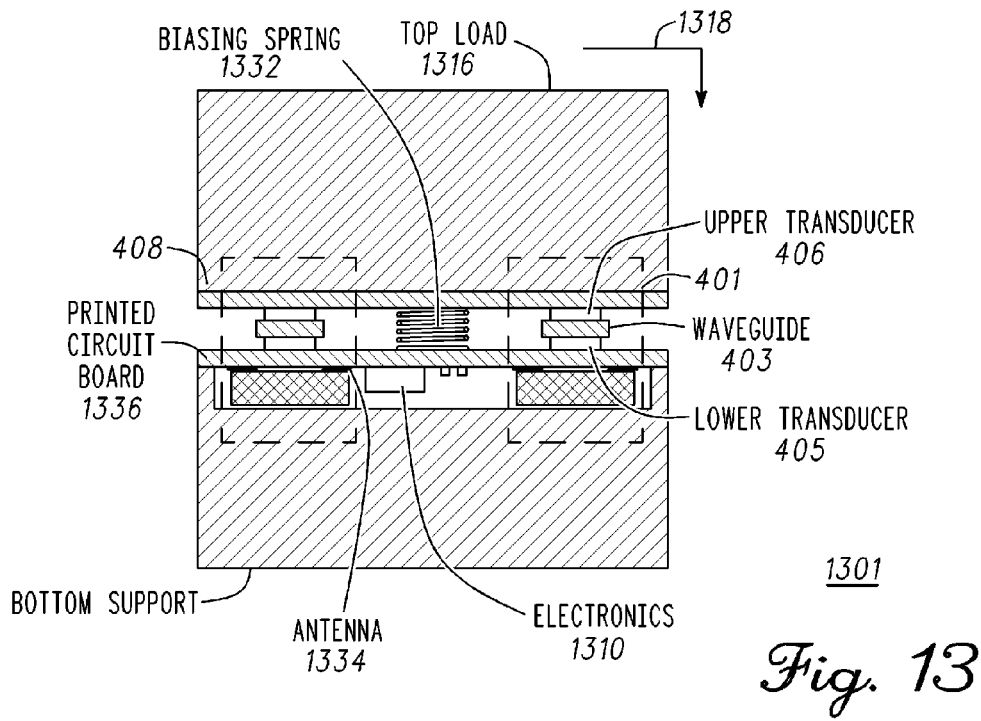
FIG. 13 illustrates a simplified cross-sectional view of a sensing module in accordance with an example embodiment.

FIG. 13 is a simplified cross-sectional view of a sensing module 1301 in accordance with an exemplary embodiment. The sensing module (or assemblage) is an electro-mechanical assembly comprising electrical components and mechanical components that when configured and operated in accordance with a sensing mode performs as a positive feedback closed-loop measurement system. The measurement system can precisely measure applied forces, such as loading, on the electro-mechanical assembly. The sensing mode can be a continuous mode, a pulse mode, or a pulse echo-mode.

In one embodiment, the electrical components can include ultrasound resonators or transducers 405 and 406, ultrasound waveguides 403, and signal processing electronics 1310, but are not limited to these. The mechanical components can include biasing springs 1332, spring retainers and posts, and load platforms 1306, but are not limited to these. The electrical components and mechanical components can be inter-assembled (or integrated) onto a printed circuit board 1336 to operate as a coherent ultrasonic measurement system within sensing module 1301 and according to the sensing mode. As will be explained ahead in more detail, the signal processing electronics incorporate a propagation tuned oscillator (PTO) or a phase locked loop (PLL) to control the operating frequency of the ultrasound resonators or transducers for providing high precision sensing. Furthermore, the signal processing electronics incorporate detect circuitry that consistently detects an energy wave after it has propagated through a medium. The detection initiates the generation of a new energy wave by an ultrasound resonator or transducer that is coupled to the medium for propagation therethrough. A change in transit time of an energy wave through the medium is measured and correlates to a change in material property of the medium due to one or more parameters applied thereto.

Sensing module 1301 comprises one or more assemblages 401 each comprised one or more ultrasound resonators 405 and 406. As illustrated, waveguide 403 is coupled between transducers (405, 406) and affixed to load bearing or contacting surfaces 408. In one exemplary embodiment, an ultrasound signal is coupled for propagation through waveguide 403. The sensing module 1301 is placed, attached to, or affixed to, or within a body, instrument, or other physical system 1318 having a member or members 1316 in contact with the load bearing or contacting surfaces 408 of the sensing module 401. This arrangement facilitates translating the parameters of interest into changes in the length or compression or extension of the waveguide or waveguides 403 within the sensing module 1301 and converting these changes in length into electrical signals. This facilitates capturing data, measuring parameters of interest and digitizing that data, and then subsequently communicating that data through antenna 1334 to external equipment with minimal disturbance to the operation of the body, instrument, appliance, vehicle, equipment, or physical system 1318 for a wide range of applications.

The sensing module 401 supports three modes of operation of energy wave propagation and measurement: reflectance, unidirectional, and bi-directional. These modes can be used as appropriate for each individual application. In unidirectional and bi-directional modes, a chosen ultrasound resonator or transducer is controlled to emit pulses of ultrasound waves into the ultrasound waveguide and one or more other ultrasound resonators or transducers are controlled to detect the propagation of the pulses of ultrasound waves at a specified location or locations within the ultrasound waveguide. In reflectance or pulse-echo mode, a single ultrasound or transducer emits pulses of ultrasound waves into waveguide 403 and subsequently detects pulses of echo waves after reflection from a selected feature or termination of the waveguide. In pulse-echo mode, echoes of the pulses can be detected by controlling the actions of the emitting ultrasound resonator or transducer to alternate between emitting and detecting modes of operation. Pulse and pulse-echo modes of operation may require operation with more than one pulsed energy wave propagating within the waveguide at equilibrium.

Many parameters of interest within physical systems or bodies can be measured by evaluating changes in the transit time of energy pulses. The frequency, as defined by the reciprocal of the average period of a continuous or discontinuous signal, and type of the energy pulse is determined by factors such as distance of measurement, medium in which the signal travels, accuracy required by the measurement, precision required by the measurement, form factor of that will function with the system, power constraints, and cost. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

In the non-limiting example, pulses of ultrasound energy provide accurate markers for measuring transit time of the pulses within waveguide 403. In general, an ultrasonic signal is an acoustic signal having a frequency above the human hearing range (e.g. >20 KHz) including frequencies well into the megahertz range. In one embodiment, a change in transit time of an ultrasonic energy pulse corresponds to a difference in the physical dimension of the waveguide from a previous state. For example, a force or pressure applied across the knee joint compresses waveguide 403 to a new length and changes the transit time of the energy pulse When integrated as a sensing module and inserted or coupled to a physical system or body, these changes are directly correlated to the physical changes on the system or body and can be readily measured as a pressure or a force.

Figure 14:
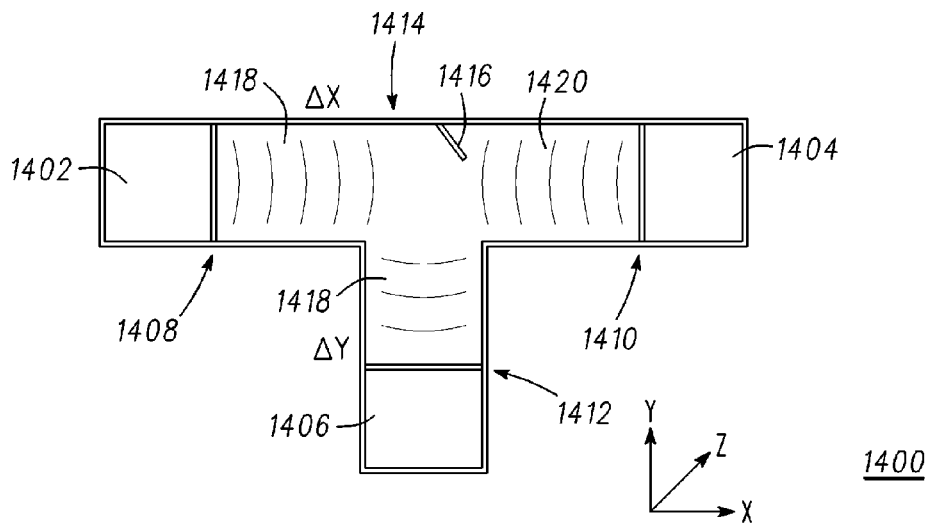
FIG. 14 illustrates an assemblage for illustrating reflectance and unidirectional modes of operation in accordance with an example embodiment.

FIG. 14 is an exemplary assemblage 1400 for illustrating reflectance and unidirectional modes of operation in accordance with an exemplary embodiment. It comprises one or more transducers 1402, 1404, and 1406, one or more waveguides 1414, and one or more optional reflecting surfaces 1416. The assemblage 1400 illustrates propagation of ultrasound waves 1418 within the waveguide 1414 in the reflectance and unidirectional modes of operation. Either ultrasound resonator or transducer 1402 and 1404 in combination with interfacing material or materials 1408 and 1410, if required, can be selected to emit ultrasound waves 1418 into the waveguide 1414.

In unidirectional mode, either of the ultrasound resonators or transducers for example 1402 can be enabled to emit ultrasound waves 1418 into the waveguide 1414. The non-emitting ultrasound resonator or transducer 1404 is enabled to detect the ultrasound waves 1418 emitted by the ultrasound resonator or transducer 1402.

In reflectance mode, the ultrasound waves 1418 are detected by the emitting ultrasound resonator or transducer 1402 after reflecting from a surface, interface, or body at the opposite end of the waveguide 1414. In this mode, either of the ultrasound resonators or transducers 1402 or 1404 can be selected to emit and detect ultrasound waves. Additional reflection features 1416 can be added within the waveguide structure to reflect ultrasound waves. This can support operation in a combination of unidirectional and reflectance modes. In this mode of operation, one of the ultrasound resonators, for example resonator 1402 is controlled to emit ultrasound waves 1418 into the waveguide 1414. Another ultrasound resonator or transducer 1406 is controlled to detect the ultrasound waves 1418 emitted by the emitting ultrasound resonator 1402 (or transducer) subsequent to their reflection by reflecting feature 1416.

Figure 15:
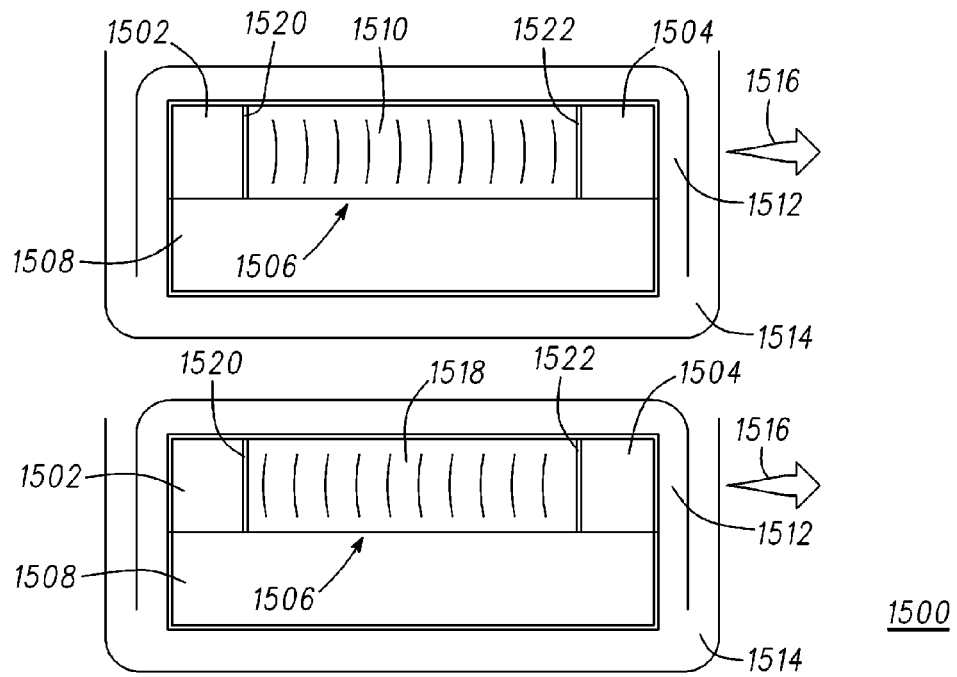
FIG. 15 illustrates an assemblage that illustrates propagation of ultrasound waves within a waveguide in the bi-directional mode of operation of this assemblage.

FIG. 15 is an exemplary assemblage 1500 that illustrates propagation of ultrasound waves 1510 within the waveguide 1506 in the bi-directional mode of operation of this assemblage. In this mode, the selection of the roles of the two individual ultrasound resonators (1502, 1504) or transducers affixed to interfacing material 1520 and 1522, if required, are periodically reversed. In the bi-directional mode the transit time of ultrasound waves propagating in either direction within the waveguide 1506 can be measured. This can enable adjustment for Doppler effects in applications where the sensing module 1508 is operating while in motion 1516. Furthermore, this mode of operation helps assure accurate measurement of the applied load, force, pressure, or displacement by capturing data for computing adjustments to offset this external motion 1516. An advantage is provided in situations wherein the body, instrument, appliance, vehicle, equipment, or other physical system 1514, is itself operating or moving during sensing of load, pressure, or displacement. Similarly, the capability can also correct in situation where the body, instrument, appliance, vehicle, equipment, or other physical system, is causing the portion 1512 of the body, instrument, appliance, vehicle, equipment, or other physical system being measured to be in motion 1516 during sensing of load, force, pressure, or displacement. Other adjustments to the measurement for physical changes to system 1514 are contemplated and can be compensated for in a similar fashion. For example, temperature of system 1514 can be measured and a lookup table or equation having a relationship of temperature versus transit time can be used to normalize measurements. Differential measurement techniques can also be used to cancel many types of common factors as is known in the art.

The use of waveguide 1506 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 16:
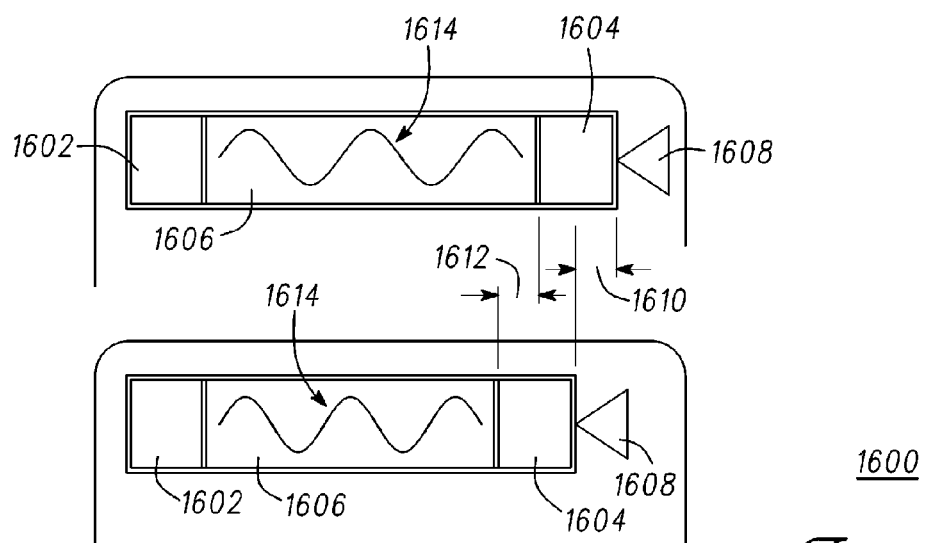
FIG. 16 illustrates a cross-sectional view of a sensor element to illustrate changes in the propagation of ultrasound waves with changes in the length of a waveguide.

FIG. 16 is an exemplary cross-sectional view of a sensor element 1600 to illustrate changes in the propagation of ultrasound waves 1614 with changes in the length of a waveguide 1606. In general, the measurement of a parameter is achieved by relating displacement to the parameter. In one embodiment, the displacement required over the entire measurement range is measured in microns. For example, an external force 1608 compresses waveguide 1606 thereby changing the length of waveguide 1606. Sensing circuitry (not shown) measures propagation characteristics of ultrasonic signals in the waveguide 1606 to determine the change in the length of the waveguide 1606. These changes in length change in direct proportion to the parameters of interest thus enabling the conversion of changes in the parameter or parameters of interest into electrical signals.

As illustrated, external force 1608 compresses waveguide 1606 and moves the transducers 1602 and 1604 closer to one another by a distance 1610. This changes the length of waveguide 1606 by distance 1612 of the waveguide propagation path between transducers 1602 and 1604. Depending on the operating mode, the sensing circuitry measures the change in length of the waveguide 1606 by analyzing characteristics of the propagation of ultrasound waves within the waveguide.

One interpretation of FIG. 16 illustrates waves emitting from transducer 1602 at one end of waveguide 1606 and propagating to transducer 1604 at the other end of the waveguide 1606. The interpretation includes the effect of movement of waveguide 1606 and thus the velocity of waves propagating within waveguide 1606 (without changing shape or width of individual waves) and therefore the transit time between transducers 1602 and 1604 at each end of the waveguide. The interpretation further includes the opposite effect on waves propagating in the opposite direction and is evaluated to estimate the velocity of the waveguide and remove it by averaging the transit time of waves propagating in both directions.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

In a continuous wave mode of operation, a phase detector (not shown) evaluates the frequency and changes in the frequency of resonant ultrasonic waves in the waveguide 1606. As will be described below, positive feedback closed-loop circuit operation in continuous wave (CW) mode adjusts the frequency of ultrasonic waves 1614 in the waveguide 1606 to maintain a same number or integer number of periods of ultrasonic waves in the waveguide 1606. The CW operation persists as long as the rate of change of the length of the waveguide is not so rapid that changes of more than a quarter wavelength occur before the frequency of the Propagation Tuned Oscillator (PTO) can respond. This restriction exemplifies one advantageous difference between the performance of a PTO and a Phase Locked Loop (PLL). Assuming the transducers are producing ultrasonic waves, for example, at 2.4 MHz, the wavelength in air, assuming a velocity of 343 microns per microsecond, is about 143µ, although the wavelength within a waveguide may be longer than in unrestricted air.

In a pulse mode of operation, the phase detector measures a time of flight (TOF) between when an ultrasonic pulse is transmitted by transducer 1602 and received at transducer 1604. The time of flight determines the length of the waveguide propagating path, and accordingly reveals the change in length of the waveguide 1606. In another arrangement, differential time of flight measurements (or phase differences) can be used to determine the change in length of the waveguide 1606. A pulse consists of a pulse of one or more waves. The waves may have equal amplitude and frequency (square wave pulse) or they may have different amplitudes, for example, decaying amplitude (trapezoidal pulse) or some other complex waveform. The PTO is holding the phase of the leading edge of the pulses propagating through the waveguide constant. In pulse mode operation the PTO detects the leading edge of the first wave of each pulse with an edge-detect receiver rather than a zero-crossing receiver circuitry as used in CW mode.

Figure 18:
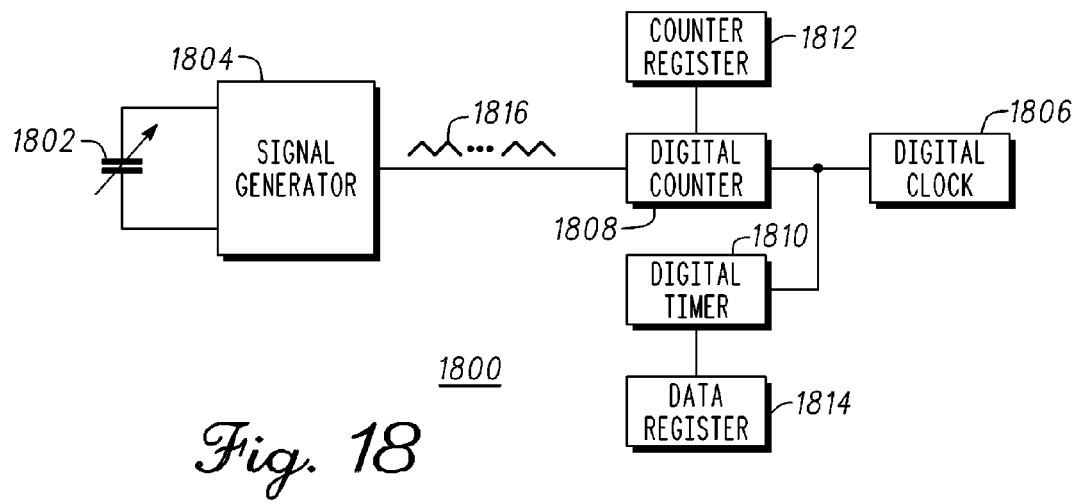
FIG. 18 illustrates a block diagram of a medical sensing system in accordance with an example embodiment.

FIG. 18 illustrates a block diagram of a medical sensing system 1800 in accordance with an example embodiment. The medical sensing system operates similar to the systems described in FIG. 4, FIG. 6, FIG. 8, and FIG. 12 to measure a medical parameter. The sensor of system 1800 is capacitor 1802. Capacitor 1802 is a variable capacitor that varies with the medical parameter being measured. A capacitance value of capacitor 1802 correlates to a value of the parameter. In a first example, the parameter being measured is temperature. The capacitance of capacitor 1802 is coupled to the temperature to be measured. The capacitance of capacitor 1802 at "temperature" can be accurately measured by system 1800 and correlated back to a temperature value. Another example of a parameter is a force, pressure, or load. In one embodiment, the force, pressure, or load can be applied to capacitor 1802. The capacitance of capacitor 1802 at the "force, pressure, or load" is measured by system 1800 and correlated back to a force, pressure, or load value. In either example, the capacitance will change by a known manner over the parameter measurement range. In general, the change in capacitance over the parameter measurement range occurs in a regular manner. Irregularities in capacitance change within the parameter System 1800 can be calibrated over the parameter measurement range to account for any irregularities in capacitance change or to further refine measurement accuracy.

System 1800 comprises a capacitor 1802, a signal generator 1804, a digital clock 1806, a digital counter 1808, a digital timer 1810, a counter register 1812, and a data register 1814. Signal generator 1804 is coupled to capacitor 1802 and has an output for providing a signal. Signal generator 1804 generates a signal 1816 or waveform that corresponds to the capacitance of capacitor 1802. The signal 1816 changes as the capacitance of capacitor 1802 changes. For example, a time period of a measurement cycle of signal 1816 can relate to the capacitance of capacitor 1802.

In one embodiment, signal generator 1804 is an oscillator. A digital clock 1806 is coupled to digital counter 1808 and digital timer 1810. Digital clock 1806 provides a clock signal to digital counter 1808 and digital timer 1810 during a measurement sequence. Digital counter 1808 couples to counter register 1812 and couples to the output of signal generator 1804. Counter register 1812 provides a predetermined count corresponding to the measurement sequence. In general, measurement accuracy can be increased by raising the predetermined count. Digital counter 1808 receives the predetermined count from counter register 1812. After initiating the measurement sequence the digital counter compares the number of measurement cycles at the output of signal generator 1804 to the predetermined count. The measurement sequence ends when the count of measurement cycles equals the predetermined count. In one embodiment, each measurement cycle output by signal generator 1804 decrements digital counter 1808 until a zero count is reached which signifies an end of the measurement sequence. Digital timer 1810 measures a time period of the measurement sequence. In other words, digital timer 1810 measures an elapsed time required for signal generator 1804 to output the predetermined count of measurement cycles. Data register 1814 couples to digital timer 1810 and stores a value corresponding to the time period or elapsed time of the measurement sequence. The elapsed time of the measurement sequence corresponds to a statistically large number of measurements of capacitor 1802. The elapsed time corresponds to an aggregate of the predetermined count of measurement cycles or capacitance measurements. The value stored in data register 1814 can be a translation of the elapsed time to a force, pressure, or load value. The parameter being measured should produce a stable capacitance value during the time period of the measurement sequence.

Figure 19:
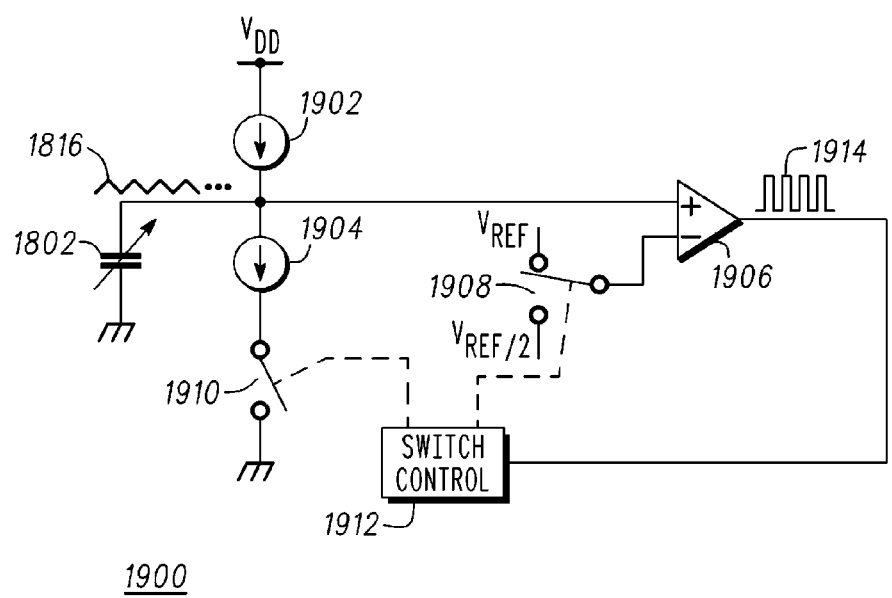
FIG. 19 illustrates an oscillator configured to generate a measurement cycle corresponding to a capacitor in accordance with an example embodiment.

FIG. 19 illustrates an oscillator 1900 generating a signal corresponding to a capacitor 1802 in accordance with an example embodiment. Oscillator 1900 corresponds to signal generator 1804 of FIG. 18. Oscillator 1900 is an example of a circuit used to generate signal 1816 of FIG. 18. Oscillator 1900 comprises a current source 1902, a current source 1904, a comparator 1906, a switch 1908, a switch 1910, and a switch control 1912. Capacitor 1802 is coupled to current sources 1902 and 1904. Current sources 1902 and 1904 respectively source and sink current from capacitor 1802. Current source 1902 sources a current I. Current source 1904 sinks a current 2I or twice the current provided by current source 1902. Switch 1910 enables current source 1904 to sink current when coupled to ground. Comparator 1906 includes a positive input coupled to capacitor 1802, a negative input coupled to switch 1908, and an output. The output of comparator 1906 couples to switch control 1912. Switch control 1912 couples to switches 1908 and 1910 to control switch position. The output of comparator 1906 is a control signal to switch control 1912.

In general, current sources 1902 and 1904 respectively charge and discharge capacitor 1802. Capacitor 1802 is charged by current source 1902 when the output of comparator 1906 is in a low state. Switch control 1912 opens switch 1910 and a reference voltage Vref is coupled to the negative input of comparator 1906 by switch 1908 when the output of comparator 1906 transitions to the low state. The voltage on capacitor 1802 rises as the current I from current source 1902 charges the capacitance. The slew rate of the change in voltage on the capacitor is related to the capacitance of capacitor 1802 and the current I. The output of comparator 1906 transitions from a low state to a high state when the voltage on capacitor 1802 is greater than or equal to the reference voltage Vref. Switch control 1912 closes switch 1910 and a reference voltage Vref/2 is coupled to the negative input of comparator 1906 by switch 1908 when the output of comparator 1906 transitions to the high state. The sink current of current source 1904 is 2I or twice as large as the current sourced by current source 1902. Current source 1904 sinks a current I from capacitor 1802 and an equal current from current source 1902. The voltage on capacitor 1802 falls as charge is removed. The output of comparator changes from the high state to a low state when the voltage on the capacitor is less than or equal to the reference voltage Vref/2. In the example, voltage on capacitor 1802 will transition between the reference voltages Vref and Vref/2. The slew rate of the rising edge and falling edge of the capacitor voltage is symmetrical. A repeating saw tooth pattern is generated by oscillator 1900 until the sequence is stopped. A measurement cycle corresponds to the time to generate a single triangle shaped waveform. The triangle shaped waveform constitutes the time to transition the voltage on capacitor 1802 from Vref/2 to Vref and from Vref to Vref/2. It should be noted that the measurement cycle relates to the capacitance of capacitor 1802. Increasing the capacitance of capacitor 1802 correspondingly increases the measurement cycle. Conversely, decreasing the capacitance of capacitor 1802 correspondingly decreases the measurement cycle. The signal at the output of the comparator 1906 also corresponds to signal 1816. Thus, a relation is established by the signal output by oscillator 1900 to the capacitance of capacitor 1802.

Referring briefly to FIG. 1, a sensor 100 is coupled to the muscular-skeletal system. In the example, a prosthetic knee joint is illustrated and the sensor 100 is coupled to the knee region. Sensor 100 can be capacitor 1802 coupled to the muscular-skeletal system. Capacitor 1802 can be coupled to an articular surface of the prosthetic knee joint to measure a force, pressure, or load. In one embodiment, the force, pressure, or load applied to the articular surface is coupled to capacitor 1802 whereby the capacitance varies with the force, pressure, or load applied thereto. Although a knee joint is shown, capacitor 1802 and system 1800 of FIG. 18 can be used in medical devices, tools, equipment, and prosthetic components to measure parameters that affect capacitance of capacitor 1802. Similarly, although a knee joint is described as an example, capacitor 1802 can be integrated into muscular-skeletal medical devices, tools, equipment, and prosthetic components to measure an applied force, pressure, or load. Moreover, capacitor 1802 and system 1800 of FIG. 18 is not limited to the knee but can be integrated into prosthetic components for parameter measurement such as bone, tissue, shoulder, ankle, hip, knee, spine, elbow, hand, and foot.

Referring back to FIGS. 18 and 19, signal generator 1804 outputs a repeating waveform that corresponds to the capacitance of capacitor 1802. Oscillator 1900 is an implementation of signal generator 1804 that oscillates or generates a repeating waveform. In the example, oscillator 1900 outputs a repeating sawtooth waveform that has symmetrical rising and falling edges. The measurement cycle of the waveform is the time required to transition from Vref/2 to Vref and transition back to Vref/2. The time of the measurement cycle corresponds to the capacitance of the capacitor. The time of each measurement cycle will be substantially equal if the capacitance of capacitor 1802 remains constant during the measurement sequence. In one embodiment, counter register 1812 is loaded with a predetermined count. The measurement sequence can be initiated at a predetermined point of the waveform. For example, a voltage Vref/2 can be detected to start on the waveform to start the measurement sequence. Each subsequent time the voltage Vref/2 is detected the digital counter 1808 is decremented. The measurement sequence ends when digital counter decrements to zero. Digital timer 1810 measures the elapsed time of the measurement sequence corresponding to the predetermined count of measurement cycles of the sawtooth waveform. Alternatively, the output of comparator 1906 can be used as the oscillating or repeating waveform. A rising or falling edge of the output of comparator 1906 can be used to initiate and decrement digital counter 1808. The measurement sequence is configured to be initiated during a period when the parameter to be measured and by relation the capacitance of capacitor 1802 is substantially constant. The process measures the capacitance 1802 a number of times equal to the predetermined count. Variations in the measurement can be averaged out by having a large predetermined count. The process also allows for very small changes in capacitance to be measured very accurately. The accuracy of the measurement can be increased by raising the predetermined count of the measurement cycles. In one embodiment, the measured capacitance is an average determined by the measured elapsed time and the predetermined count of measurement cycles. The measured capacitance can be translated to the parameter being measured such as a force, pressure, or load. Data register 1814 can be configured to store the parameter measurement or a number corresponding to the parameter measurement.

Figure 20:
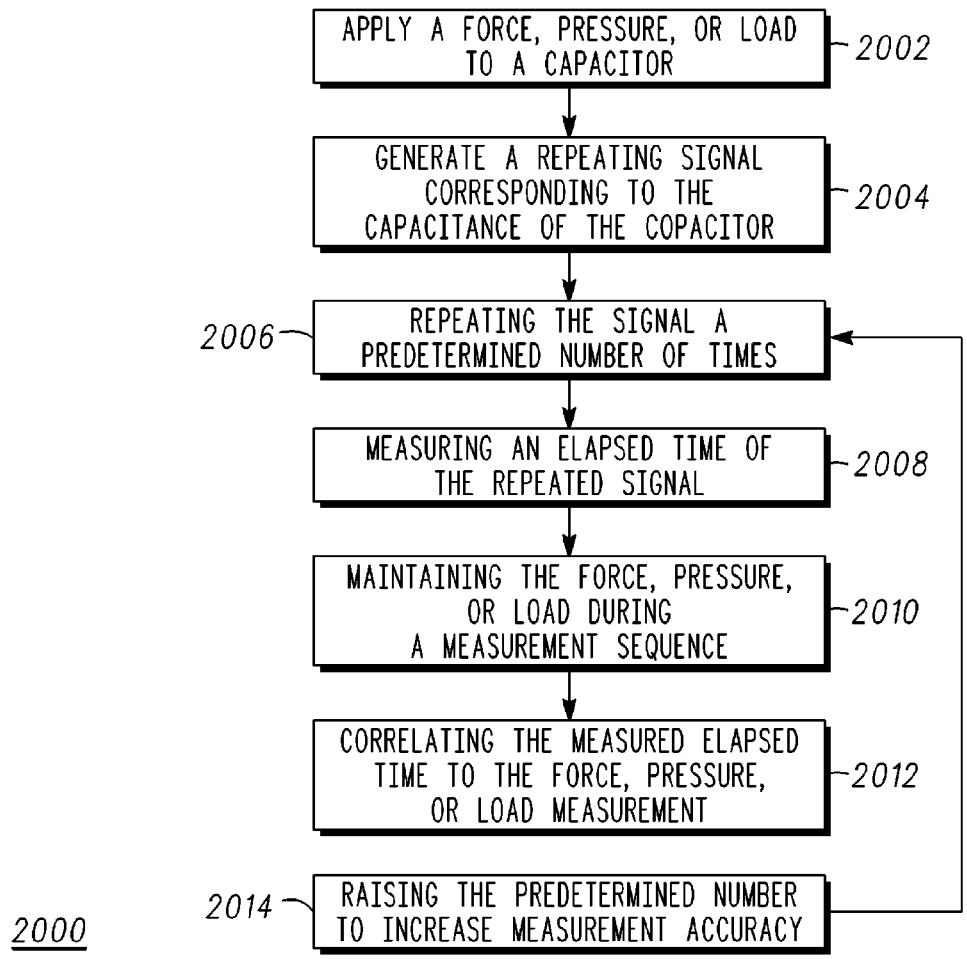
FIG. 20 illustrates a method of force, pressure, or load sensing in accordance with an example embodiment.

FIG. 20 discloses a method 2000 for measuring a force, pressure, or load. The method description relates to and can reference FIGS. 1, 4, 6, 8, 12, 13, and 19. The example disclosed herein uses a prosthetic component implementation but method 2000 can be practiced in any other suitable system or device. The steps of method 2000 are not limited to the order disclosed. Moreover, method 2000 can also have a greater number of steps or a fewer number of steps than shown.

At a step 2002, a force, pressure, or load is applied to a capacitor. Changes in the force, pressure, or load produce a corresponding change in a capacitance of the capacitor. At a step 2004, a repeating signal is generated. A time period of a single waveform of the repeating signal is a measurement cycle. The time period of the measurement cycle corresponds to the capacitance of the capacitor. At a step 2006, the waveform or signal is repeated a predetermined number of times. A measurement sequence comprises the repeated waveform for the predetermined number of times. At a step 2008, an elapsed time of the measurement sequence is measured. The elapsed time is the time required to generate the predetermined number of waveforms. At a step 2010, the force, pressure, or load is maintained during the measurement sequence. In general, the force, pressure, or load coupled to the capacitor should be constant during the measurement sequence. At a step 2012, the measured elapsed time is correlated to the force, pressure, or load measurement. Typically, a measurement range is known for the force, pressure, or load being applied to the capacitor. The capacitor or capacitor type being used can be characterized using known force, pressure, and loads throughout the measurement range prior to use. Thus, a correlation between capacitance and force, pressure, or load is known. For example, the relationship between capacitance and force, pressure, or load can be stored in a look up table or by a mathematical expression. In one embodiment, the capacitor responds approximately linear throughout the measurement range. The average capacitance of the capacitor can be calculated using the measured elapsed time to generate the predetermined number of waveforms during the measurement sequence. The force, pressure, or load can then be determined from the previous characterization. Further refinement can be achieved by using calibration techniques during final testing of the capacitor. The calibration data on the capacitor can be used in the calculation of the force, pressure, or load to further reduce measurement error. At a step 2014, the predetermined number of waveforms can be increased to raise measurement accuracy. The measurement resolution can be increased by this technique if the force, pressure, or load is substantially constant over the increased number of predetermined number waveforms. Moreover, the resolution supports measurement where the capacitance changes are relatively small over the force, pressure, or load measurement range.

Figure 21:
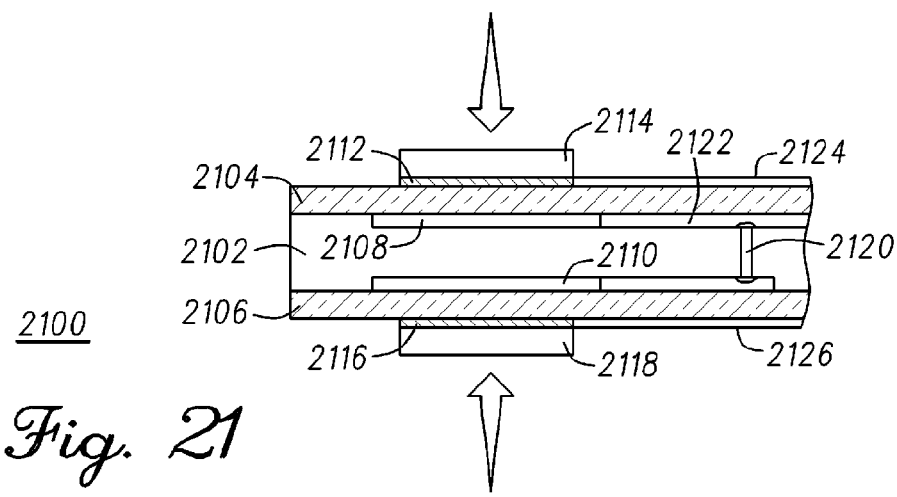
FIG. 21 illustrates a cross-sectional view of a capacitor in accordance with an example embodiment.

FIG. 21 illustrates a capacitor 2100 in accordance with an example embodiment. In general, a sensor for use in a medical environment is accurate, reliable, low cost, and have a form factor suitable for the application. Sensors that produce an electrical signal require a wired or wireless interconnect to electronic circuitry to receive, analyze, and provide the measurement data. Capacitor 2100 meets the above listed requirements. Capacitor 2100 can be used in medical devices, tools, and equipment for measurement of different medical parameters. In the example, capacitor 2100 can be integrated into devices, tools, equipment, and prosthetic components for measuring parameters of the muscular-skeletal system. Capacitor 2100 is suitable for intra-operative and implantable prosthetic components that support installation and long-term measurement of the installed structures.

Figure 22:
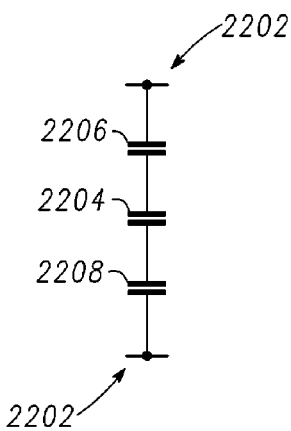
FIG. 22 illustrates the capacitor of FIG. 21 comprising more than one capacitor coupled mechanically in series in accordance with an example embodiment.

Capacitor 2100 comprises a dielectric layer 2102, a dielectric layer 2104, and a dielectric layer 2106. Capacitor 2100 comprises more than two capacitors in series mechanically. In one embodiment, capacitor 2100 comprises 3 capacitors in mechanical series. Referring briefly to FIG. 22, capacitor 2100 of FIG. 21 comprises capacitors 2206, 2204, and 2208. Capacitors 2206, 2204, and 2208 are coupled mechanically in series. A compressive force, pressure, or load 2202 is applied to the series coupled capacitors 2206, 2204, and 2208. Referring back to FIG. 21, a first capacitor comprises a conductive region 2108, dielectric layer 2102, and conductive region 2110. The first capacitor corresponds to capacitor 2204 of FIG. 22. Conductive regions 2108 and 2110 have a predetermined area such that the predetermined area, dielectric constant of dielectric layer 2102, and the thickness of dielectric layer 2102 determine the capacitance of capacitor 2204. In one embodiment, conductive layer 2108 overlies, has substantially equal area, and is aligned to conductive layer 2110.

A second capacitor comprises conductive region 2108, dielectric layer 2104, and a conductive region 2112. The second capacitor corresponds to capacitor 2206 of FIG. 22. In one embodiment, conductive region 2112 overlies, has approximately equal area, and is aligned to conductive region 2108. A load pad 2114 is formed overlying conductive region 2112. Load pad 2114 protects and prevents damage to conductive layer 2112 due to a force, pressure or load applied to capacitor 2100.

A third capacitor comprises conductive region 2110, dielectric layer 2106, and a conductive layer 2116. The third capacitor corresponds to capacitor 2208 of FIG. 22. In one embodiment, conductive region 2116 overlies, has approximately equal area, and is aligned to conductive region 2110. A load pad 2118 is formed overlying conductive region 2116. Load pad 2118 protects and prevents damage to conductive layer 2116 due to a force, pressure or load applied to capacitor 2100. In general, load pads 2114 and 2118 comprise a non-compressible material. Load pads 2114 and 2218 can comprise metal, composite material, or a polymer.

Figure 23:
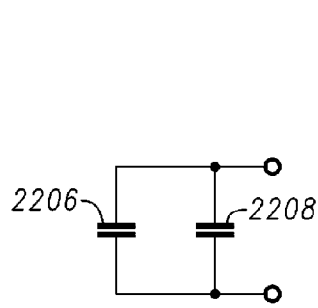
FIG. 23 illustrates the capacitor of FIG. 21 comprising more than one capacitor coupled electrically in parallel in accordance with an example embodiment.

Capacitor 2100 couples to electronic circuitry as disclosed in FIG. 18. Capacitor 2100 can comprise more than one capacitor in parallel. In one embodiment, conductive regions 2108 and 2110 can be coupled in common. In the example, conductive regions 2108 and 2110 are coupled in common by conductive via 2120. Conductive regions 2112 and 2116 are also coupled in common or to a common voltage potential. In one embodiment, conductive regions 2112 and 2116 are coupled to ground forming a shield. Referring briefly to FIG. 23, capacitor 2100 comprises capacitors 2206 and 2208. Capacitors 2206 and 2208 are coupled electrically in parallel having a terminal coupled to ground and a terminal comprising conductive regions 2108 and 2110 coupled in common. Capacitor 2204 is not shown in the electrical equivalent circuit of capacitor 2100 because the conductive regions of capacitor 2204 are shorted together. Referring back to FIG. 21, capacitor 2206 and capacitor 2208 can be formed having substantially equal capacitance. Thus, capacitor 2100 comprises more than one capacitor that are mechanically in series and comprises more than one capacitor that are coupled electrically in parallel.

In the example, capacitor 2100 can be used as a force, pressure, or load sensor for the muscular-skeletal system. Capacitor 2100 can be integrated into a prosthetic component to measure the force, pressure, or load applied by the muscular-skeletal system. The measurement has supports the installation of prosthetic components and can be used for long-term data collection on the implanted system. The size and shape of capacitor 2100 is beneficial to biological sensing applications. The form factor of capacitor 2100 can be made very small. Moreover, capacitor 2100 can be made very thin which supports integration and placement in regions of the body that could not be achieved with conventional sensors. A thickness of less 2.5 millimeters and typically less than 1 millimeter for capacitor 2100 can be manufactured.

In one embodiment, a multi-layered interconnect can be used to form capacitor 2100. Multi-layer interconnect comprises alternating conductive layers and dielectric layers. The conductive layers can be patterned to form conductive regions and interconnect. Applying a force, pressure, or load to multilayer interconnect can deform the dielectric layers. It has been found that for small deformations the dielectric layers of interconnect will rebound elastically when the stimulus is removed. Deformation of the dielectric layer changes the dielectric thickness of capacitor 2100 and the capacitance value thereof. System 1800 of FIG. 18 supports high resolution of small changes in capacitance that makes the use of capacitor 2100 viable.

In general, the dielectric material for the interconnect can comprise a polymer, polyester, an aramid, an adhesive, silicon, glass, or composite material. Capacitor 2100 includes at least one dielectric layer comprising polyimide. In one example, dielectric layers 2102, 2104, and 2106 comprise polyimide. Alternatively, layer 2102 can be an adhesive layer that couples capacitors 2206 and 2208 together. Under testing, polyimide has been shown to compress elastically under load values typical for prosthetic component load measurement. In general, capacitor 2100 compresses less than 20% of thickness of each capacitor to maintain operation in an elastic region of the dielectric. In one embodiment, the dielectric of capacitor 2100 is compressed less than 10% of the dielectric thickness over the operating range. For example, the polyimide layer can be approximately 0.0254 millimeters thick. Compression of the polyimide can be less than 0.0022 millimeters over the entire load measurement range for a prosthetic knee application. The interconnect can be flexible allowing placement on non-planar regions. Moreover, capacitor 2100 can be conformal to different surface shapes if required. Alternatively, capacitor 2100 can be formed as a compressible structure that does not flex or conform.

As mentioned previously, capacitor 2100 is coupled to electronic circuitry such as that disclosed in FIG. 18. Using interconnect to form capacitor 2100 provides the further benefit of being able to integrate capacitor 2100 with the interconnect that couples to the electronic circuitry. This eliminates a connection between the sensor and the interconnect as they are formed as a single structure. The integrated capacitor and interconnect also increases sensor reliability, lowers cost, and simplifies assembly.

Figure 24:
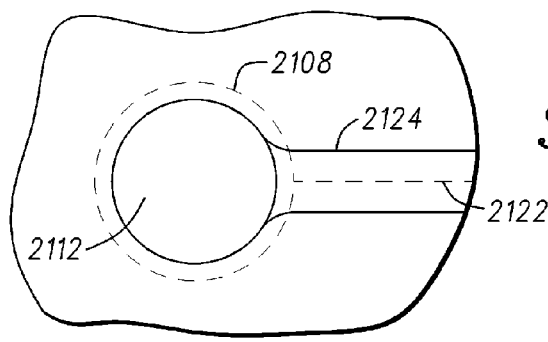
FIG. 24 illustrates a top view of a conductive region of the capacitor of FIG. 21 and interconnect thereto in accordance with an example embodiment.

Referring briefly to FIG. 24, a top view illustrates conductive region 2112 formed overlying dielectric layer 2104. In general, the force, pressure, or load is applied uniformly on the conductive regions of the sensor capacitor. The load pad can support the distribution of the force, pressure, or load across the entire conductive region. The area of the conductive region is of sufficient size to maintain elastic compression of the dielectric material over the entire force, pressure, or load range of the application. The area of the conductive regions can be increased to reduce the force, pressure, or load per unit area thereby lowering dielectric compression over the measurement range for improved reliability. In the knee prosthetic component example, conductive region 2112 can have a circular shape. The area of conductive region 2112 is a function of the force, pressure, or load range being measured. The diameter of conductive region 2112 is approximately 2.0 millimeters for a sensor for a knee application. The dashed line indicates a periphery of conductive region 2108 that underlies conductive region 2112. In the example, conductive region 2108 has a diameter of approximately 2.2 millimeters. More than one of the sensors can fit within a prosthetic component of the knee. An interconnect 2124 is coupled to conductive region 2112. Interconnect 2124 can be formed on the same layer as conductive region 2112. Referring back to FIG. 21, conductive region 2116 can have a similar circular shape as conductive region 2112. The diameter of conductive region 2116 is approximately 2.0 millimeters for a sensor for a knee application. The conductive region 2110 that overlies conductive region 2112 is approximately 2.2 millimeters in diameter. An interconnect 2126 can be formed overlying the polyimide layer 2106 and couple to conductive region 2116.

In the example, a force, pressure, or load is applied by the muscular-skeletal system to load pads 2114 and 2118. The force, pressure, or load compresses capacitors 2206, 2204, and 2208 that are mechanically in series that comprise capacitor 2100. Dielectric layers 2202, 2204, and 2206 compress under the force, pressure, or load. The plates of capacitor 2204 are coupled in common and do not contribute to a capacitance of capacitor 2100. The structure of capacitor 2100 minimizes the effect of parasitic capacitance. Conductive regions 2112 and 2116 are coupled to ground. Conductive regions 2112 and 2116 respectively overlie and underlie conductive regions 2108 and 2110 thereby acting as a ground shield. The shield minimizes or blocks external capacitive interaction that could occur with conductive regions 2112 and 2116 that can effect measurement accuracy.

Figure 25:
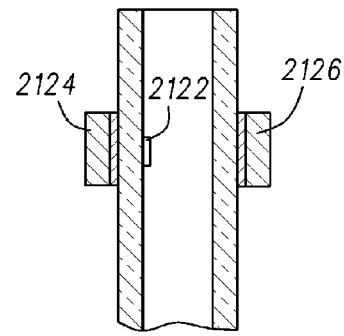
FIG. 25 illustrates a cross-sectional view of the interconnect coupled to the capacitor of FIG. 21 in accordance with an example embodiment.

Referring briefly to FIG. 25, a cross-sectional view of interconnect 2122, 2124, and 2126 in an example embodiment is provided. As described hereinabove, conductive regions 2108 and 2110 are coupled in common by via 2120. An interconnect 2122 couples to conductive regions 2108 and 2110. Interconnect 2122, 2124, and 2126 can couple capacitor 2100 to system 1800 of FIG. 18. Interconnect 2124 and 2126 are coupled to ground. Interconnect 2124 and 2126 overlie and underlie interconnect 2122 thereby acting as a shield. In one embodiment, interconnect 2122 has a width less than interconnects 2124 and 2126. Interconnects 2124 and 2126 shield and block potential capacitive interaction with interconnect 2122 as it is routed and coupled to system 1800 of FIG. 18.

Referring back to FIG. 21, parasitic capacitance related to capacitor 2100 remains substantially constant throughout the parameter measurement range. A first parasitic capacitance comprises interconnect 2124, dielectric layer 2104, and interconnect 2122. A second parasitic capacitance comprises interconnect 2126, dielectric layer 2106, and interconnect 2122. The first and second parasitic capacitances add together to increase the capacitance of capacitor 2100. The force, pressure, or load is not applied to first and second parasitic capacitances thereby remaining constant during measurement. Thus, the change in capacitance of capacitor 2100 can be measured by system 1800 over the force, pressure, or load range using the method disclosed herein with secondary affects due to changes in parasitic capacitance being minimized.

Figure 26:
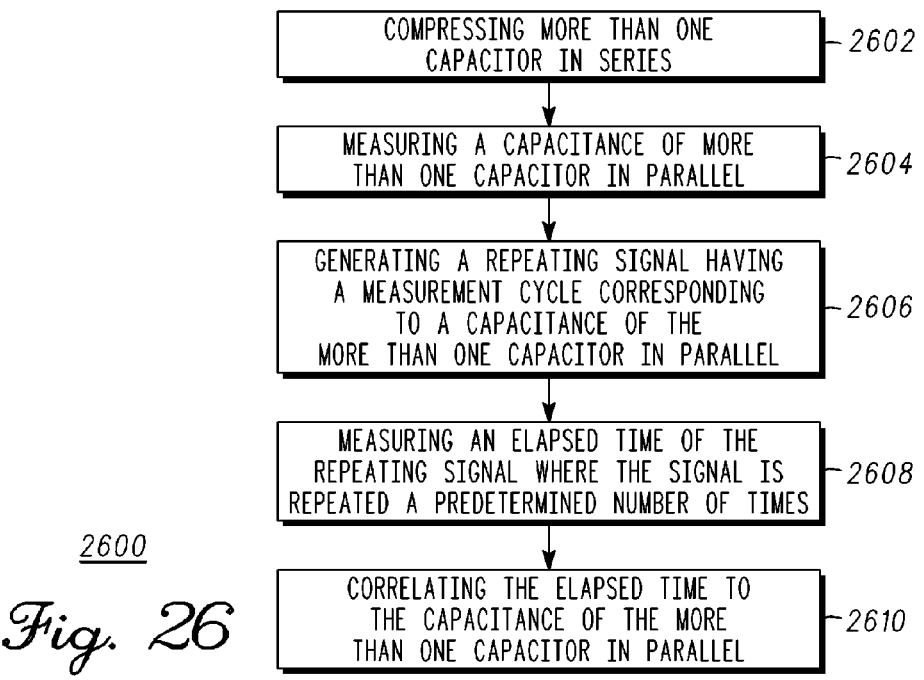
FIG. 26 illustrates a diagram of a method of measuring a force, pressure, or load in accordance with an example embodiment.

FIG. 26 discloses a method 2600 for measuring a force, pressure, or load. The method description relates to and can reference FIGS. 1, 4, 6, 8, 12, 13, 19, and 21-25. The steps of method 2600 are not limited to the order disclosed. Moreover, method 2600 can also have a greater number of steps or a fewer number of steps than shown. At a step 2602, more than one capacitor in series is compressed. A sensor capacitor can comprise more than one capacitor coupled in series. The force, pressure, or load is applied across the series coupled capacitors. At a step 2604, a capacitance of more than one capacitor in parallel is measured. The sensor capacitor can comprise more than one capacitor electrically coupled in parallel.

At a step 2606, a repeating signal is generated having a measurement cycle corresponding to capacitance of the more than one capacitor in parallel. In one embodiment, the more than one capacitor in parallel is coupled to a signal generator circuit. The signal generator circuit coupled to the more than one capacitor in parallel is configured to oscillate. The repeating signal comprises a repeating measurement cycle. A time period of each measurement cycle generated by the signal generator corresponds to the capacitance of the more than one capacitor in parallel.

At a step 2608, an elapsed time is measured of the repeating signal. In one embodiment, the repeating signal is repeated a predetermined number of times. In other words, the measurement cycle is repeated the predetermined number of times and the elapsed time of the predetermined number of measurement cycles is measured. At a step 2610, the elapsed time is correlated to the capacitance of the more than one capacitor in parallel. As disclosed herein, the capacitance of the more than one capacitor in parallel corresponds to the applied force, pressure, or load. Measuring a large number of measurement cycles while the applied force, pressure, or load is substantially constant supports an accurate correlation between capacitance and the force, pressure, or load.

Figure 27:
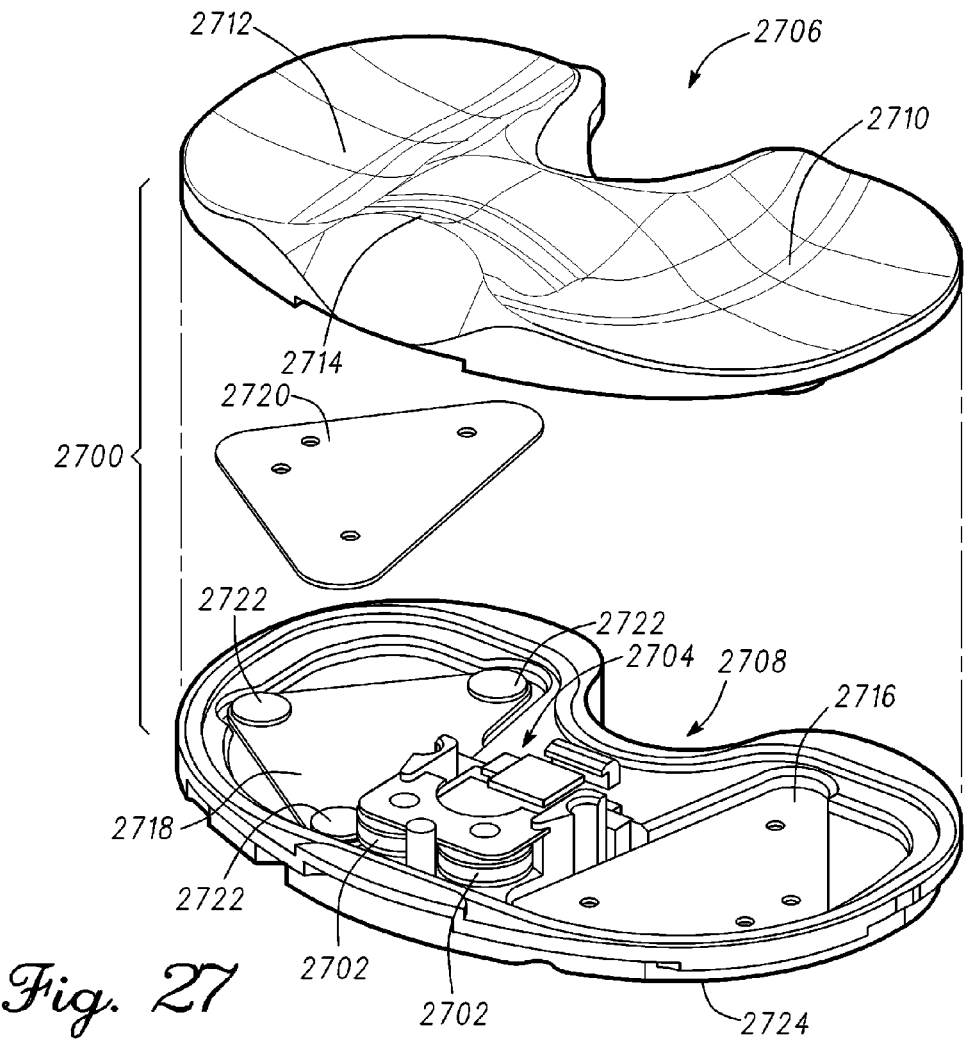
FIG. 27 illustrates a medical device having a plurality of sensors in accordance with an example embodiment.

FIG. 27 illustrates a medical device having a plurality of sensors in accordance with an example embodiment. In general, embodiments of the invention are broadly directed to the measurement of physical parameters. The medical device includes an electro-mechanical system that is configured to measure medical parameters and in the example related to the measurement of the muscular-skeletal system. Many physical parameters of interest within physical systems or bodies are currently not measured due to size, cost, time, or measurement precision. For example, joint implants such as knee, hip, spine, shoulder, and ankle implants would benefit substantially from in-situ measurements taken during surgery to aid the surgeon in the installation and fine-tuning of a prosthetic system. Measurements can supplement the subjective feedback of the surgeon to ensure optimal installation. Permanent sensors in the final prosthetic components can provide periodic data related to the status of the implant in use. Data collected intra-operatively and long term can be used to determine parameter ranges for surgical installation and to improve future prosthetic components.

The physical parameter or parameters of interest can include, but are not limited to, measurement of load, force, pressure, position, displacement, density, viscosity, pH, spurious accelerations, and localized temperature. Often, a measured parameter is used in conjunction with another measured parameter to make a qualitative assessment. In joint reconstruction, portions of the muscular-skeletal system are prepared to receive prosthetic components. Preparation includes bone cuts or bone shaping to mate with one or more prosthesis. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

In the present invention parameters are measured with an integrated wireless sensing module or device comprising an i) encapsulating structure that supports sensors and contacting surfaces and ii) an electronic assemblage that integrates a power supply, sensing elements, an accelerometer, antennas, electronic circuitry that controls and processes a measurement sequence, and wireless communication circuitry. The wireless sensing module or device can be positioned on or within, or engaged with, or attached or affixed to or within, a wide range of physical systems including, but not limited to instruments, equipment, devices, appliances, vehicles, equipment, or other physical systems as well as animal and human bodies, for sensing and communicating parameters of interest in real time.

Sensors are disclosed that can indirectly measure the parameter such as a capacitor having a capacitance that varies with the parameter. The capacitance or related factor (e.g. time) is measured and then converted to the parameter. The measurement system has a form factor, power usage, and material that is compatible with human body dynamics. The physical parameter or parameters of interest can include, but are not limited to, measurement of load, force, pressure, displacement, density, viscosity, pH, distance, volume, pain, infection, spurious acceleration, and localized temperature to name a few. These parameters can be evaluated by sensor measurement, alignment, direction, or position as well as movement, rotation, or acceleration along an axis or combination of axes by wireless sensing modules or devices positioned on or within a body, instrument, appliance, vehicle, equipment, or other physical system.

In the example, an insert 2700 illustrates a device having a medical sensor for measuring a parameter of the muscular-skeletal system. Prosthetic insert 2700 is a component of a joint replacement system that allows articulation of the muscular-skeletal system. The prosthetic insert 2700 is a wear component of the joint replacement system. The prosthetic insert 2700 has one or more articular surfaces that allow joint articulation. In a joint replacement, a prosthetic component has a surface that couples to the articular surface of the insert 2700. The articular surface is low friction and can absorb loading that occurs naturally based on situation or position. The contact area between surfaces of the articulating joint can vary over the range of motion. The articular surface of insert 2700 will wear over time due to friction produced by the prosthetic component surface contacting the articular surface during movement of the joint. Ligaments, muscle, and tendons hold the joint together and motivate the joint throughout the range of motion.

Insert 2700 is an active device having a power source 2702, electronic circuitry 2704, load pads 2722, transmit capability, and sensors within the body of the prosthetic component. Electronic circuitry 2704 includes the circuitry of FIG. 18 and FIG. 19. In the example, sensors underlie load pads 2722. The sensors are capacitors formed in an interconnect 2718 that couples to electronic circuitry 2704. Interconnect 2718 can be flexible and conformal to non-planar shapes. In one embodiment, insert 2700 is used intra-operatively to measure parameters of the muscular-skeletal system to aid in the installation of one or more prosthetic components. As will be disclosed hereinbelow, operation of insert 2700 is shown as a knee insert to illustrate operation and measurement of a parameter such as load and balance. Referring briefly to FIG. 1, a typical knee joint replacement system comprises an insert, femoral prosthetic component 104, and tibial prosthetic component 106. Although housed in the insert, sensor capacitors can also be housed within or coupled to femoral prosthetic component 104 or tibial prosthetic component 106. Referring back to FIG. 27, insert 2700 can be adapted for use in other prosthetic joints having articular surfaces such as the hip, spine, shoulder, ankle, and others. Alternatively, insert 2700 can be a permanent active device that can be used to take parameter measurements over the life of the implant. The sensing system is not limited to the prosthetic component example. The system can also be implemented in medical tools, devices, and equipment.

Insert 2700 is substantially equal in dimensions to a passive final prosthetic insert. The substantially equal dimensions correspond to a size and shape that allow insert 2700 to fit substantially equal to the passive final prosthetic insert in a tibial prosthetic component. In the intra-operative example, the measured load and balance using insert 2700 as a trial insert would be substantially equal to the loading and balance seen by a final passive insert under equal conditions. It should be noted that insert 2700 for intra-operative measurement could be dissimilar in shape or have missing features that do not benefit the trial during operation. Insert 2700 should be positionally stable throughout the range of motion equal to that of the final insert.

The exterior structure of insert 2700 comprises two components. In the embodiment shown, insert 2700 comprises a support structure 2706 and a support structure 2708. Support structures 2706 and 2708 have major support surfaces that are loaded by the muscular-skeletal system. As previously mentioned, insert 2700 is shown as a knee insert to illustrate general concepts and is not limited to this configuration. Support structure 2706 has an articular surface 2710 and an articular surface 2712. Condyles of a femoral prosthetic component articulate with surfaces 2710 and 2712. Loading on the prosthetic knee joint is distributed over a contact area of the articular surfaces 2710 and 2712. Support structure 2708 has a load-bearing surface 2724. The load-bearing surface 2724 couples to the tibial prosthetic component. The loading on load-bearing surface 2724 is much lower than that applied to the articular surfaces due to the larger surface area for distributing a force, pressure, or load.

A region 2714 of the support structure 2706 is unloaded or is lightly loaded over the range of motion. Region 2714 is located between the articular surfaces 2710 and 2712. It should be noted that there is a minimum area of contact on articular surfaces 2710 and 2712 to minimize wear while maintaining joint performance. The contact location and contact area size can vary depending on the position of the muscular-skeletal system. Problems may occur if the contact area falls outside a predetermined area range within articular surfaces 2710 and 2712 over the range of motion. In one embodiment, the location where the load is applied on articular surfaces 2710 and 2712 can be determined by the sensing system. This is beneficial because the surgeon now has quantitative information where the loading is applied. The surgeon can then make adjustments that move the location of the applied load within the predetermined area using real-time feedback from the sensing system to track the result of each correction.

The support structure 2708 can be formed to support the sensors and electronic circuitry 2704 that measure loading on each articular surface of insert 2700. A load plate 2716 underlies articular surface 2710. Similarly, a load plate 2720 underlies articular surface 2712. Interconnect 2718 underlies load plate 2720. Capacitor sensors underlie load pads 2722 in the vertices of the triangular shaped interconnect 2718 in support structure 2708. In one embodiment, the capacitor sensors are formed in the interconnect 2718. Interconnect 2718 couples the sensors to electronic circuitry 2704. A shield is formed in interconnect 2718 that minimizes parasitic capacitance and coupling to ensure accuracy over the measurement range. Load plate 2720 couples to the capacitor sensors through load pads 2722. Load plate 2720 distributes the load applied to articular surface 2712 to the capacitor sensors at predetermined locations within insert 2700. The measurements from the three sensors underlying articular surface 2712 can be used to determine the location of the applied load to insert 2700. Load plate 2716 operates similarly underlying articular surface 2710. Although the surface of load plates 2716 and 2720 as illustrated are planar they can be non-planar with the sensors conforming to the non-planar surface. Similarly, the capacitor sensors can formed having a non-planar shape.

A force, pressure, or load applied by the muscular-skeletal system is coupled to the articular surfaces 2710 and 2712 of prosthetic component insert 2700, which respectively couples to plates 2716 and 2720. In one embodiment, each capacitor elastically compresses due to the force, pressure, or load. Electronic circuitry 2704 is operatively coupled to the capacitor sensors underlying load plates 2716 and 2720. A signal is generated that corresponds to the capacitance of the capacitor being measured. The signal is repeated a predetermined number of times or for a predetermined count. The elapsed time of the predetermined count is measured. The elapsed time corresponds to the capacitance of the capacitor. The relationship between capacitance and force, pressure, or load is known and used to determine the measurement value. Furthermore, the measurement data can be processed and transmitted to a receiver external to insert 2700 for display and analysis.

In one embodiment, the physical location of the sensors and electronic circuitry 2704 is housed in insert 2700 thereby protecting the active components from an external environment. Electronic circuitry 2704 can be located between articular surfaces 2710 and 2712 underlying region 2714 of support structure 2700. A cavity for housing the electronic circuitry 2704 can underlie region 2714. Support structure 2708 has a surface within the cavity having retaining features extending therefrom to locate and retain electronic circuitry 2704 within the cavity. Region 2714 is an unloaded or a lightly loaded region of insert 2700 thereby reducing the potential of damaging the electronic circuitry 2704 due to a high compressive force during surgery or as the joint is used by the patient. In one embodiment, a temporary power source such as a battery, capacitor, inductor, or other storage medium is located within insert 2700 to power the sensors and electronic circuitry 2704.

Support structure 2706 attaches to support structure 2708 to form an insert casing or housing. In one embodiment, internal surfaces of support structures 2706 and 2708 mate together. Moreover, the internal surfaces of support structures 2706 and 2708 can have cavities or extrusions to house and retain components of the sensing system. Externally, support structures 2706 and 2708 provide load bearing and articular surfaces that interface to the other prosthetic components of the joint. The load-bearing surface 2724 of support structure 2708 couples to the tibial prosthetic component. Load-bearing surface 2724 can have one or more features or a shape that supports coupling to the tibial prosthetic component.

The support structures 2706 and 2708 can be temporarily or permanently coupled, attached, or fastened together. As shown, insert 2700 can be taken apart to separate support structures 2706 and 2708. A seal can be located peripherally on an interior surface of support structure 2708. In one embodiment, the seal can be an O-ring that comprises a compliant and compressible material. The O-ring compresses and forms a seal against the interior surface of support structures 2706 and 2708 when attached together. Support structures 2706 and 2708 form a housing whereby the cavities or recesses within a boundary of the seal are isolated from an external environment. In one embodiment support structures 2706 and 2708 are coupled together when the O-ring is compressed sufficiently to interlock fastening elements. Support structures 2706 and 2708 are held together by the fastening elements under force or pressure provided by the O-ring or other means such as a spring.

In one embodiment, support structure 2700 comprises material commonly used for passive inserts. For example, ultra high molecular weight polyethylene can be used. The material can be molded, formed, or machined to provide the appropriate support and articular surface thickness for a final insert. Alternatively, support structures 2706 and 2708 can be made of metal, plastic, or polymer material of sufficient strength for a trial application. In an intra-operative example, support structures 2706 and 2708 can be formed of polycarbonate. It should be noted that the long-term wear of the articular surfaces is a lesser issue for the short duration of the joint installation. The joint moves similarly to a final insert when moved throughout the range of motion with a polycarbonate articular surface. Support structures 2706 and 2708 can be a formed as a composite where a bearing material such as ultra high molecular weight polyethylene is part of the composite material that allows the sensing system to be used both intra-operatively and as a final insert.

Figure 28:
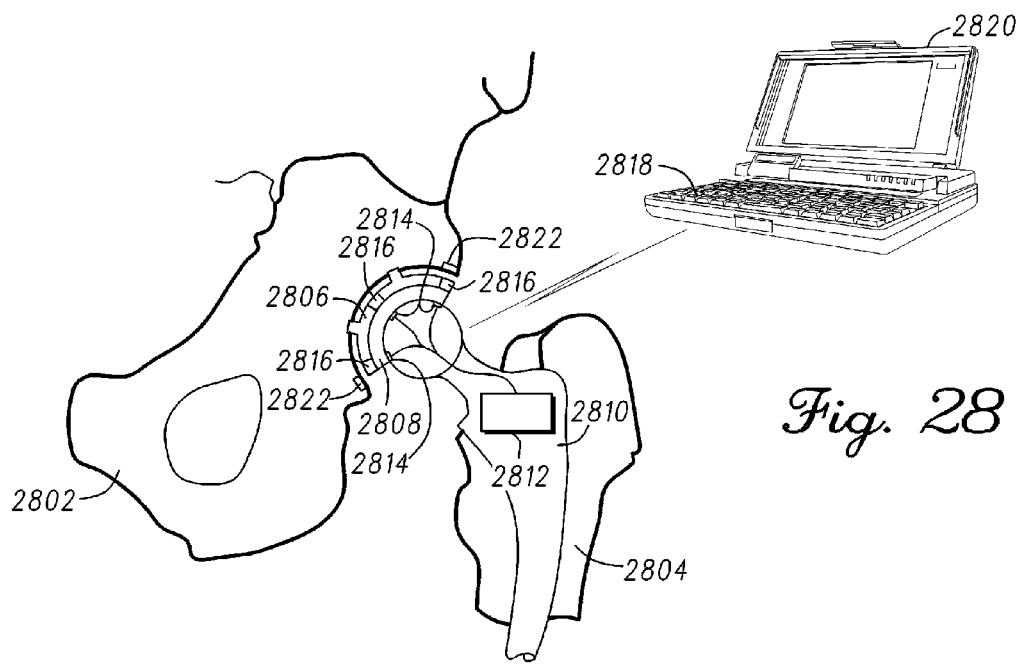
FIG. 28 illustrates one or more prosthetic components having sensors coupled to and conforming with non-planar surfaces in accordance with an example embodiment.

FIG. 28 illustrates one or more prosthetic components having sensors coupled to and conforming with non-planar surfaces in accordance with an example embodiment. Hip joint prosthetic components are used as an example to illustrate non-planar sensors. The hip joint prosthesis comprises an acetabular cup 2806, an insert 2808, and a femoral prosthetic component 2810. The acetabular cup 2806 couples to a pelvis. Cup 2806 can be cemented to pelvis 2802 thereby fastening the prosthetic component in a permanent spatial orientation for receiving femoral prosthetic component 2810. Insert 2808 is inserted into acetabular cup 2806 having an exposed articular surface. A femoral head of femoral prosthetic component 2810 can be placed into insert 2808. Insert 2808 retains the femoral head. The articular surface of insert 2808 couples to the femoral head of femoral prosthetic component 2810 allowing rotation of the joint. The loading is distributed over an area of the articular surface of insert 2808 that varies depending on the leg position. A shaft of femoral prosthetic component 2810 is coupled to a femur 2804. Cement can be used to fasten the shaft of femoral prosthetic component 2810 to femur 2804. Tissue such as tendons, ligaments, and muscle couple to pelvis 2802 and femur 2804 to retain and support movement of the hip joint. The sensors and electronic circuitry disclosed herein are not limited to prosthetic hip components and can be applied similarly to other parts of the anatomy including but not limited to the muscular-skeletal system, bone, organs, skull, knee, shoulder, spine, ankle, elbow, hands, and feet.

In one embodiment, femoral prosthetic component 2810 can house electronic circuitry 2812 thereby protecting the active components from an external environment. The electronic circuitry 2812 can include the circuitry disclosed in FIG. 18 and FIG. 19 to measure capacitance of a capacitor sensor. The electronic circuitry 2812 can further include a power source, power management circuitry, conversion circuitry, digital logic, processors, multiple input/output circuitry, and communication circuitry. The electronic circuitry 2812 can be a module having a form factor that can fit within a prosthetic component. Similarly, electronic circuitry 2812 can be integrated into a tool, device, or equipment. Alternatively, electronic circuitry 2812 can be a separate component that couples through a wired or wireless connection to sensors.

The femoral head of the prosthetic component 2810 is spherical in shape. Capacitors 2814 are sensors that conform and couple to the curved surface of the femoral head. In first embodiment, capacitors 2814 can underlie an external surface of the femoral head. A force, pressure, or load applied to the femoral head couples to and can elastically compress capacitors 2814. Capacitors 2814 and electronic circuitry 2812 are protected from an external environment such that the prosthetic component is suitable for long term monitoring of the joint. In a second embodiment, capacitors 2814 can be exposed on portions of the surface conforming to a spherical shape of the femoral head. In a third embodiment, capacitors 2814 can be formed having the non-planar shape. Capacitors 2814 can be in a trial prosthetic component that is disposed of after a single use. As disclosed herein, capacitors 2814 can be formed in interconnect as disclosed in FIGS. 21-25. The interconnect can be flexible and can conform to non-planar surfaces. In the example, capacitors 2814 are formed in interconnect that couples to electronic circuitry 2812 to receive and process measurement data. The interconnect and more specifically capacitors 2814 are positioned within and coupled to the spherical femoral head surface whereby force, pressure, or loads can be measured at predetermined locations. Thus, the sensor system can be housed entirely within a prosthetic component. Similarly, the sensors can be placed on, within or between acetabular cup 2806 and insert 2808. As an example, capacitors 2816 are shown placed between acetabular cup 2806 and insert 2808. Capacitors 2816 can also underlie or comprise a portion of the articular surface of insert 2808. Similarly, capacitors 2816 can underlie or comprise a portion of the curved surface of acetabular cup 2806. Capacitors 2816 can be configured to measure force, pressure, or load applied to different regions of the articular surface of insert 2808. Electronic circuitry coupled to capacitors 2816 can be in proximity to or housed in acetabular cup 2806, insert 2808. Force, pressure, or load measurements on bone can be supported by the system. Capacitors 2822 can be embedded in bone such as pelvis 2802 to measure forces applied thereto.

In the example, capacitors 2814 are located at predetermined locations of the femoral head of femoral prosthetic component 2810. The capacitance of capacitors 2814 relate to the force, pressure, or load applied to the femoral head by the muscular-skeletal system thereby providing measurement data at the different locations of the femoral head. In one embodiment, measurement data from capacitors 2814 can be wirelessly transmitted to a remote system 2818 in real-time. Remote system 2818 includes a display 2820 configured to display the measurement data. Remote system 2818 can be a computer that further processes the measurement data. The measurement data can be provided in an audible, visual, or haptic format that allows the user to rapidly assess the information. Rotating and moving the leg over the range of motion can provide quantitative data on how the loading varies over the range of motion of the hip joint for the installation. The leg movement couples capacitors 2814 to different areas of the articular surface of insert 2808. Capacitors 2814 move in an arc when the leg is moved in a constant plane. The measurements data can indicate variations in loading that can require modification to the joint installation. The installation can be done in workflow steps that are supported by remote system 2818. Moreover, clinical evidence from quantitative measurements over a statistically significant number of patients as target values or ranges for an optimal fit. The surgeon can further fine-tune the installation based on the actual measured quantitative data and subjective feedback from the patient installation.

Figure 29:
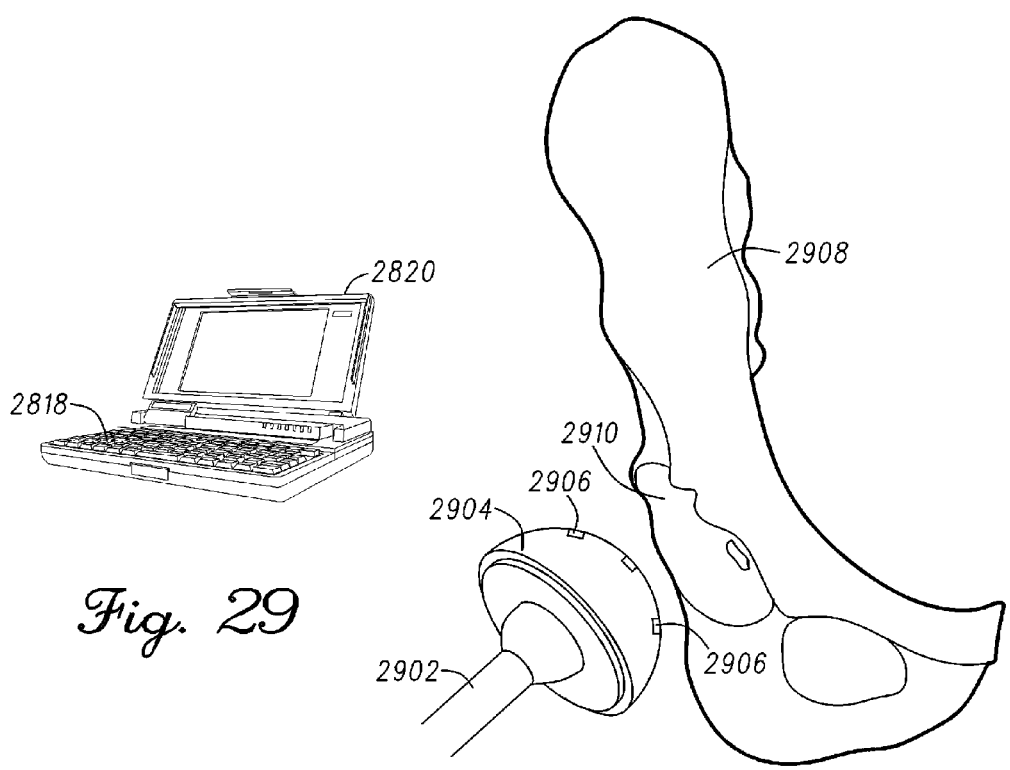
FIG. 29 illustrates a tool having one or more shielded sensors coupled to a non-planar surface in accordance with an example embodiment.

FIG. 29 illustrates a tool having one or more shielded sensors coupled to a non-planar surface in accordance with an example embodiment. A reamer 2902 is used as an example of a medical device, tool, equipment, or component having one or more sensors. Reamer 2902 can be used in a hip prosthetic joint replacement surgery for removing bone in a pelvis 2908 to accept a prosthetic component such as an acetabular cup. Reamer 2902 has spherical shaped surface 2904 having cutting blades or abrasives for removing bone in an acetabular region 2910 to form a spherical shaped bone region. The cutting head of reamer 2902 is sized to cut acetabular region 2910 region substantial equal in dimensions to the acetabular cup to be fitted therein.

In one embodiment, more than one sensor can be coupled to the cutting head of reamer 2902. In a non-limiting example, the sensors can be used to measure a force, pressure, or load. More specifically, the sensors can be positioned corresponding to locations on surface 2904 of the cutting head. The sensors are coupled to surface 2904 but are internal to the cutting head of reamer 2902. The force, pressure, or load is coupled from surface 2904 to the sensors. The sensors provide quantitative data on the force, pressure, or load applied to the different locations of surface 2904. The quantitative data can be used as feedback to the material removal process for optimal fit of the acetabular cup. For example, placing too much force in one direction can result in too much material being removed in a location thereby affecting the shape of the bone cut.

Capacitors 2906 are an example of sensors for measuring a force, pressure, or load. Capacitors 2906 are elastically compressible over the measurable range of reamer 2902. More specifically, the dielectric material comprising capacitors 2906 compresses under an applied force, pressure, or load. The capacitance of a capacitor increases as the dielectric material decreases in thickness due to the force, pressure, or load. Conversely, the dielectric material increases in thickness as the force, pressure, or load applied to the capacitor is reduced thereby decreasing a capacitance value. Capacitors 2906 are coupled to different locations of surface 2904 of the cutting head of reamer 2902. The capacitors 2906 are distributed across surface 2904 to provide force, pressure, or load magnitudes and differential force, pressure, or load magnitudes for different surface regions during a material removal process. The surface regions being measured by capacitors 2906 will change with the trajectory of reamer 2902. The measurement data can be used to support a bone reaming process for optimal prosthetic component fit.

In one embodiment, capacitors 2906 are formed within an interconnect as disclosed in FIGS. 21-25. The interconnect can include one or more dielectric layers or substrates comprising polyimide. The polyimide layers are flexible, can conform to a non-planar surface, or be formed having a predetermined shape. Capacitors 2906 include one or more shields to reduce capacitive coupling to the device. A shield can be coupled to ground and be physically between a conductive region of capacitors 2906 and an external environment of the interconnect. The shield can be a conductive region of the capacitor. In one embodiment, a first shield is formed overlying a conductive region of a capacitor and a second shield is formed underlying the conductive region of the capacitor. The shield minimizes parasitic capacitances that can change a capacitance value of capacitors 2906.

Interconnect can be formed on the one or more polyimide layers that couples to the conductive regions of capacitors 2906. The interconnect can couple capacitors 2906 to electronic circuitry (not shown) for generating a signal corresponding to a capacitance of each capacitor. Capacitors 2906 couple to surface 2904 of the cutting head of reamer 2902. In the example, capacitors 2906 conform to a curved or non-planar surface corresponding to a shape of surface 2904. In one embodiment, the interconnect and capacitors 2906 are internal to the cutting head thereby isolated from an external environment. The interconnect couples to electronic circuitry for measuring capacitance of capacitors 2906. The electronic circuitry can be housed in the cutting head or the handle of reamer 2902. The electronic circuitry can include a power source such as a battery, inductive power source, super capacitor, or other storage medium. As mentioned previously, the capacitance of capacitors 2906 can be related to a force, pressure, or load applied thereto. In the example, the electronic circuitry generates a signal for each capacitor of capacitors 2906 that relates to a capacitance value. The electronic circuitry can include transmit and receive circuitry for sending measurement data from capacitors 2906. In one embodiment, the measured data is transmitted to a remote system 2818. Remote system 2818 can include a display 2820 for presenting the measurement data. Data processing can be performed by remote system 2818 to convert the measurement data to a force, pressure, or load. Trajectory data and force, pressure, or load measurements can be provided in a visual format that allows rapid assessment of the information. Audible feedback can be provided to supplement display 2820 when the user requires direct viewing of an operational area. Remote system 2818 can analyze the quantitative measurement data and transmit information to reamer 2902 that provides haptic or other types of feedback to the device that affects trajectory or force, pressure, or load as directed by the user. Quantitative data provided by reamer 2902 is provided in real-time allowing the user to see how the changes affect bone removal on pelvis 2908 on display 2820.

Figure 30:
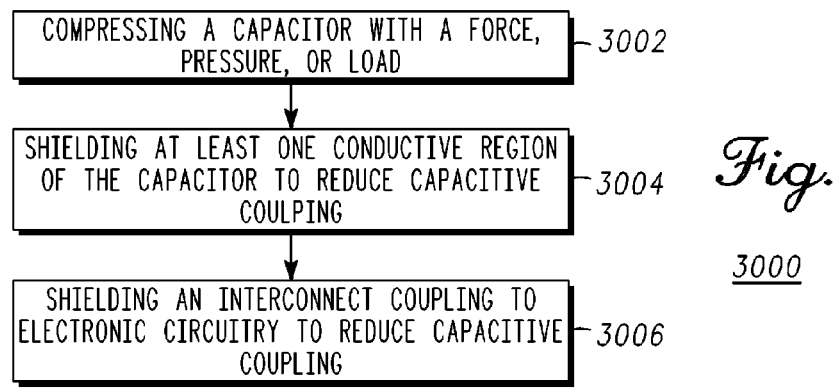
FIG. 30 illustrates a diagram of a method of using a capacitor as a sensor to measure a parameter of the muscular-skeletal system in accordance with an example embodiment.

FIG. 30 discloses a method 3000 for measuring a force, pressure, or load. The method description relates to and can reference FIGS. 1, 4, 6, 8, 12, 13, 19, 21-25, and 27-29. The steps of method 3000 are not limited to the order disclosed. Moreover, method 3000 can also have a greater number of steps or a fewer number of steps than shown. At a step 3002, a force, pressure, or load is applied to a capacitor. Changes in the force, pressure, or load produce a corresponding change in a capacitance of the capacitor. In one embodiment, the capacitor is formed on or in an interconnect. The dielectric material of the capacitor can be elastically compressible. In a step 3004, at least one conductive region of the capacitor is shielded to reduce capacitive coupling. In one embodiment, the shield can comprise a conductive region of the capacitor that is a plate of the capacitor. Alternatively, the shield can be a separate structure. The shield can be grounded to minimize parasitic capacitance or coupling to the capacitor. The shield can be between an external environment of the capacitor and the active conductive region or plate of the capacitor being shielded. Furthermore, the shield reduces variable parasitic capacitance that can affect measurement accuracy. The grounded conductive region can be between the active conductive region and the external environment. In a step 3006, interconnect coupling the capacitor to electronic circuitry is shielded to further reduce capacitive coupling. The shield can be an interconnect of the capacitor. For example, a grounded interconnect can be placed between the interconnect carrying a signal and an external environment to prevent capacitive coupling from circuitry in the external environment. Alternatively, the shield can be a separate structure. Shielding for the capacitor and the interconnect supports the measurement of very small capacitive values. The change in measured capacitance can be small in comparison to the total capacitance. Shielding prevents the total capacitance from changing thereby allowing a capacitance change of less than 10 picofarads to be measured.

Thus, a system is provided herein for measuring small capacitive values and small changes in capacitance. The system further supports a small form factor, high reliability, measurement accuracy, and low cost. Capacitors for force, pressure, and load measurement can be formed in interconnect used to couple the capacitors to electronic circuitry. The capacitors are operated within a substantially elastically compressible region of the dielectric material. Forming the capacitors in the interconnect reduces system complexity, improves reliability, product consistency, and reduces assembly steps.

A signal is generated corresponding to a capacitance of the capacitor under a force, pressure, or load. The signal is repeated for a predetermined count. Measuring an elapsed time of a large number of measurement cycles can be used to generate an average time period of a measurement cycle when change in the parameter being measured occurs slowly in relation to physiological changes such as occurs in the muscular-skeletal system. The measurement data can be analyzed to achieve accurate, repeatable, high precision and high-resolution measurements. The system disclosed herein enables the setting of the level of precision or resolution of captured data to optimize trade-offs between measurement resolution versus frequency, including the bandwidth of the sensing and data processing operations, thus enabling a sensing module or device to operate at its optimal operating point without compromising resolution of the measurements. This is achieved by the accumulation of multiple cycles of excitation and transit time instead of averaging transit time of multiple individual excitation and transit cycles. The result is accurate, repeatable, high precision and high-resolution measurements of parameters of interest in physical systems.

Measurement using elastically compressible capacitors enables high sensitivity and high signal-to-noise ratio. The time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

Furthermore, summing individual capacitive measurements before dividing to estimate the average measurement value data values produces superior results to averaging the same number of samples. The resolution of count data collected from a digital counter is limited by the resolution of the least significant bit in the counter. Capturing a series of counts and averaging them does not produce greater precision than this least significant bit that is the precision of a single count. Averaging does reduce the randomness of the final estimate if there is random variation between individual measurements. Summing the counts of a large number of measurement cycles to obtain a cumulative count then calculating the average over the entire measurement period improves the precision of the measurement by interpolating the component of the measurement that is less than the least significant bit of the counter. The precision gained by this procedure is on the order of the resolution of the least significant bit of the counter divided by the number of measurement cycles summed.

Figure 31:
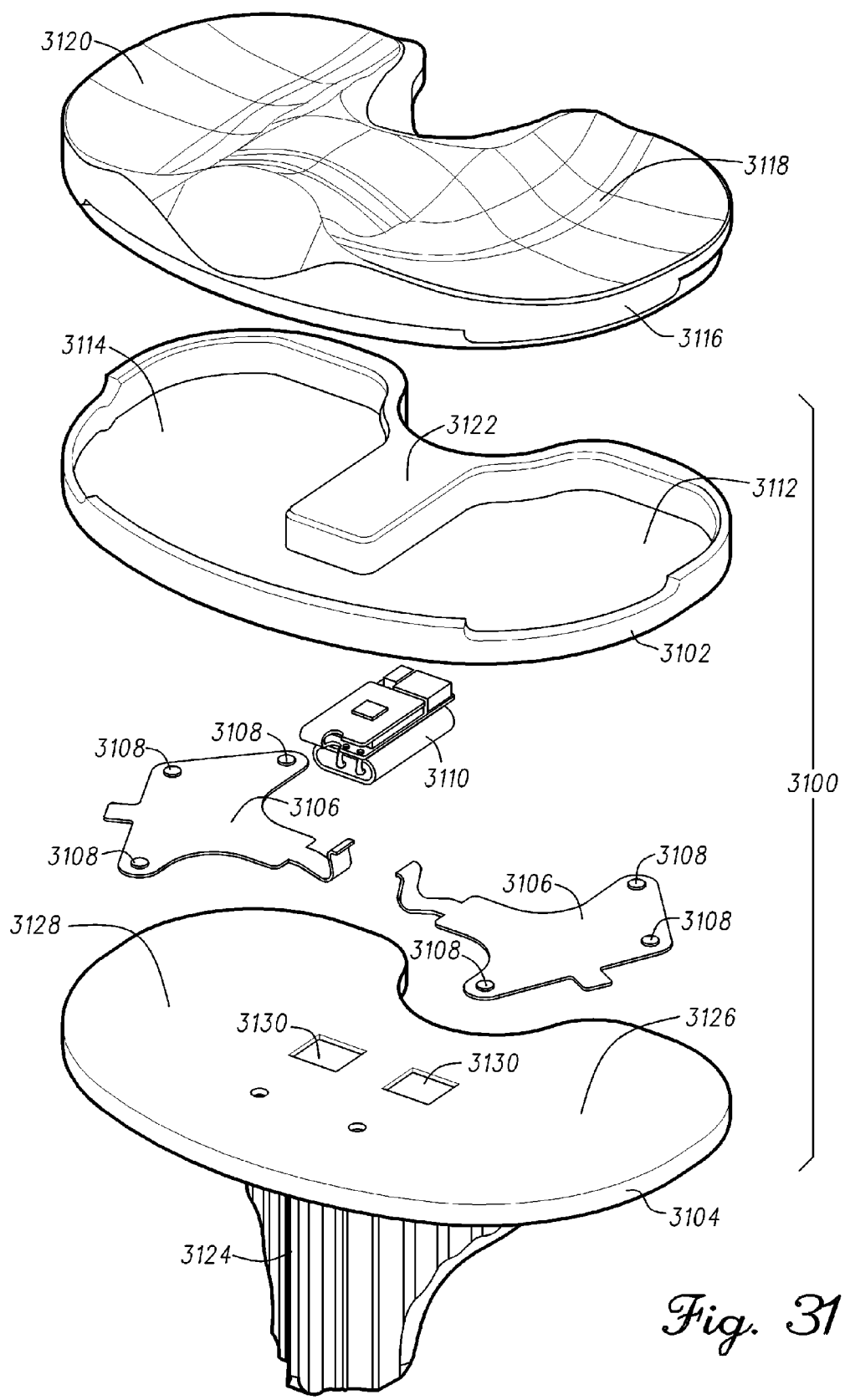
FIG. 31 illustrates a prosthetic component having a plurality of sensors in accordance with an example embodiment.

FIG. 31 illustrates a prosthetic component 3100 having a plurality of sensors in accordance with an example embodiment. In general, there is need for short-term intra-operative sensored prosthetic components that support the installation of a prosthetic joint and prosthetic components. Similarly, there is a need for the prosthetic joint to include sensors to monitor the joint long-term. Prosthetic component 3100 can be used as a trial prosthetic component or as a permanent prosthetic component for long-term use in the body. Prosthetic component 3100 is illustrated as a tibial prosthetic component in the example. Prosthetic component 3100 can be adapted for use in hip, knee, shoulder, spine, ankle, elbow, toe, hand, or bone implants. Prosthetic component 3100 comprises a structure 3102, a structure 3104, interconnect 3106, load pads 3108, and electronic circuitry 3110.

Prosthetic component 3100 typically comprises a metal such as titanium, titanium alloy, cobalt, cobalt alloy, steel, or a steel alloy. The material is suitable for handling the loading produced by the muscular-skeletal system on the joint. Alternatively, the prosthetic component 3100 can be formed of a polymer material. One such suitable material is PEEK (polyether ether ketone). PEEK is a semi-crystalline thermoplastic that has high tensile strength and is resistant to thermal, aqueous, or biological degradation. PEEK can be molded to form the complex shapes required for a prosthetic component. PEEK is light-weight and can be fastened to bone by gluing. PEEK components can be welded together to form a hermetic seal. PEEK has a further benefit that it is transmissive to signals used for communication or for sensor detection.

Structure 3102 includes at least one support surface. As shown structure 3102 includes a support surface 3112 and a support surface 3114. The support surfaces 3112 and 3114 receive an insert 3116. Insert 3116 includes an articular surface 3118 and an articular surface 3120 that support movement of the joint. Articular surfaces 3118 and 3120 respectively overlie support surfaces 3112 and 3114. A force, pressure, or load applied to articular surfaces 3118 and 3120 apply a corresponding force, pressure, or load to support surfaces 3112 and 3114. A lightly loaded region resides between support surface 3112 and 3114. In one embodiment, a housing 3122 is formed in structure 3102 in the lightly load region. Housing 3122 includes a cavity for receiving electronic circuitry 3110 that controls measurement activity of prosthetic component 3100.

Structure 3104 includes at least one feature that couples to bone. In the example, the proximal end of the tibia is prepared to receive structure 3104. A stem 3124 can be inserted into the medullary canal of the tibia. The stem 3124 aligns and supports structure 3104 to the tibia. Structure 3104 can be glued to the tibia to securely fasten prosthetic component 3100 in place. Alternatively, structure 3104 comprising PEEK or a metallic structure can include points supporting bone growth. Structure 3104 would include features that anchor bone and provide bone growth hormone. Bone can grow into and around the prosthetic component fusing structure 3104 to the tibia. Utilizing bone growth for fastening can also be used in conjunction with glue or other bonding agent.

In one embodiment, three sensors comprise a sensor array. There is a sensor array for each knee compartment. Each sensor array is used to measure the load and position of load of a knee compartment. An articular surface 3118 of insert 3116 corresponds to a first knee compartment of prosthetic component 3100. Similarly, an articular surface 3120 of insert 3116 corresponds to a second knee compartment of prosthetic component 3100. A force, pressure, or load applied to articular surfaces 3118 and 3120 is respectively applied to a support surface 3112 and a support surface 3114 of structure 3102. The support surfaces 3112 and 3114 transfer the force, pressure, or load to a corresponding sensor array. The load pads 3108 are at predetermined locations corresponding to articular surfaces 3118 and 3120. Load pads 3108 transfer the force, pressure, or load at the predetermined location to the underlying sensors for measurement. Thus, the force, pressure, or load magnitude and the position of applied force, pressure, or load can be calculated from measurements by the three sensors in the first and second knee compartments. The position of load can be translated back to position on articular surfaces 3118 and 3120. The sensors overlie a support surface 3126 and a support surface 3128 of structure 3104. Support surfaces 3126 and 3128 respectively correspond to the first and second knee compartments. In one embodiment support surfaces 3126 and 3128 are rigid under loading.

Sensors for measuring load can be devices such as an ultrasonic waveguide, piezo-resistive sensor, mems sensor, strain gauge, polymer sensor, mechanical sensor, and capacitive sensor. In the example, the form factor of prosthetic component 3100 limits the height of the sensor. In a passive prosthetic component (e.g. having no sensors) the structure is formed as a single device. The thickness of the support surfaces is approximately 2 millimeters. In general, the combined thickness of support surfaces 3112 and 3114 coupled to support surfaces 3126 and 3128 can be maintained at 2 millimeters or less with the sensor therebetween. Thus, the sensor requires a form factor that is substantially less than 2 millimeters thick. In one embodiment, the sensor is an elastically compressible capacitive sensor. The area of the sensor is determined by the load range to be measured and the compressible range where the sensor remains elastic. As disclosed hereinabove a measurement technique can be applied that is sensitive to small changes in capacitance that allows measurement accuracy, precision, and repeatability. In one embodiment, the elastically compressible capacitors are formed in the interconnect 3106.

Electronic circuitry 3110 can be fitted in the cavity formed by housing 3122 of structure 3102. In one embodiment, the cavity is formed in an unloaded or lightly loaded area of prosthetic component 3100. The unloaded or lightly loaded region of housing 3122 is between the support surfaces 3112 and 3114. Thus, electronic circuitry 3110 is protected from impact forces and loading that occurs under normal operation of the joint. Interconnect 3106 and the sensors therein couple to electronic circuitry 3110. Interconnect 3106 include interconnect that couples the sensors to electronic circuitry 3110. Cavities 3130 are formed on a surface of structure 3104. Cavities 3130 support interconnect 3106 coupling from support surfaces 3126 and 3128 of structure 3104 to electronic circuitry 3110. Cavities 3130 provide a pathway for interconnect 3106 into housing 3122.

In general, structure 3102 couples to structure 3104 to form prosthetic component 3100. In one embodiment, structures 3102 and 3104 are welded together around the periphery to form a hermetic seal. Electronic circuitry 3110, sensors, and interconnect 3106 are housed within prosthetic component 3100 and hermetically sealed from an external environment. Alternatively, structure 3102 and 3104 can be glued or mechanically fastened together to maintain hermeticity. The structure 3102 and 3104 can further include a seal or O-ring that prevents the ingress or egress of gas, liquids, or solids.

Interconnect 3106 respectively couple to support surface 3126 and surface 3128 of structure 3104. As mentioned previously, load pads 3108 couple each sensor to a respective location on support surface 3112 and support surface 3114. In the example, load pads 3108 bound an area in each knee compartment that corresponds to articular surfaces 3118 and 3120 of insert 3116. The force, pressure, or load applied to articular surface 3118 and 3120 is respectively transferred to surface 3112 and 3114 of structure 3102. It should be noted that surface 3112 and surface 3114 are compliant and not rigid. Each surface has sufficient compliance that allows the underlying sensors to compress. In one embodiment, surface 3112 and surface 3114 is thinned or made thin to achieve compliance. The combined thickness of surfaces 3112 or 3114 of structure 3102 and surfaces 3126 or 3128 of structure 3104 can be approximately 2 millimeters. Surface 3112 and 3114 of structure 3102 can be less than 1 millimeter thick to be made compliant. Alternatively, support structures 3112 and 3114 can comprise a material that is compliant such as a polymer material.

In the example, the load applied to each sensor can be calculated. The load magnitude corresponds to the combination of the three individual measurements. The position of applied load can be calculated from the load magnitudes measured at the fixed positions of the sensors. Electronic circuitry 3110 includes multiple channels of input/output circuitry, timing circuitry, conversion circuitry, logic circuitry, power management circuitry, transmit and receive circuitry. Electronic circuitry 3110 can further include memory for storing software programs to operate or control a measurement process. In one embodiment, an ASIC is used to combine the analog and digital circuitry in a low power solution.

The ASIC reduces the form factor of electronic circuitry 3110 allowing it to fit within the housing 3122 of structure 3102. Electronic circuitry 3110 can include the circuitry described herein and the disclosures incorporated by reference. Electronic circuitry 3110 includes transmit circuitry and an antenna for transmitting data from the sensors to a remote system. Electronic circuitry 3110 can further include receive circuitry to receive information and programming instructions from the remote system. The remote system can be a portable device with a display for reporting the data. The remote system can transmit the data to a database for further review and analysis.

FIG. 32 illustrates a cross-sectional view of structure 3102 in accordance with an example embodiment. The cross-sectional view is of the lightly loaded area between the first and second knee compartments. The view includes a portion of housing 3122 overlying electronic circuitry 3110. Housing 3122 protects and isolates electronic circuitry from an external environment.

FIG. 33 illustrates prosthetic component 3100 and insert 3116 in accordance with an example embodiment. Structure 3102 is coupled to structure 3104. In one embodiment, a hermetic seal 3302 is formed that couples structures 3102 and 3104. Structures 3102 and 3104 can have position and alignment features that support assembly. The periphery of structures 3102 and 3104 can be in proximity to one another around the entire perimeter. In one embodiment, structures 3102 and 3104 comprise an alloy of steel or titanium. A hermetic seal 3302 is formed by welding structure 3102 to structure 3104. The weld is circumferential to prosthetic component 3100 sealing the sensors and electronic circuitry from an external environment. Welding joins the metals of structure 3102 to structure 3104 forming a contiguous structure. The sensors and electronic circuitry 3110 are isolated from an external environment completely enclosed within prosthetic component 3100. The weld is formed whereby little or no pressure is applied to the sensors. Any offset due to coupling structures 3102 and 3104 can be compensated for during device calibration. Prosthetic component 3100 is suitable for use as a long-term implant for providing periodic data on joint status. A similar approach could be performed if the structures were formed of PEEK. Alternatively, other approaches using adhesives, mechanical coupling, and seals can be used to join structures 3102 and 3104 together to form a hermetic seal.

Insert 3116 fits into the tray of prosthetic component. The tray of prosthetic component 3100 can have one or more features for retaining insert 3116. Insert 3116 typically comprises a polymer material such as ultra-high molecular weight polyethylene. Articular surfaces 3118 and 3120 interface with another prosthetic component (not shown) of the joint. In the example, articular surfaces 3118 and 3120 would interface with the condyle surfaces of a femoral prosthetic component. Muscles, tendons, and ligaments motivate the prosthetic joint whereby articular surfaces 3118 and 3120 allow movement of the components in relation to one another. Insert 3116 can be a passive component or include one or more sensors.

Figure 34:
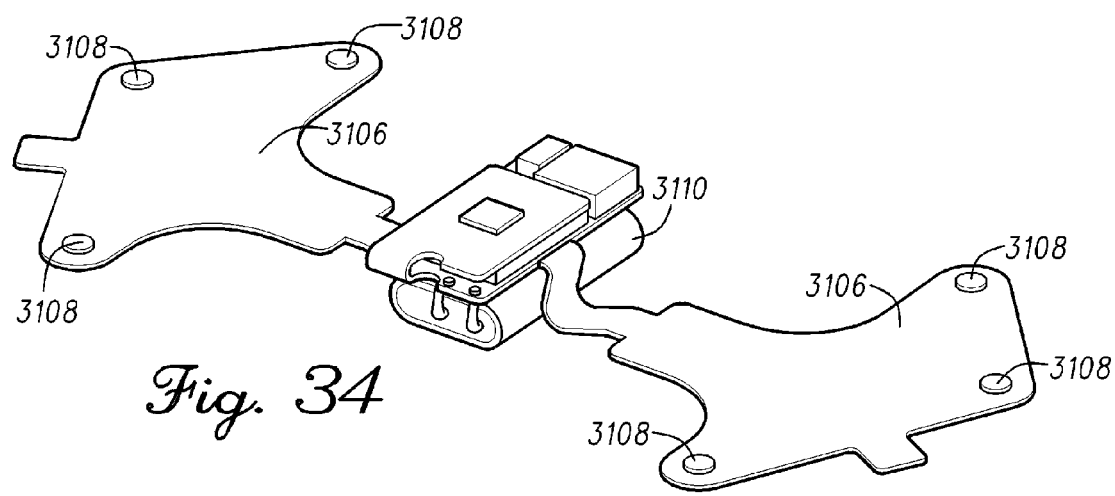
FIG. 34 illustrates electronic circuitry coupled to interconnect in accordance with an example embodiment.

FIG. 34 illustrates electronic circuitry 3110 coupled to interconnect 3106 in accordance with an example embodiment. Electronic circuitry 3110 can include one or more connectors for coupling to interconnect 3106. In one embodiment, the sensors are elastically compressible capacitive sensors. The capacitors are formed underlying load pads 3108 in interconnect 3106. Referring briefly to FIGS. 21-25, the sensor structure is described. Load pads 3108 can comprise a non-conductive material or a conductive material. In the example, load pads 3108 are rigid and non-compressible to transfer the force, pressure, or load to the underlying capacitor. A non-conductive load pad can comprise a polymer material. In one embodiment, load pads 3108 comprise a conductive metal such as copper or copper alloy that is plated onto the surface of interconnect 3106. The conductive load pads 3108 electrically couple to the underlying plate of the capacitor.

In one embodiment, the capacitors can be formed on or in a flexible polyimide substrate. The load pads, capacitors, and interconnect can be formed accurately and repeatably using lithographic techniques. The polyimide substrate can be made very thin suitable for fitting within a prosthetic component. The capacitor is operated within a range where it is elastically compressible. Each capacitor underlying load pads 3108 are similar to capacitor 2100 of FIG. 21. Capacitor 2100 comprises 3 capacitors mechanically in series and 2 capacitors electrically in parallel. The force, pressure, or load is applied across capacitors 2204, 2206, and 2208. In one embodiment, capacitor 2204 is not electrically in the circuit because both plates of capacitor 2204 are coupled in common. Electrically, the sensor capacitor comprises capacitors 2206 and 2208 that are electrically coupled in parallel. In one embodiment, a plate of capacitor 2206 and a plate of capacitor 2208 are coupled to ground. The grounded plates 2112 and 2116 are respectively between an external environment of the interconnect and plates 2108 and 2110. Similarly, the interconnect from capacitor 2100 to the electronic circuitry has a similar topology. Grounded interconnects 2124 and 2126 are between the external environment and the signal carrying interconnect 2122 that couples to plates 2108 and 2110. Thus, parasitic coupling is minimized by the shield. Furthermore, any parasitic capacitance is constant and not variable.

The capacitive magnitude and changes in magnitude can be accurately measured using the circuitry and method disclosed in FIGS. 18 and 19. Referring briefly to FIGS. 33 and 34, a force, pressure, or load is applied to articular surface 3118 and 3120. The force, pressure, or load is transferred from articular surfaces 3118 and 3120 respectively to support surfaces 3112 and 3114. As mentioned previously, support surfaces 3112 and 3114 are compliant such that the force, pressure, or load is transferred through load pads 3108 to the underlying sensors. The sensors are supported by support surfaces 3126 and 3128, which are rigid and non-compliant. A force, pressure, or load applied to a sensor capacitor compresses the structure. The dielectric layer between the capacitor plate is compressed. The capacitance value of the sensor capacitor is related to the thickness of the dielectric layer. Thus, measuring the capacitance and changes in capacitance can be related to the force, pressure, or load applied thereto.

A repeating signal is applied to the sensor capacitor. In general, the sensor is charged and discharged between predetermined voltage levels within a time period. The time period of a single waveform of the repeating signal is a measurement cycle. The time period of the measurement cycle corresponds to the capacitance of the capacitor. The waveform or signal is repeated a predetermined number of times. A measurement sequence comprises the repeated waveform for the predetermined number of times. An elapsed time of the measurement sequence is measured. The elapsed time is the time required to generate the predetermined number of waveforms. The force, pressure, or load is maintained during the measurement sequence. The measured elapsed time of the sensor capacitor is correlated to the force, pressure, or load measurement. The relationship between capacitance and force, pressure, or load is known. In one embodiment, each capacitive sensor can be measured against known force, pressure, or load values after assembly of the prosthetic component. The measurements can be stored in memory that is part of the electronic circuitry housed in the prosthetic component. Further refinement can be achieved by using calibration techniques or algorithms during final testing of each capacitor that can take into account interpolation between measurements and non-linear compression of the dielectric. The measurement resolution can be increased by this technique if the force, pressure, or load is substantially constant over the increased number of predetermined number waveforms. Moreover, the resolution supports measurement where the capacitance changes are relatively small over the force, pressure, or load measurement range.

Figure 35:
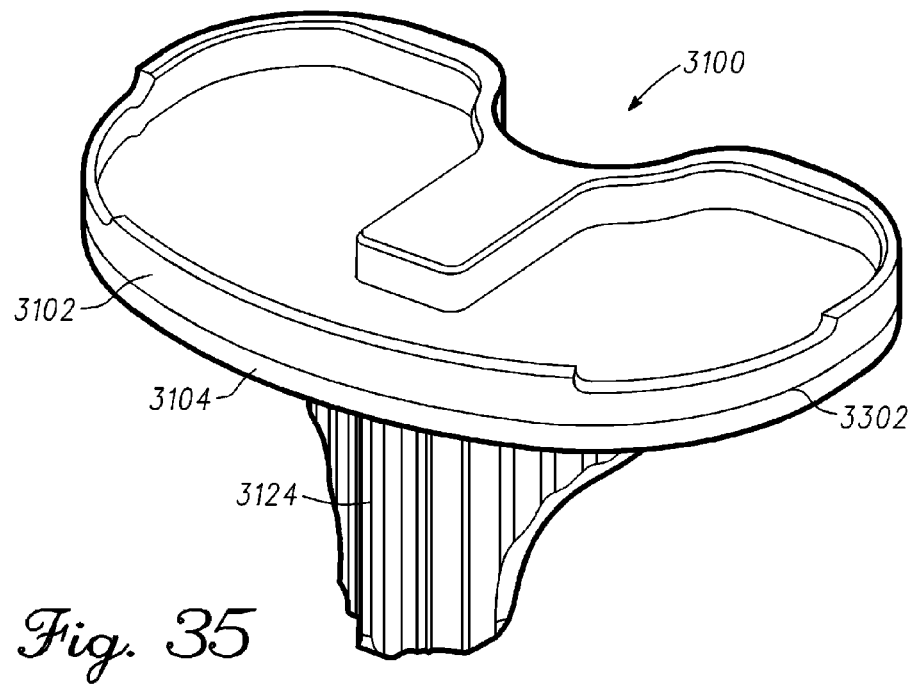
FIG. 35 illustrates an assembled the prosthetic component in accordance with an example embodiment.

FIG. 35 illustrates an assembled prosthetic component 3100 in accordance with an example embodiment. Prosthetic component 3100 comprises structure 3102 coupled to structure 3104. Prosthetic component 3100 houses electronic circuitry and sensors. A hermetic seal 3302 couples the structure 3102 to structure 3104. In one embodiment, hermetic seal 3302 is a contiguous weld around the periphery. As mentioned, weld does not load or lightly loads the sensors underlying the support surfaces. In the example, prosthetic component 3100 is a tibial prosthetic component. Structure 3102 includes a tray for receiving an insert having at least one articular surface. The tibial prosthetic component can be a single or dual compartment device. Structure 3104 includes a stem 3124 for coupling to bone. In the example, stem 3124 couples to the tibia.

Figure 36:
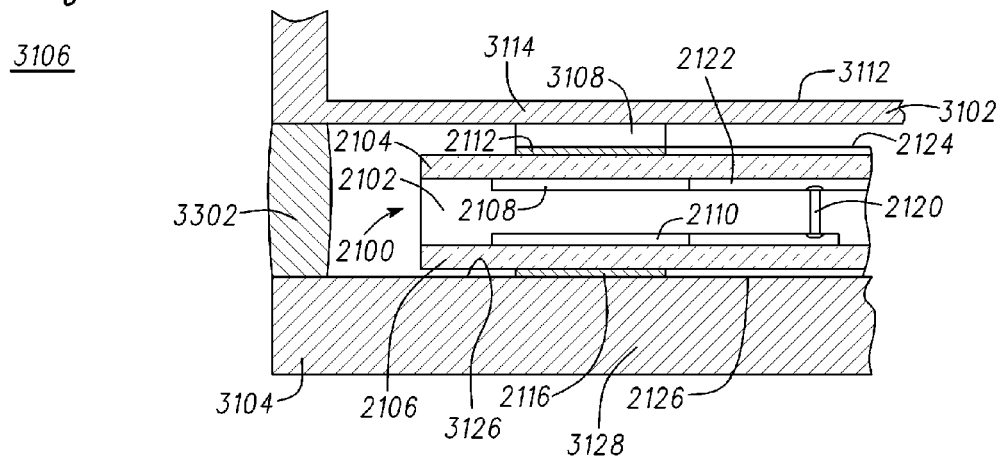
FIG. 36 illustrates a partial cross-sectional view of the prosthetic component in accordance with an example embodiment.

FIG. 36 illustrates a partial cross-sectional view of prosthetic component 3100 in accordance with an example embodiment. The cross-sectional view is in a region near the periphery where hermetic seal 3302 couples structures 3102 and 3104 together. In the example, a sensor 2100 is included. The sensor 2100 is formed in interconnect 3106. A load pad 3108 is formed on sensor 2100. Interconnect 3106 further illustrates shielding of the sensor to minimize signal coupling and parasitic capacitance.

The cross-section illustrates placement of sensor 2100 of prosthetic component 3100 for load sensing. Support surface 3128 of structure 3104 supports sensor 2100. In the example, support surface 3128 is rigid. Conductive region 2116 is a plate of the capacitor formed in interconnect 3106. Interconnect 2126 couples conductive region 2116 to the electronic circuitry 3110. Conductive region 2116 and interconnect 2126 couples to support surface 3128. In the example, conductive region 2116 and interconnect 2126 are coupled to ground. Conductive region 2116 acts as a shield to prevent signal or parasitic coupling to conductive regions 2110 and 2108 of sensor 2100. Similarly, interconnect 2126 acts as a shield for interconnect 2124 to prevent signal or parasitic coupling. In one embodiment, support surface 3128 comprises a conductive material such as metal. Thus, structure 3104 is coupled to ground by way of conductive region 2116 and interconnect 2126. Structure 3104 acts as a shield for preventing signal or parasitic coupling to the capacitive sensors.

Support surface 3114 of structure 3102 is supported by load pad 3108 and sensor 2100. Load pad 3108 distributes the load to sensor 2100. Support surface 3114 is compliant to loading placed thereon. In one embodiment, support surface 3114 made thin to allow flexing. In general, support surface 3114 deflects a short distance over the entire load range. Sensor 2100 can elastically compress approximately 20% of the total dielectric thickness. In one embodiment, compression of sensor 2100 is limited to 10% or less of the total dielectric thickness. For example, a capacitor as disclosed herein can compress approximately 0.00254 millimeters over the load range of a typical prosthetic component load sensor.

In one embodiment, a stack three capacitive sensors in series, lamination material, and insulating material would yield a total compression under maximum loading of approximately 0.0076 millimeters. Thus, support surfaces 3112 or 3114 do not flex significantly over the entire load range. Load pad 3108 couples to a known location on support surface 3114. The known location also relates to a point on the articular surface of the insert. The known location of each of the sensors is used to determine where the load is coupled to the articular surface by comparing the measured load magnitudes. Although a single sensor is shown, the other sensors formed in interconnect 3106 are similarly coupled to structures 3102 and 3104. Hermetic seal 3302 couples structures 3102 and 3104 together. Hermetic seal 3302 can be a weld that melts and joins the material of structures 3102 and 3104.

Conductive region 2112 is a plate of the capacitor formed in interconnect 3106. Interconnect 2124 couples conductive region 2112 to electronic circuitry 3110. In the example, conductive region 2112 and interconnect 2124 are coupled to ground. Conductive region 2108 and conductive region 2110 are plates of the capacitor formed in the interconnect 3106. Conductive regions 2108 and 2110 of sensor 2100 are coupled in common by via 2120. Interconnect 2122 couples the conductive regions 2108 and 2110 to the electronic circuitry. Interconnect 2122 carries a signal from the electronic circuitry to sensor 2100 to measure the capacitor. Conductive region 2112 is separated from conductive region 2108 by dielectric layer 2104. Similarly, conductive region 2116 is separated from conductive region 2110 by dielectric layer 2106. Conductive regions 2108 and 2110 are separated by a dielectric layer 2102 but as mentioned previously are coupled in common. In one embodiment, dielectric layers 2102, 2104, and 2106 comprise polyimide. Other dielectrics such as silicon dioxide, silicon nitride, mylar, and other polymers can be used. Interconnect 3106 and sensor 2100 can be formed by deposition, plating, and lithographic techniques on the substrate.

The capacitor of sensor 2100 comprises three capacitors mechanically in series. A force, pressure, or load applied to support surface 3114 compresses the three capacitors. A first capacitor comprises conductive region 2112, dielectric layer 2104, and conductive region 2108. A second capacitor comprises conductive region 2108, dielectric layer 2102, and conductive region 2110. A third capacitor comprises conductive region 2108, dielectric layer 2106, and conductive region 2116. Electrically, the capacitor of sensor 2100 comprises the first and third capacitors coupled in parallel. The first and third capacitors have conductive regions 2108 and 2110 coupled in common. Similarly, conductive regions 2112 and 2116 of the first and third capacitors are coupled to ground. Conductive region 2112 and 2116 respectively shield conductive region 2108 and 2110 from coupling and parasitic capacitance external to interconnect 3106. Similarly, interconnect 2124 and 2126 shield interconnect 2122 from signal coupling and parasitic capacitance external to interconnect 3106.

Structures 3102 and 3104 can comprise a conductive material. For example, titanium, cobalt, and steel alloys are conductive materials used to manufacture prosthetic component 3100. Placing interconnect 3106 on support surface 3128 couples conductive region 2116 and interconnect 2126 to structure 3104. Conductive region 2116 and support surface 3128 are coupled in common to ground. Similarly, load pad 3108 can comprise a conductive material. In one embodiment, a material such as copper or copper alloy can be deposited or plated to the surface of interconnect 3106. Load pad 3108 is coupled to conductive region 2112 and interconnect 2124. Support surface 3114 is coupled to conductive region 2112 and interconnect 2124 by load pad 3108. As mentioned previously, conductive region 2112 and interconnect 2124 are coupled to ground. Thus, structure 3102 and 3104 are coupled to ground. Alternatively, structures 3102 and 3104 can be coupled to ground via an alternate path other than sensor 2100. In one embodiment, the electronic circuitry and sensor 2100 are housed in prosthetic component 3100. Structures 3102 and 3104 form a shield that isolates electronic circuitry 3110 and sensor 2100 from parasitic coupling and parasitic capacitance in the external environment. The design further incorporates the internal shields built into the capacitor that prevents or minimizes parasitic coupling and parasitic capacitance external to interconnect 3106. Although a capacitive sensor is used in the example, the load sensor in prosthetic component 3100 can comprises one of a strain gauge, mems device, piezo-resistive sensor, mechanical sensor, polymer sensor, and ultrasonic sensor.

Figure 37:
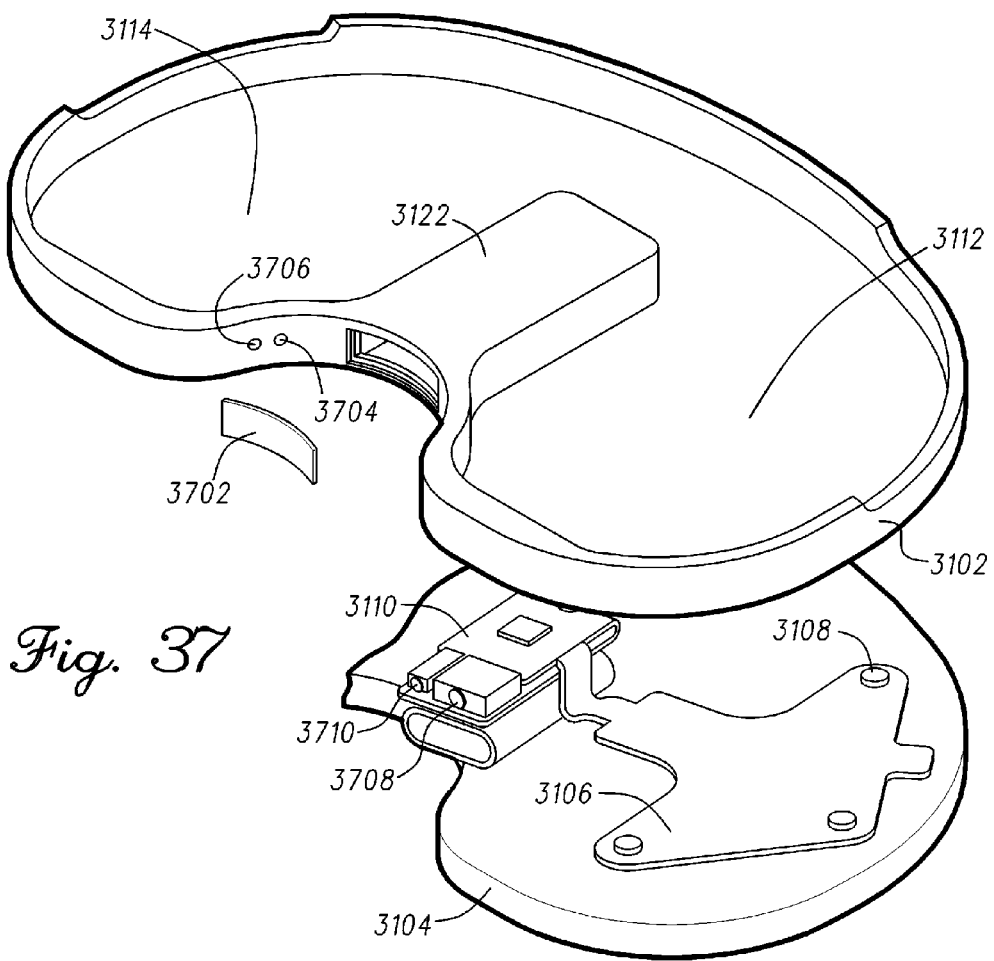
FIG. 37 illustrates the structure and electronic circuitry in accordance with an example embodiment.

FIG. 37 illustrates structure 3102 in accordance with an example embodiment. Structure 3102 of prosthetic component 3100 when installed in a joint region of the patient includes at least one region having exposure external to the joint. The view shows housing 3122 of structure 3102 that includes a transmissive region 3702. In one embodiment, transmissive region 3702 comprises glass, PEEK, plastic, or polymer. Transmissive region 3702 can be bonded to an opening in a wall of housing 3122 that comprises a steel alloy, titanium, cobalt, an alloy, or metal. In one embodiment, housing 3122 houses electronic circuitry. Alternatively, part of or all of structure 3102 can comprise a polymer such as PEEK, which is transmissive to some of the spectrum. In one embodiment, transmissive region 3702 is transmissive to sensor signals and communication signals. For example, signals can be blocked when structure 3102 comprises a conductive material and the conductive material is grounded. Prosthetic component 3100 can act as a shield to the electronic circuitry and sensors housed within the device. Transmissive region 3702 can be transmissive to signals such as acoustic, ultrasonic, radio frequency, infrared, and light. Transmissive region 3702 has exposure to regions around and in proximity to the joint region. In one embodiment, window 3702 can be used to monitor the synovial fluid that resides in and around the joint.

Sensors can also be located at or near transmissive region 3702. The sensors can be mounted with electronic circuitry 3110. Electronic circuitry 3110 can comprise one or more pc boards having interconnect and connectors. Integrated circuits, ASIC devices, a power source, communication circuitry, digital logic, converters, power management, and other systems can be coupled together in a small form factor. In one embodiment, an ASIC combines many of the features to minimize form factor and to lower power consumption. Sensors and communication circuitry are located on electronic circuitry 3110 in proximity to transmissive region 3122 allowing transmission and reception of signals. A directional antenna can be placed in proximity to transmissive region 3702 to send and receive information to a remote system.

In general, sensors can be used to monitor the synovial fluid that is in proximity to the joint region. Synovial fluid is a natural lubricant found in a muscular-skeletal joint. Synovial fluid is found in joints such as the elbow, knee, shoulder, hip and others. Synovial fluid comprises mucin, albumin, fat, epthelium, and leukocytes. The lubricant also nourishes the avascular articular cartilage. Synovial fluid cushions joint impact and reduces friction as bone and cartilage contact one another over the range of motion. Synovial fluid can also carry oxygen and other nutrients to cartilage and other areas of the joint. Similarly, synovial fluid acts as transport to remove waste materials from the joint region. The synovial fluid remains in and around the joint. The synovial fluid can be retained by a synovial membrane that holds the lubricant in place.

There is a strong correlation between the health of a joint and the condition of the synovial fluid. Sensors that measure temperature, pH, color, turbidity, viscosity, glucose, and proteins can be used to analyze synovial fluid. The sensors can be used individually or in concert with one another to determine joint health. Prosthetic component 3100 includes one or more of the sensors for monitoring the joint. In the example, the joint is monitored for infection. Infection in a newly implanted joint is a critical problem. It is often difficult for a patient with a joint implant to determine if he or she has an infection. The surgery itself and joint rehabilitation can mask early signs of an infection. The prosthetic joint is an ideal place for an infection to grow without abatement. There are areas in the prosthetic joint that are isolated but have nutrients that can harbor bacteria and foster growth. Infection can lead to a substantial health risk, anti-biotic treatment, increased rehabilitation, long-term hospitalization, and substantial cost. If the infection is significant there is a scenario that requires the removal of the prosthetic joint. The patient is immobilized until the infection subsides and then a new prosthetic joint is implanted. The patient trauma under such circumstances can be significant. Prosthetic joint 3100 can detect infection local to the joint, notify a doctor or healthcare provider, or take appropriate action in a timely manner.

In one embodiment, temperature can be monitored. A temperature sensor 3704 can be mounted in proximity to transmissive region 3702. Temperature sensor 3704 is coupled to electronic circuitry 3110 for receiving temperature data. In one embodiment, electronic circuitry 3110 has multiple I/O channels for coupling to sensors. Temperature sensor 3704 monitors the temperature of the joint. In one embodiment, temperature sensor 3704 measures the temperature of the synovial fluid. Measurements of the synovial fluid can occur periodically.

A temperature difference can be detected between a healthy knee and an infected knee. In the example, temperature sensor 3704 is calibrated to a normal temperature of the synovial fluid. The calibrations can occur periodically because the normal temperature will change depending on the patient condition. The absolute temperature and changes in temperature are monitored. A change in temperature from the norm can be an indication of an infection. In the example, temperature sensor can be a MEMS sensor, a thermocouple, thermistor or other temperature measuring device.

In one embodiment, pH can be monitored. A pH sensor 3706 can be mounted in proximity to transmissive region 3702 and coupled to electronic circuitry 3110 for receiving pH data. Similar to temperature, pH sensor 3706 can be initially calibrated to the normal pH and recalibrated periodically. A lower pH than the norm can indicate the presence of an infection. Measurement of absolute pH and differential pH over time can be used to detect an increase in bacteria. In general, a healthy knee has a pH of approximately 7.23. An infected knee has a pH of approximately 7.06. The device can be calibrated for specifics of an individual patient. The pH sensor can be a MEMS pH sensor, an implantable pH microsensor, electro-static pH sensor, or other pH measuring device.

In one embodiment, turbidity and color can be monitored. Turbidity is a measure of the cloudiness or haze due to the suspension of particles within a fluid. For example, synovial fluid becomes turbid as an infection grows. Bacteria, bacterial waste products, and white blood cells are but a few of the particulates that can be suspended in the synovial fluid. The turbidity increases as the infection worsens due to increased bacterial growth. Similarly, the color of the synovial fluid changes as an infection increases. For example, healthy synovial fluid is a relatively clear fluid. The synovial fluid changes color as the joint status changes from healthy to non-inflammatory, non-inflammatory to inflammatory, and inflammatory to septic. A non-inflammatory synovial fluid is a yellowish clear liquid that is indicative of joint related problems such as osteoarthritis. The synovial fluid will be viscous retaining its lubricating and damping properties. An inflammatory synovial fluid is yellowish in color. The inflammatory synovial fluid is hazy and not clear. It will also have lost some of its viscous properties having a watery consistency. The inflammatory synovial fluid can indicate problems such as rheumatoid arthritis or infection. Septic synovial fluid can be dark yellow to red in color. Moreover, septic synovial fluid is opaque. The synovial fluid can contain high counts of bacteria, fungus, white, and red blood cells. Measuring color, turbidity, or a combination of both can be used to determine joint health.

In the example, optical sensors such as a LED 3708 (light emitting diode) and photo-diode array 3710 can be used to measure color and turbidity. In one embodiment, the LED 3708 and photo-diode array 3710 are positioned behind transmissive region 3702. LED 3708 and photo-diode array 3710 are housed within prosthetic component 3100 and can couple to or be part of electronic circuitry 3110. As previously mentioned, transmissive region 3702 can be glass that is transmissive to light. LED 3708 can transmit white light directly to a photo-diode. The photo-diode can be part of photo-diode array 3710 or a separate device. The photo-diode can be used for calibration of LED 3708 and for detecting changes in the light or intensity output by the device. LED 3708 also illuminates a sample of synovial fluid. As shown, light emitted by LED 3708 is transmitted through transmissive region 3702 into the synovial fluid in proximity to prosthetic component 3100. In one embodiment, three photo-diodes respectively having red, green, and blue optical filters detect light transmitted through the synovial fluid. Each photo-diode measures the relative contribution of red, green, and blue. The contribution can be ratiometrically compared with a calibration value corresponding to a measurement by the calibration photo-diode. The calibration value corresponds to the sum of red, green, and blue components of white light. More than one transmissive region can be used to send and receive light. Also, one or more barriers or transmissive regions can be used to direct the light into the synovial fluid and prevent direct light from LED 3708 from radiating onto photo-diode array 3710.

Equations for the measurement can be as follows:
a) r=red, g=green, b=blue, c=calibration
b) Color=[r, g, b]/(r+g+b)
c) Turbidity=(r+g+b)/3c The color measured by photo-diode array 3710 can be compared to known infection color data. Similarly, the turbidity measurements by photo-diode array 3710 can be compared against known turbidity color data. Both color and turbidity measurements can be taken by prosthetic component 3100. Using both measurements in combination can provide data that allows further refinement of the prognosis thereby providing a better assessment and treatment methodology. Furthermore, taking periodic measurements and comparing the color and turbidity measurements can yield a rate of change. The rate of change can be used to determine if the infection is increasing or declining. Comparing measurements over time can be used to determine if the infection treatment is successful. Placing sensors in the prosthetic component has substantial benefits in preventing infection. Statistically most infections occur shortly after the joint implant or within the first few months after surgery. Infection is less likely to occur after the surgical wound has healed and rehabilitation of the joint has taken place. Pain due to the surgery and during rehabilitation can also mask infection symptoms. If an infection occurs, it will start as a local infection in proximity to the joint. A first benefit is that prosthetic component 3100 can identify an infection that is local to the joint before it has spread throughout the body. A second benefit is that treatment of the infection can be local to the joint region. A third benefit is that prosthetic component 3100 can also include an antibiotic that could be released in proximity to the joint. A fourth benefit is that prosthetic component 3100 can be in communication with a remote system and a database. The remote system can be provide notification to the patient to see a doctor. The remote system can also provide data to the doctor for analysis and treatment.

A method of long-term joint monitoring is disclosed using prosthetic component 3100. The method can be practiced with more or less than the steps shown, and is not limited to the order of steps shown. The method is not limited to the example tibial prosthetic component example but can be used for hip, shoulder, ankle, elbow, spine, hand, foot, and bone. In a first step, electronic circuitry and one or more sensors are housed in a prosthetic component. In a second step, characteristics of synovial fluid are periodically measured in proximity to the prosthetic component. The characteristic can be used to determine the presence of an infection or other problem. Examples of measured characteristics are temperature, pH, color, turbidity, viscosity, glucose levels, and proteins. In a third step, measurements are compared. In one embodiment, measurements compared against one another to determine if a change has occurred. Furthermore, multiple measurements made over time can indicate a trend. In another embodiment, the measured characteristics can be compared against known or predetermined values that relate to infection or other problem being identified.

In a fourth step, a color of the synovial fluid is measured. In a fifth step, the color of the synovial fluid is compared against a known color range. In a sixth step, it can be determined if an infection is present. In one embodiment, the comparison yields a color similar to a known synovial fluid color. For example, clear synovial fluid is normal. A clear yellow synovial fluid can indicate inflammation and other problems. A hazy yellow synovial fluid can indicate the presence of bacteria or other problems. A synovial fluid having a red tint can indicate sepsis and blood in the synovial fluid.

In a seventh step, the relative contributions of red, green, and blue colors are measured. In an eighth step, a contribution of each color is ratiometrically compared to a sum of the relative contributions. A color of the synovial fluid can be determined by assessing the contributions of red, green, and blue colors. In a ninth step, a rate of change in color is determined. The rate of change in color can be used to determine the status of an infection. For example, once an infection is detected the rate of change corresponds to a decrease or increase in the infection. It can also be used to determine the effectiveness of treatment. After treatment the rate of change should indicate a decrease in the infection.

A method of long-term joint monitoring is disclosed using prosthetic component 3100. The method can be practiced with more or less than the steps shown, and is not limited to the order of steps shown. The method is not limited to the example tibial prosthetic component example but can be used for hip, shoulder, ankle, elbow, spine, hand, foot, and bone. In a first step, electronic circuitry and one or more sensors are housed in a prosthetic component. In a second step, a turbidity of synovial fluid is periodically measured in proximity to the prosthetic component. The turbidity can be used to determine the presence of an infection or other problem. Examples of other measured characteristics are temperature, pH, color, turbidity, viscosity, glucose levels, and proteins. In a third step, the turbidity measurements are compared to known turbidity measurements or a predetermined turbidity range. In one embodiment, comparing the periodic measurements determine if a change has occurred. Furthermore, multiple turbidity measurements taken over time can indicate a trend. In another embodiment, the measured characteristics can be compared against known or predetermined turbidity values that relate to infection or other problem being solved. In a fourth step, it can be determined if an infection is present. Turbidity is a measure of the cloudiness or haziness of a substance. For example, healthy synovial fluid is clear. Conversely, infected synovial fluid is hazy or cloudy due to the presence of bacteria. Moreover, the severity of the infection can be related to the number of particulates in the synovial fluid. The higher the number of particulates the worse the infection can be.

In a fifth step, the turbidity is compared against previous turbidity measurements. In a sixth step, a rate of change in turbidity is determined. In general, if the turbidity increases the infection or problem is worsening because healthy synovial fluid is clear. Alternatively, if treatment has been provided and the turbidity over time is decreasing than the patient health is improving. In a seventh step, data is wirelessly transmitted to a remote system. In one embodiment, the remote system is in proximity to the prosthetic component due to the limited range of transmission. The remote system can include a processor and graphic processor. In an eighth step, light is received through a transmissive region of the prosthetic component. Light is transmitted into the synovial fluid in proximity to the prosthetic component. The light illuminates the synovial fluid that is detected by a photo-diode array. Each diode of the photo-diode array can have a filter for filtering the incoming light through the transmissive region of the prosthetic component.

Figure 38:
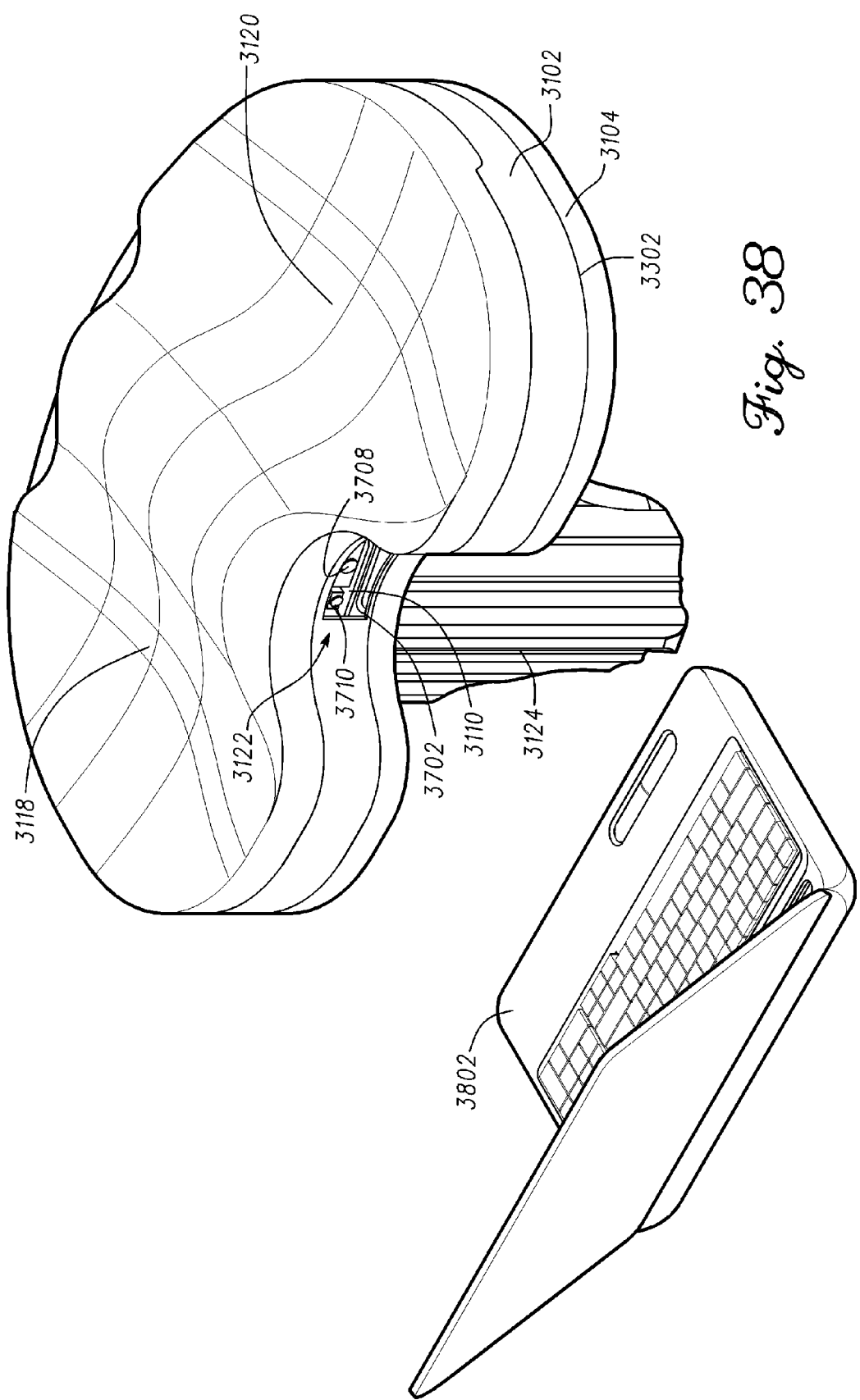
FIG. 38 illustrates the prosthetic component and a remote system in accordance with an example embodiment.

FIG. 38 illustrates prosthetic component 3100 and a remote system 3802 in accordance with an example embodiment. Remote system 3802 can be equipment, a tool, a computer, a note pad, a cell phone, a smartphone, or medical device. Data transmitted from prosthetic component 3100 is received by remote system 3802. Similarly, remote system 3802 can transmit information to prosthetic component 3100 that supports operation and sensor measurement. Remote system 3802 can include logic circuitry, microprocessor, microcontroller, or digital signal processor. In the example, remote system 3802 is a laptop computer with a display. Remote system 3802 can include software for analyzing quantitative measurement data from prosthetic component 3100 and displaying the information for assessment. Remote system 3802 includes transmit circuitry, receive circuitry, or both for coupling to electronic circuitry 3110 of prosthetic component 3100. Similarly, electronic circuitry 3110 includes transmit circuitry, receive circuitry, or both. In the example, electronic circuitry includes an ASIC having transmit and receive circuitry. In one embodiment, transmit and receive circuitry transmits through transmissive region 3702. Alternatively, other transmissive regions can be added to prosthetic component 3100 for supporting antenna placement. Also, prosthetic component 3100 can be made from a polymer such as PEEK that allows transmission and reception of signals. In one embodiment, transmission of data to remote system 3802 is short range. The transmission range is typically less than 10 meters. In an installed prosthetic component, the RF transmission is made through tissue. The short transmission distance reduces un-authorized reception of data. In one embodiment, the data transmission is encrypted for security. The data can be decrypted by remote system 3802.

In the example, housing 3122 includes electronic circuitry 3110 and a window 3702. Window 3702 can be transmissive to signals such as acoustic, ultrasonic, radio frequency, infrared, and light. Window 3702 can comprise glass that is bonded to the steel, titanium, cobalt, alloy, or metal of the prosthetic component. Alternatively, part of or all of structure 3102 can comprise a plastic or a polymer such as PEEK, which is transmissive to some of the spectrum. Window 3702 is not blocked by other components of the prosthetic joint and has exposure to regions around and in proximity to the joint region. In one embodiment, window 3702 can be used to monitor a region in proximity to the prosthetic joint. Similarly, sensors can be fastened to structure 3102 or 3104 and exposed to the region. Window 3702 can be used to measure one or more parameters that relate to the health of synovial fluid. In the example, optical sensors are used to measure color and turbidity. Electronic circuitry 3110 couples to each of the sensors. In one embodiment, a channel is assigned to each sensor. The channels can be operated serially or in parallel. Logic circuitry in electronic circuitry 3110 controls when measurements are taken. The measurement data can be stored in memory on electronic circuitry 3110 until transmitted. The measurement data can be converted to a digital format. The quantitative parameter measurements can be used individually or in combination to determine a health issue.

A method of long-term joint monitoring is disclosed using prosthetic component 3100. The method can be practiced with more or less than the steps shown, and is not limited to the order of steps shown. The method is not limited to the example tibial prosthetic component example but can be used for hip, shoulder, ankle, elbow, spine, hand, foot, and bone. In a first step, electronic circuitry and one or more sensors are housed in a prosthetic component. In a second step, synovial fluid in proximity to the prosthetic component is monitored. In a third step, a characteristic of the synovial fluid is measured. Examples of characteristics being measured are temperature, pH, color, turbidity, viscosity, glucose levels, and proteins. In a fourth step, data is sent to a remote system. The data can be wirelessly transmitted from the prosthetic component to the remote system. The remote system can include digital logic, a processor, a digital signal processor, a graphic processor, communication circuitry, or analog circuitry. In one embodiment, the transmission can be less than 10 meters due to power constraints of the signal and the medium in which it travels. For example, the transmission has to be sent through the multiple layers of tissue between the prosthetic component and the external environment.

In a fourth step, the data sent by the prosthetic component can be analyzed. The data can be analyzed by the remote system. The data can also be sent to other equipment, devices, computers, or a database. The data can be combined with other information or data to create a clinical database related to a study of the joint or prosthetic system. In a fifth step, a report is generated. The report is based on quantitative data provided by the sensors in the prosthetic component. In a sixth step, the report is sent to at least one entity. In general, the report uses quantitative data generated by the sensors in the prosthetic component. In the example, the sensor data can be an analysis of the synovial fluid in proximity to the joint. The report can lead to an action being taken. For example, detecting an infection or a condition such as arthritis can lead to treatment. The sensors can be used to monitor progress of the treatment. In a seventh step, temperature of the synovial fluid can be measured. In an eighth step, pH of the synovial fluid can be measured. In a ninth step, the color or turbidity of the synovial fluid can be measured. The report can be as simple as a status update on the sensor data to the patient or a detailed listing of all the parameters measured, trends, and analysis of the data sent to a health care provider such as a doctor, surgeon, or hospital. The entity can be broadly interpreted as anything or anybody that has rights to use the information. The report can be encrypted to maintain privacy of the information. Similarly, the sensor data can also include the load and position of load data. This sensor data can be used to address kinematic issues regarding the joint and how the patient is adapting to the prosthesis.

Figure 39:
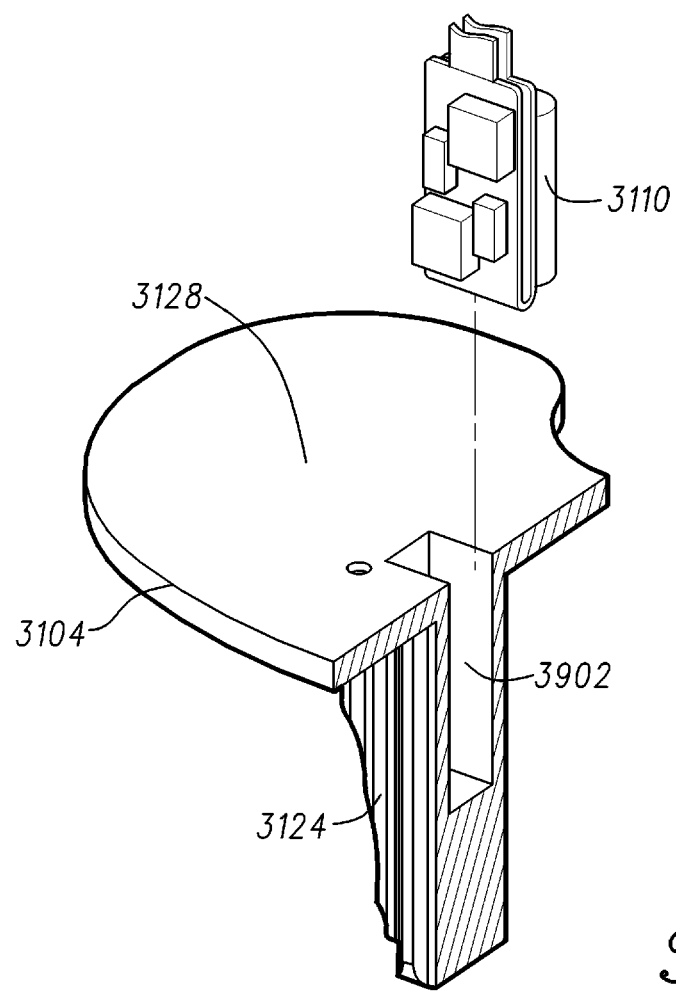
FIG. 39 is an illustration of the electronic circuitry and the structure in accordance with an example embodiment.

FIG. 39 is an illustration of electronic circuitry 3110 and structure 3104 in accordance with an example embodiment. Structure 3104 is a component of prosthetic component 3100 disclosed herein. Structure 3104 can includes a cavity 3902 for housing electronic circuitry 3110. Electronic circuitry 3110 is placed vertically into cavity 3902. Cavity 3902 extends into stem 3124 of structure 3104. In general, the electronic circuitry can be housed within structure 3102, 3104, or both.

Figure 40:
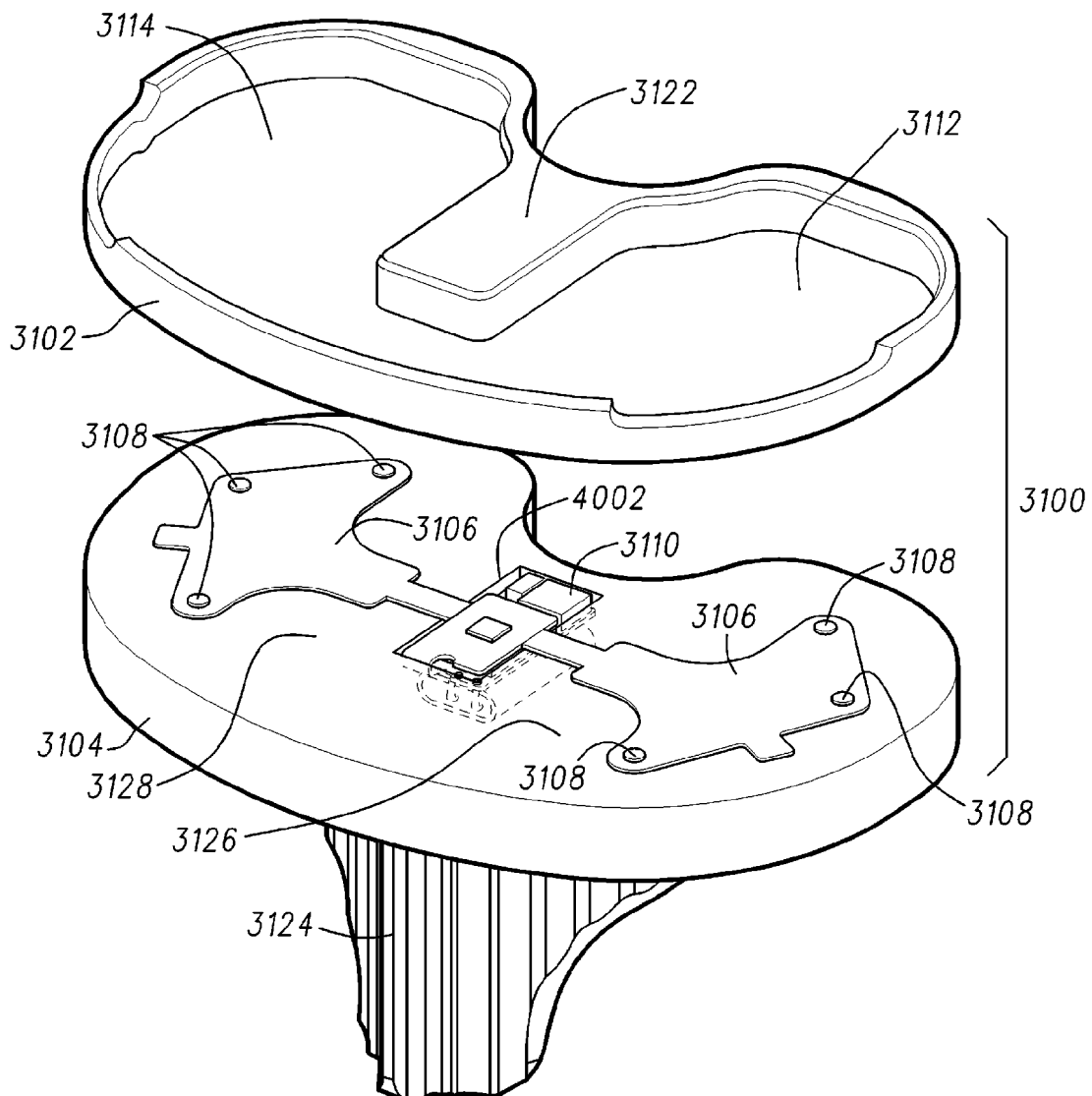
FIG. 40 is an illustration of the electronic circuitry and the structure in accordance with an example embodiment.

FIG. 40 is an illustration of electronic circuitry 3110 and structure 3104 in accordance with an example embodiment. Structure 3104 can include a cavity 4002 for housing electronic circuitry 3110. Electronic circuitry 3110 is placed horizontally into cavity 4002. Cavity 4002 is centered between interconnect 3106 in a lightly loaded region of prosthetic component 3100. Sensors such as temperature, pH, optical, glucose, and others can be mounted in housing 3122 and coupled to electronic circuitry 3110. Cavity 4002 underlies housing 3122 and provides room to accommodate sensors for measuring in proximity to prosthetic component 3100. Interconnect 3106 overlies support surface 3126 and 3128. Each interconnect 3106 includes a sensor array and corresponds to a compartment of the knee. Sensors underlie load pad 3108 of interconnect 3106 for measuring a force, pressure, or load. Electronic circuitry 3110 can include accelerometers for providing positioning information of the joint.

Figure 41:
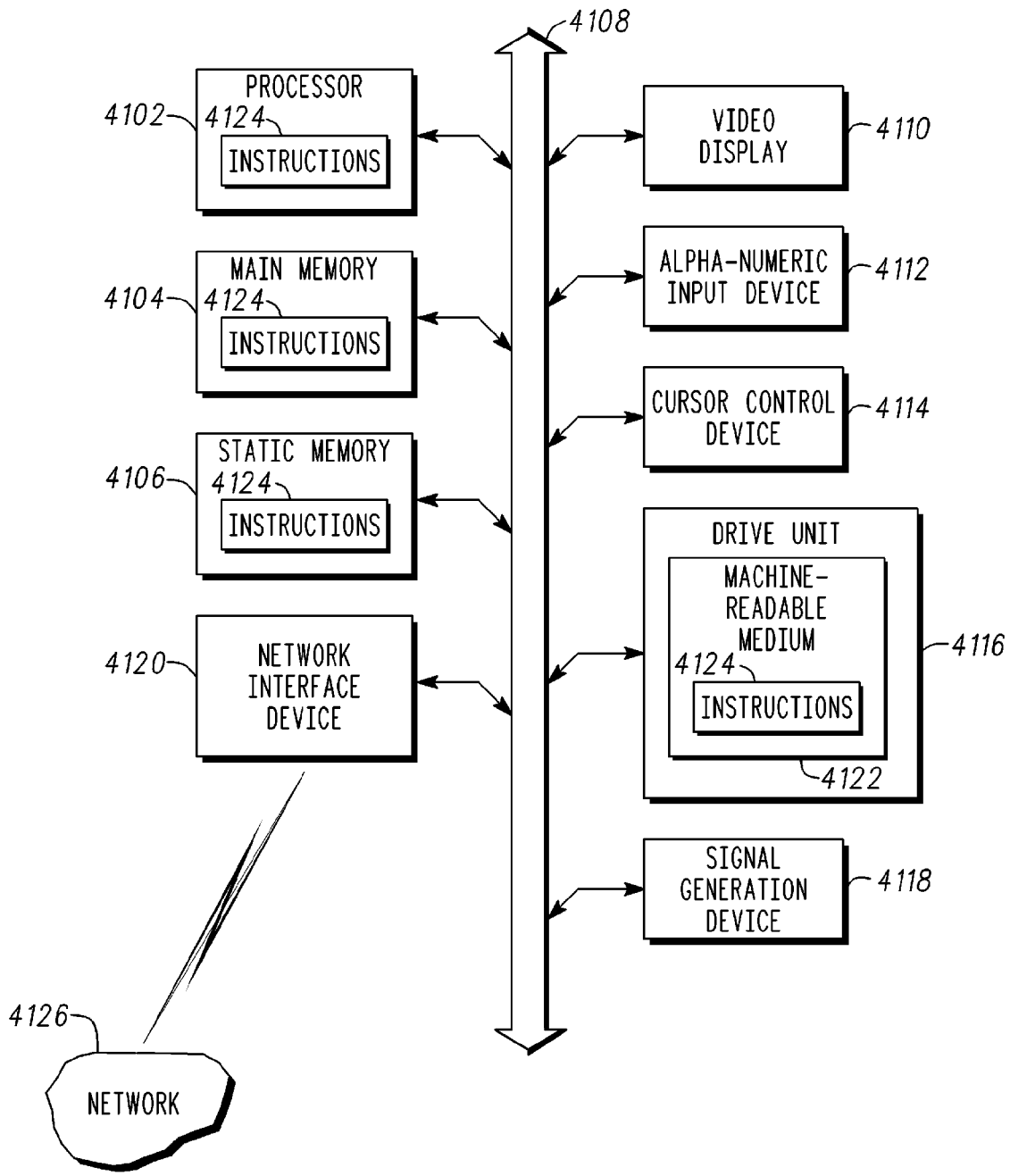
FIG. 41 depicts an exemplary diagrammatic representation of a machine in the form of a system within which a set of instructions are executed in accordance with an example embodiment.

FIG. 41 depicts an exemplary diagrammatic representation of a machine in the form of a system 4100 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, logic circuitry, a sensor system, an ASIC, an integrated circuit, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

System 4100 may include a processor 4102 (e.g., a central processing unit (CPU), a graphics processing unit (GPU, or both), a main memory 4104 and a static memory 4106, which communicate with each other via a bus 4108. System 4100 may further include a video display unit 4110 (e.g., a liquid crystal display (LCD), a flat panel, a solid state display, or a cathode ray tube (CRT)). System 4100 may include an input device 4112 (e.g., a keyboard), a cursor control device 4114 (e.g., a mouse), a disk drive unit 4116, a signal generation device 4118 (e.g., a speaker or remote control) and a network interface device 4120.

The disk drive unit 4116 can be other types of memory such as flash memory and may include a machine-readable medium 4122 on which is stored one or more sets of instructions (e.g., software 4124) embodying any one or more of the methodologies or functions described herein, including those methods illustrated above. Instructions 4124 may also reside, completely or at least partially, within the main memory 4104, the static memory 4106, and/or within the processor 4102 during execution thereof by the system 4100. Main memory 4104 and the processor 4102 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 4124, or that which receives and executes instructions 4124 from a propagated signal so that a device connected to a network environment 4126 can send or receive voice, video or data, and to communicate over the network 4126 using the instructions 4124. The instructions 4124 may further be transmitted or received over a network 4126 via the network interface device 4120.

While the machine-readable medium 4122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Figure 42:
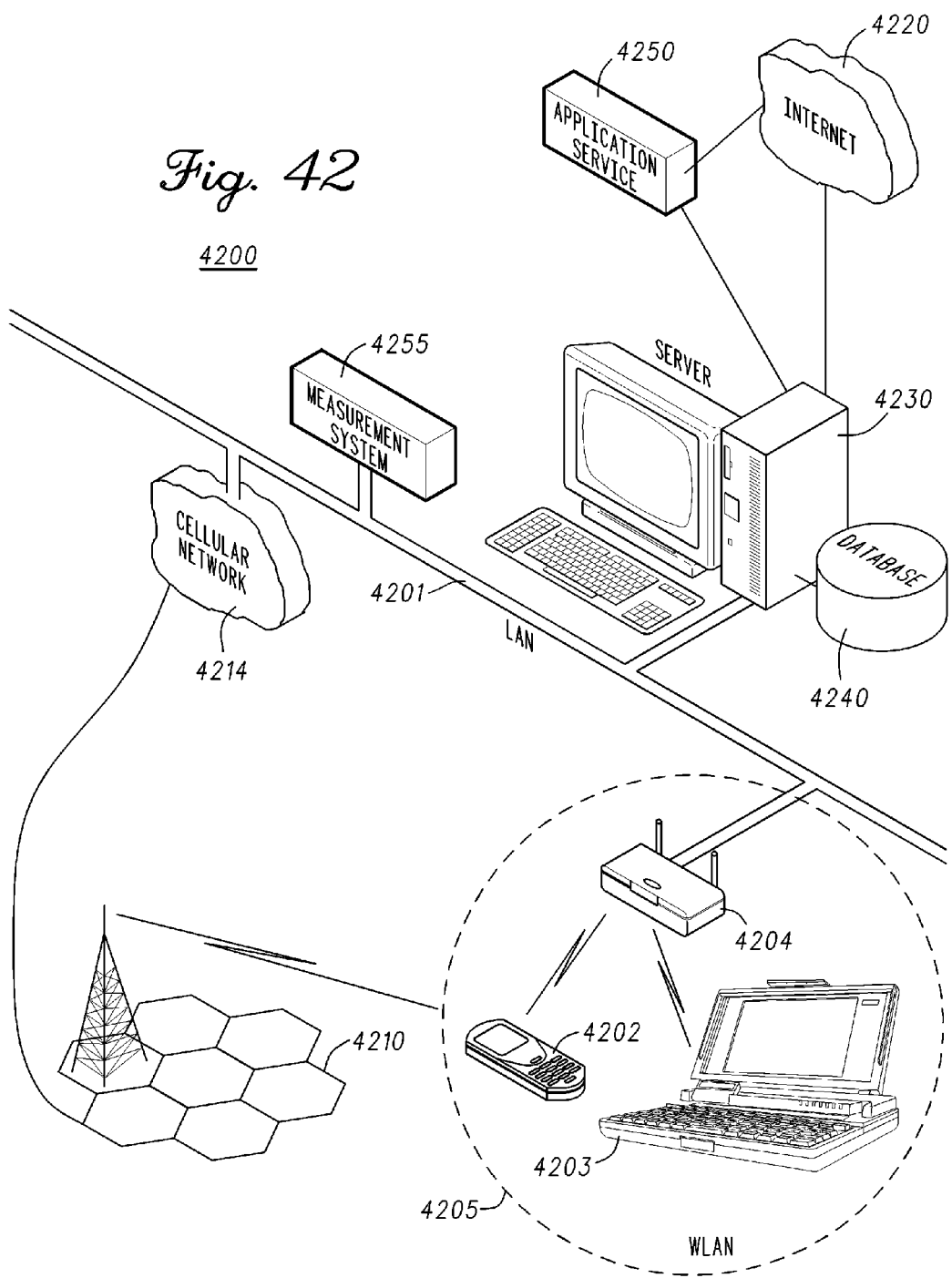
FIG. 42 is an illustration of a communication network for measurement and reporting in accordance with an example embodiment.

FIG. 42 is an illustration of a communication network 4200 for measurement and reporting in accordance with an exemplary embodiment. Briefly, the communication network 4200 expands broad data connectivity to other devices or services. As illustrated, the measurement and reporting system 4255 can be communicatively coupled to the communications network 4200 and any associated systems or services.

As one example, measurement system 4255 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 4200 can further be tied to an Electronic Medical Records (EMR) system to implement health information technology practices. In other embodiments, the communication network 4200 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 4200 can provide wired or wireless connectivity over a Local Area Network (LAN) 4201, a Wireless Local Area Network (WLAN) 4205, a Cellular Network 4214, and/or other radio frequency (RF) system (see FIG. 4). The LAN 4201 and WLAN 4205 can be communicatively coupled to the Internet 4220, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 4200 can utilize common computing and communications technologies to support circuit-switched and/or packet-switched communications. Each of the standards for Internet 4220 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 4214 can support voice and data services over a number of access technologies such as GSM-GPRS, EDGE, CDMA, UMTS, WiMAX, 2G, 3G, WAP, software defined radio (SDR), and other known technologies. The cellular network 4214 can be coupled to base receiver 4210 under a frequency-reuse plan for communicating with mobile devices 4202.

The base receiver 4210, in turn, can connect the mobile device 4202 to the Internet 4220 over a packet switched link. The internet 4220 can support application services and service layers for distributing data from the measurement system 4255 to the mobile device 4202. Mobile device 4202 can also connect to other communication devices through the Internet 4220 using a wireless communication channel.

The mobile device 4202 can also connect to the Internet 4220 over the WLAN 4205. Wireless Local Access Networks (WLANs) provide wireless access within a local geographical area. WLANs are typically composed of a cluster of Access Points (APs) 4204 also known as base stations. The measurement system 4255 can communicate with other WLAN stations such as laptop 4203 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etcetera).

By way of the communication network 4200, the measurement system 4255 can establish connections with a remote server 4230 on the network and with other mobile devices for exchanging data. The remote server 4230 can have access to a database 4240 that is stored locally or remotely and which can contain application specific data. The remote server 4230 can also host application services directly, or over the internet 4220.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or device may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. An orthopedic system comprising:
   a sensor;
   electronic circuitry coupled to the sensor where the electronic circuitry includes a transmitter and where the transmitter is configured to transmit measurement data; and
   a light source configured to illuminate a region in proximity to the muscular-skeletal system where the electronic circuitry is in a housing and where the housing is coupled to the muscular-skeletal system.

2. The orthopedic system of claim 1 further including a remote system configured to receive and process the measurement data.

3. The orthopedic system of claim 1 where the housing has a transmissive region.

4. The orthopedic system of claim 3 where the transmissive region comprises glass.

5. The orthopedic system of claim 3 where the transmissive region comprises plastic.

6. The orthopedic system of claim 3 where the transmitter is configured to transmit through the transmissive region.

7. The orthopedic system of claim 3 where the sensor is an optical sensor and where the optical sensor is configured to detect through the transmissive region.

8. The orthopedic system of claim 1 where the sensor is an optical sensor and where the optical sensor measures color or turbidity.

9. The orthopedic system of claim 1 where the sensor is a temperature sensor or a pH sensor.

10. An orthopedic system comprising:
    a sensor;
    electronic circuitry coupled to the sensor where the electronic circuitry includes a transmitter and where the transmitter is configured to transmit measurement data; and
    a light emitting diode configured to illuminate a region in proximity to the muscular-skeletal system where the electronic circuitry is in a housing and where the housing is coupled to the muscular-skeletal system.

11. The orthopedic system of claim 10 where the housing has a transmissive region.

12. The orthopedic system of claim 11 where the transmissive region comprises glass.

13. The orthopedic system of claim 11 where the transmissive region comprises plastic.

14. The orthopedic system of claim 11 where the transmitter is configured to transmit through the transmissive region.

15. The orthopedic system of claim 11 where the sensor is an optical sensor and where the optical sensor is configured to detect through the tranmissive region.

16. The orthopedic system of claim 15 further including a pH or temperature sensor.

17. The orthopedic system of claim 15 where the optical sensor is configured to detect color or turbidity.

18. An orthopedic system comprising:
   a sensor;
   electronic circuitry coupled to the sensor where the electronic circuitry includes a transmitter and where the transmitter is configured to transmit measurement data;
   a light source configured to illuminate a region in proximity to the muscular-skeletal system where the electronic circuitry is in a prosthetic component configured to couple to the muscular-skeletal system.

19. The orthopedic system of claim 18 further including a remote system configured to receive and process the measurement data.

20. The orthopedic system of claim 18 where the prosthetic component has a transmissive region and where the sensor is configured to detect through the transmissive region.

* * * * *